US008822193B2

(12) United States Patent
Asolkar et al.

(10) Patent No.: US 8,822,193 B2
(45) Date of Patent: Sep. 2, 2014

(54) **ISOLATED BACTERIAL STRAIN OF THE GENUS *BURKHOLDERIA* AND PESTICIDAL METABOLITES THEREFROM**

(71) Applicant: Marrone Bio Innovations, Inc., Davis, CA (US)

(72) Inventors: Ratnakar Asolkar, Davis, CA (US); Marja Koivunen, Davis, CA (US); Pamela Marrone, Davis, CA (US); Ana Lucia Cordova-Krevlos, Davis, CA (US); Huazhang Huang, Durham, NC (US)

(73) Assignee: Marrone Bio Innovations, Inc., Davis, CA (US)

( * ) Notice: Subject to any disclaimer, the term of this patent is extended or adjusted under 35 U.S.C. 154(b) by 0 days.

(21) Appl. No.: 13/843,971

(22) Filed: Mar. 15, 2013

(65) Prior Publication Data

US 2014/0073501 A1    Mar. 13, 2014

Related U.S. Application Data

(63) Continuation-in-part of application No. 13/034,575, filed on Feb. 24, 2011.

(60) Provisional application No. 61/308,287, filed on Feb. 25, 2010, provisional application No. 61/406,541, filed on Oct. 25, 2010.

(51) Int. Cl.
| | |
|---|---|
| *C12N 1/20* | (2006.01) |
| *A01N 63/02* | (2006.01) |
| *C12P 17/16* | (2006.01) |
| *C07D 498/14* | (2006.01) |
| *C07D 413/04* | (2006.01) |
| *C07D 413/06* | (2006.01) |
| *A01N 43/76* | (2006.01) |
| *C07D 263/32* | (2006.01) |
| *C07D 407/06* | (2006.01) |
| *C07D 309/14* | (2006.01) |
| *C07D 493/10* | (2006.01) |
| *C07D 513/04* | (2006.01) |
| *C12R 1/01* | (2006.01) |
| *A01N 43/90* | (2006.01) |
| *C07D 263/34* | (2006.01) |
| *A01N 43/16* | (2006.01) |
| *C12P 17/14* | (2006.01) |
| *A01N 43/86* | (2006.01) |
| *A01N 63/00* | (2006.01) |
| *C12P 17/06* | (2006.01) |

(52) U.S. Cl.
CPC ............. *A01N 63/02* (2013.01); *C12P 17/16* (2013.01); *C07D 498/14* (2013.01); *C07D 413/04* (2013.01); *C07D 413/06* (2013.01); *A01N 43/76* (2013.01); *C07D 263/32* (2013.01); *C07D 407/06* (2013.01); *C07D 309/14* (2013.01); *C07D 493/10* (2013.01); *C07D 513/04* (2013.01); *C12N 1/20* (2013.01); *C12R 1/01* (2013.01); *A01N 43/90* (2013.01); *C07D 263/34* (2013.01); *A01N 43/16* (2013.01); *C12P 17/14* (2013.01); *A01N 43/86* (2013.01); *A01N 63/00* (2013.01); *C12P 17/06* (2013.01)
USPC .................................. 435/252.1; 424/93.4

(58) Field of Classification Search
None
See application file for complete search history.

(56) References Cited

U.S. PATENT DOCUMENTS

| | | | |
|---|---|---|---|
| 4,808,207 | A | 2/1989 | Gotlieb |
| 5,545,542 | A | 8/1996 | Nakajima |
| 5,902,595 | A | 5/1999 | Burklow |
| 6,077,505 | A | 6/2000 | Parke |
| 6,194,194 | B1 | 2/2001 | Molloy |
| 6,384,186 | B2 | 5/2002 | Anke |
| 6,689,357 | B2 | 2/2004 | Casida |
| 7,141,407 | B2 | 11/2006 | Zhang et al. |
| 7,393,812 | B2 | 7/2008 | Gerwick |
| 7,396,665 | B2 | 7/2008 | Ueda |
| 7,923,005 | B2 | 4/2011 | Rao |
| 2003/0082147 | A1 | 5/2003 | Gouge |
| 2004/0071663 | A1 | 4/2004 | Campos |
| 2007/0191228 | A1* | 8/2007 | Li et al. .................. 504/117 |
| 2008/0096879 | A1 | 4/2008 | Koide |
| 2009/0175837 | A1 | 7/2009 | Yuki et al. |
| 2010/0022584 | A1 | 1/2010 | Kenyon |
| 2011/0207604 | A1 | 8/2011 | Asolkar |

FOREIGN PATENT DOCUMENTS

| | | |
|---|---|---|
| JP | 2007-091701 | 4/2007 |
| KR | 2005-0034000 A | 4/2005 |
| KR | 100537389 B1 | 12/2005 |
| WO | WO 97/20857 | 6/1997 |
| WO | WO 01/55143 | 8/2001 |
| WO | WO 01/55398 | 8/2001 |
| WO | WO 2009/049378 | 4/2009 |
| WO | WO 2013/032693 | 3/2013 |

OTHER PUBLICATIONS

U.S. Appl. No. 13/841,963, Huang.
Battu et al., "Development and Validation of RP-HPLC for the Rabeprazole Sodium in Pharmaceutical Formulations and Human Plasma", Asian J. Research Chem. 2(1): 49-51 Jan.-Mar. 2009.
Cordova-Kreylos et al., "Isolation and Characterization of *Burkholderia rinojensis* sp. nov., a Non-Burkholderia cepacia Complex Soil Bacterium with Insecticidal and Miticidal Activities," App. Env. Micro. 79(24):1-10 (2013).

(Continued)

*Primary Examiner* — Allison Ford
*Assistant Examiner* — Michelle F Paguio Frising
(74) *Attorney, Agent, or Firm* — Ying-Horng Liu

(57) ABSTRACT

A species of *Burkholderia* sp with no known pathogenicity to vertebrates but with pesticidal activity (e.g., plants, insects, fungi, weeds and nematodes) is provided. Also provided are natural products derived from a culture of said species and methods of controlling pests using said natural products.

18 Claims, 10 Drawing Sheets

(56) References Cited

OTHER PUBLICATIONS

Grgurina et al., "Novel Cyclic Lipodepsipeptide from *Pseudomonas Syringae* pv. lachrymans Strain 508 and Syringopeptin Antimicrobial Activities", Antimicrobial Agents and Chemotherapy 49: 5037-5045. 2005.
Ueda et al., "FR901228, a Novel Antitumor Bicyclic Depsipeptide Produced by *Chromobacterium violaceum* No. 968," J. Antibiotics 47:301-310. 1994.
Extended European Search Report for EP App. No. 11748040.0 dated Jun. 5, 2013.
International Search Report and Written Opinion for Application No. PCT/US2012/050807 dated Feb. 26, 2013.
Database EMBL Accession No. AF148554, Jun. 7, 2000.
Database EMBL Accession No. AF265235, Jun. 8, 2001.
Database EMBL Accession No. AB092606, Apr. 2, 2003.
Database EMBL Accession No. AJ420880, Nov. 27, 2001.
Database EMBL Accession No. AF175314, Sep. 5, 2000.
Database EMBL Accession No. AM905038, Nov. 20, 2007.
Database EMBL Accession No. AY740337, Oct. 10, 2004.
Database EMBL Accession No. AB212236, Mar. 28, 2006.
Database EMBL Accession No. AB212227, Mar. 28, 2006.
Database EMBL Accession No. AY741345 Oct. 10, 2004.
Database EMBL Accession No. AB508854, Jul. 2, 2009.
Database EMBL Accession No. AY741351, Oct. 10, 2004.
Database EMBL Accession No. AY741349, Oct. 10, 2004.
Database EMBL Accession No. AY740350, Aug. 31, 2005.
Database EMBL Accession No. AY741334, Oct. 10, 2004.
Database EMBL Accession No. AY741348, Oct. 10, 2004.
Database EMBL Accession No. AY741330, Oct. 10, 2004.
Database EMBL Accession No. AY741340, Oct. 10, 2004.
Database EMBL Accession No. AY741339, Oct. 10, 2004.
Database EMBL Accession No. AM747631, Jun. 27, 2007.
Database EMBL Accession No. AY741359, Oct. 10, 2004.
Database EMBL Accession No. AY741341, Oct. 10, 2004.
Database EMBL Accession No. AY741353, Oct. 10, 2004.
Database EMBL Accession No. AM747632, Jun. 21, 2007.
Database EMBL Accession No. AM747628, Jun. 21, 2007.
Database EMBL Accession No. AY661910, Aug. 3, 2004.
Database EMBL Accession No. FJ932759, Jun. 3, 2009.
Database EMBL Accession No. AM747630, Jun. 21, 2007.
Database EMBL Accession No. EU684748, Jun. 8, 2008.
Database EMBL Accession No. AB021369, Jan. 22, 1999.
Database EMBL Accession No. AY741361, Oct. 10, 2004.
Database EMBL Accession No. AY741335, Oct. 10, 2004.
Database EMBL Accession No. AB211225, Apr. 16, 2005.
Database EMBL Accession No. FJ436055, Dec. 29, 2008.
Database EMBL Accession No. DQ273265, Dec. 7, 2005.
Database EMBL Accession No. GQ359110, Aug. 16, 2009.
Database EMBL Accession No. U96927, Jul. 1, 1998.
Database EMBL Accession No. EU826644, Nov. 3, 2008.
Database EMBL Accession No. E10021, Oct. 8, 1997.
Database EMBL Accession No. AB252073, Aug. 29, 2006.
Database EMBL Accession No. U96928, Jul. 1, 1998.
Database EMBL Accession No. EU305400, Jan. 8, 2008.
Database EMBL Accession No. FJ870663, May 10, 2009.
Database EMBL Accession No. AY662003, Aug. 3, 2004.
Database EMBL Accession No. AJ491304, Jun. 17, 2003.
Database EMBL Accession No. U96937, Jul. 1, 1998.
Database EMBL Accession No. U96929, Jul. 1, 1998.
Database EMBL Accession No. FJ606689, Jan. 20, 2009.
Database EMBL Accession No. AY946011, Mar. 26, 2005.
Database EMBL Accession No. EU214612, Jul. 8, 2008.
Database EMBL Accession No. AY946010, Mar. 26, 2005.
Abdel-Mawgoud et al., "Rhamnolipids: Diversity of Structures, Microbial Origins and Roles", Applied Microbiology and Biotechnology 86: 1323-1336. 2010.
Anderson et al., "The Structure of Thiostrepton" Nature 225: 233-235. 1970.
Andra, "Endotoxin-Like Properties of a Rhamnolipid Exotoxin from *Burkholderia* (*Pseudomonas*) Plantarii: Immune Cell Stimulation and Biophysical Characterization" Biol. Chem. 387: 301-310. 2006.
Arena et al., "The Mechanism of Action of Avermectins in *Caenorhabditis elegans*—Correlation Between Activation of Glutamate-Sensitive Chloride Current, Membrane Binding and Biological Activity" J. Parasitol. 81: 286-294. 1995.
Asolkar et al., "Daryamides A-C Weakly Cytotoxic Polyketides from a Marine-Derived Actinomycete of the Genus *Streptomyces* Strain CNQ-085" J. Nat. Prod. 69:1756-1759. 2006.
Battu et al., "Development and Validation of RP-HPLC for the Rabeprazole Sodium in Pharmaceutical Formulations and Human Plasma", Asian J. Research Chem. 2(1 ): 49-51 Jan.-Mar. 2009.
Betti et al., "Molecular Analysis of Two Mutants from Lotus Japonicus Deficient in Plastidic Glutamine Synthetase: Functional Properties of Purified GLN2 Enzymes", Planta 224: 1068-1079. 2006.
Blodget et al., "Molecular Cloning, Sequence Analysis and Heterologous Expression of Phosphinothricin Tripeptide Biosynthetic Gene Cluster from *Streptomyces viridochromogenes* DSM 40736," Antimicrobial Agents and Chemotherapy 49: 230-240. 2005.
Blodget et al., "Biosynthesis of 2-Hydroxyethylphosphonate, an Unexpected Intermediate Common to Multiple Phosphonate Biosynthetic Pathways," J. Biol. Chem. 22:23161-23168. 2008.
Burkhead et al., "Pyrrolnitrin Production by Biological Control Agent *Pseudomonas cepacia* B37w in Culture and in Colonized Wounds of Potatoes", Appl. Environ. Microbiol. 60: 2031-2039. 1994.
Burkholder, "Sour Skin, a Bacterial Rot of Onion Bulbs" Phytopathology 40: 115-117. 1950.
Caballero-Mellado et al., "*Burkholderia unamae* sp. nov., an N2-fixing Rhizospheric and Endophytic Species" Int. J. Syst. Evol. Microbiol. 54: 1165-1172. 2004.
Cain et al., "Synergistic Antimicrobial Activity of Metabolites Produced by a Nonobligate Bacterial Predator," Antimicrobial Agents and Chemotherapy 47: 2113-2117. 2003.
Cashion et al., "A Rapid Method for the Base Ratio Determination of Bacterial DNA" Anal. Biochem. 81: 461-466. 1977.
Castro-Rodriguez et al., "The Glutamine Synthetase Gene Family in Populus", BMC Plant Biology 11:119. 2011.
Chen et al., "*Burkholderia nodosa* Sp. Nov., Isolated from Root Nodules of the Woody Brazilian Legumes Mimosa Bimucronata and *Mimosa scabrella*" Int. J. Syst. Evol. Microbiol. 57: 1055-1059. 2007.
Cheng et al., "Melioidosis: Epidemiology, Pathophysiology, and Management" Clin. Microbiol. Rev. 18: 383-416. 2005.
Coenye et al., "Diversity and Significance of *Burkholderia* Species Occupying Diverse Ecological Niches" Environ. Microbiol. 5: 719-729. 2003.
Compant et al., "Diversity and Occurence of *Burkholderia* spp. In the Natural Environment" FEMS Microbiol. Rev. 32: 607-626. 2008.
De Ley et al., "The Quantitative Measurement of DNA Hybridization from Renaturation Rates" Eur. J. Biochem. 12: 133-142. 1970.
Deng et al., "Structural and Functional Characterization of Diffusible Signal Factor Family Quorum-Sensing Signals Produced by Members of the *Burkholderia cepacia* Complex", Applied and Environmental Microbiology 76: 4675-4683. 2010.
Duke et al., "Natural Products as Sources for Herbicides: Current Status and Future Trends" Weed Res. 40: 99-111. 2000.
El-Banna et al., "Pyrrolnitrin from *Burkholderia cepacia*: Antibiotic Activity Against Fungi and Novel Activities Against Streptomycetes", J. Applied Microbiology 85: 6978. 1998.
Eisenberg et al., "Structure—Function Relationships of Glutamine Synthetases", BBA 1477:122-135. 2000.
Gawronski et al., "Microtiter Assay for Glutamine Synthetase Biosynthetic Activity Using Inorganic Phosphate Detection", Analytical Biochemistry 327: 114-118. 2004.
Gising et al., "Trisubstituted Imidazoles as *Mycobacterium tuberculosis* Glutamine Synthetase Inhibitors", J. Medicinal Chemistry 55: 2894-2898. 2012.

(56) References Cited

OTHER PUBLICATIONS

Grgurina et al., "Novel Cyclic Lipodepsipeptide from *Pseudomonas syringae* pv. lachrymans Strain 508 and Syringopeptin Antimicrobial Activities", Antimicrobial Agents and Chemotherapy, 49:5037-5045. 2005.
Guella et al., "Almazole C, a New Indole Alkaloid Bearing an Unusually 2,5-disubstituted Oxazole Moiety and its Putative Biogenetic Precursors, from a Senegalese Delesseriacean Seaweed" Helv. Chim. Acta 77: 1999-2006. 1994.
Guella et al. "Isolation, Synthesis and Photochemical Properties of Almazolone, a New Indole Alkaloid from a Red Alga of Senegal." Tetrahedron. 62: 1165-1170. 2006.
Harth et al., "An Inhibitor of Exported *Mycobacterium tuberculosis* Glutamine Synthetase Selectively Blocks the Growth of Pathogenic Mycobacteria in Axenic Culture and in Human Monocytes: Extracellular Proteins as Potential Novel Drug Targets", J. Exp. Med., 189: 1425-1435. 1999.
Harth et al., "Treatment of *Mycobacterium tuberculosis* with Antisense Oligonucleotides to Glutamine Synthetase mRNA Inhibits Glutamine Synthetase Activity, Formation of the Poly-L-Glutamate/Glutamine Cell Wall Structure, and Bacterial Replication", Proc Natl Acad Sci U S A 97:418-423. 2000.
Henderson et al., "Bongkrekic Acid. An Inhibitor of the Adenine Nucleotide Translocase of Mitochondria" J. Biol. Chem. 245: 1319-1326. 1970.
Hirota et al., "Isolation of Indolmycin and its Derivatives as Antagonists of L-Tryptophan" Agri. Biol. Chem. 42: 147-151. 1978.
Holmes et al., "Agricultural Use of *Burkholderia* (*Pseudomonas*) Cepacia: A Threat to Human Health?", Emerging Infectious Diseases 4: 221-227. 1998.
Hu et al., "Biocidal Activity in Plant Pathogenic Acidovorax, Burkholderia, Herbaspirillum, *Ralstonia*, and *Xanthomonas* spp" J. Appl. Microbiol. 84: 263-271. 1998.
Huss et al., "Studies on the Spectrophotometric Determination of DNA Hybridization from Renaturation Rates" System. Appl. Microbiol. 4: 184-192. 1983.
Janisiewicz et al., "Biological Control of Blue Mold and Gray Mold on Apple and Pear with *Pseudomonas cepacia*" Phytopathology 78: 1697-1700. 1988.
Jansen et al., "Thiangazole: a Novel Inhibitor of HIV-1 from Polyangium Spec" Liebigs Ann. Chem. 4: 357-3359. 1992.
Jeong et al., "Toxoflavin Produced by *Burkholderia* glumae Causing Rice Grain Rot is Responsible for Inducing Bacterial Wilt in Many Field Crops" Plant Disease 87: 890-895. 2003.
Keum et al., "Effects of Nutrients on Quorum Signals and Secondary Metabolite Productions of *Burkholderia* sp O33," J. Microbiology and Biotechnology 19: 1142-1149. 2009.
Knudsen et al., "Field Persistence and Efficacy of Five Bacterial Preparations for Control of Peanut Leaf Spot" Plant Disease 71: 442-445. 1987.
Koga-Ban et al., "cDNA Sequences of Three Kinds of Beta-Tubulins from Rice" DNA Res. 2: 21-26. 1995.
Koyama et al., "Isolation, Characterization, and Synthesis of Pimprinine, Pimprinethine, and Pimprinaphine, Metabolites of Streptoverticillium Olivoreticuli" Agri. Biol. Chem. 45: 1285-1287. 1981.
Krieg et al., "*Bacillus thuringiensis* Var. Tenebrionis: Ein Neuer, Gegenuber Larven von Coleopteren Wirksamer Pathotyp" Z. Angew. Entomol. 96: 500-508. 1983.
Kunze et al., "Thiangazole, a New Thiazoline Antibiotic from Polyangium sp (Myxobacteria): Production, Antimicrobial Activity and Mechanism of Action" J. Antibiot. 46: 1752-1755. 1993.
Lamichhane et al., "Essential Metabolites of *Mycobacterium tuberculosis* and their Mimics". mBio 2(1): e00301-10.doi:10.1128/mBio.00301-10. 2011.
Larossa et al., "The Sulfonylurea Herbicide Sulfometuron Methyl is an Extremely Potent and Selective Inhibitor of Acetolactate Synthase in *Salmonella typhimurium*", Journal of Biological Chemistry, 259: 8753-8757. 1984.

Lea et al., "The Action of 2-Amino-4-(Methylphosphinyl)-Butanoic Acid (Phosphinothricin) and its 2-Oxo-Derivative on the Metabolism of Cyanobacteria and Higher Plants", Phytochemistry 23: 1-6. 1984.
Lee et al., "Cepacidine A, a Novel Antifungal Antibiotic Produced by *Pseudomonas cepacia*. 1. Taxonomy, Production, Isolation and Biological Activity", J. Antibiotics 47: 1402-1405. 1994.
Leahy et al., "Comparison of Factors Influencing Trichloroethylene Degradation by Toluene-Oxidizing Bacteria" Appl. Environ. Microbiol. 62: 825-833. 1996.
Lessie et al., "Genomic Complexity and Plasticity of *Burkholderia cepacia*" FEMS Microbiol. Lett. 144: 117-128. 1996.
Lindquist et al., "Isolation and Structure Determination of Diazonamides A and B, Unusual Cytotoxic Metabolites from the Marine Ascidian Diazona Chinensis" J. Am. Chem. Soc. 113: 2303-2304. 1991.
Lorch et al., "Basic Methods for Counting Microoganisms in Soil and Water," in *Methods in Applied Soil Microbiology and Biochemistry*. K. Alef and P. Nannipieri. Eds. San Diego, CA, Academic Press: pp. 146-161. 1995.
Lydon et al., "Inhibitors of Glutamine Biosynthesis", in *Plant Amino Acids: Biochemistry and Biotechnology*. B. Singh, Ed. New York, USA, Marcel Decker. 445-464. 1999.
Mahenthiralingam et al., "DNA-Based Diagnostic Approaches for Identification of *Burkholderia cepacia* Complex, *Burkholderia vietnamiensis, Burkholderia multivorans, Burkholderia stabilis*, and *Burkholderia cepacia* Genomovars I and III" J. Clin. Microbiol. 38: 3165-3173. 2000.
Mao et al., "Isolation and Characterization of Antifungal Substances from *Burkholderia* sp Culture Broth", Current Microbiology, 53: 358-364. 2006.
Meyers et al., "Xylocandin: A New Complex of Antifungal Peptides. 1.Taxonomy, Isolation and Biological Activity", J. Antibiotics, 40: 1515-1519. 1987.
Ming et al., "Metal Binding and Structure-Activity Relationship of the Metalloantibiotic Peptide Bacitracin" J. Inorganic Biochemistry 91: 46-58. 2002.
Moon et al., "Plant Growth Promoting and Fungicidal 4-Quinolinones from *Pseudomonas cepacia*", Phytochemistry, 42: 365-368. 1996.
Morita et al., "Biological Activity of Tropolone" Biol. Pharm. Bull. 26: 1487-1490. 2003.
Nagamatsu, "Syntheses, Transformation, and Biological Activities of 7-Azapteridine Antibiotics: Toxoflavin, Fervenulin, Reumycin and their Analogs" Recent Res. Devel. Org. Bioorg. Chem. 4: 97-121. 2001.
Naik, et al., "Pimprinine, an Extracellular Alkaloid Produced by *Streptomyces* Cdril-312: Fermentation, Isolation and Pharmacological Activity" J. Biotech. 88: 1-10. 2001.
Nakajima et al., "Hydantocidin: a New Compound with Herbicidal Activity" J. Antibiot. 44: 293-300. 1991.
Nakajima et al., "New Antitumor Substances, FR901463, FR901464 and FR901465. I. Taxonomy, Fermentation, Isolation, Physico-Chemical Properties and Biological Activities" J. Antibiot. 49: 1196-1203. 1996.
Nakajima et al., "New Antitumor Substances, FR901463, FR901464 and FR901465. II. Activities Against Experimental Tumors in Mice and Mechanism of Action" J. Antibiot. 49: 1204-1211. 1996.
N'Diaye et al., "Almazole A and Almazole B, Unusual Marine Alkaloids of an Unidentified Red Seaweed of the Family Delesseriaceae from the Coasts of Senegal" Tet. Lett. 35: 4827-4830. 1994.
N'Diaye et al., "Almazole D, a New Type of Antibacterial 2,5-Disubstituted Oxazolic Dipeptide from a Red Alga of the Coast of Senegal" Tet. Lett. 37: 3049-3050. 1996.
Nierman et al., "Structural Flexibility in the *Burkholderia mallei* Genome" Proc. Natl. Acad. Sci. USA 101: 14246-14251. 2004.
Okazaki et al., "Rhizobial Strategies to Enhance Symbiotic Interaction: Rhizobitoxine and 1-Aminocyclopropane-1-Carboxylate Deaminase" Microbes Environ. 19: 99-111. 2004.
Parke et al., "Diversity of the *Burkholderia cepacia* Complex and Implications for Risk Assessment of Biological Control Strains" Annu. Rev. in Phytopathology 39: 225-258. 2001.

(56) References Cited

OTHER PUBLICATIONS

Partida-Martinez et al., "A Gene Cluster Encoding Rhizoxin Biosynthesis in 'Burkholderia rhizoxina,' the Bacterial Endosymbiont of the Fungus Rhizopus Microsporus", ChemBioChem, 8: 41-45. 2007.
Petit et al. "Isolation of Labradorins 1 and 2 from Pseudomonas Syringae pv. corona faciens" J. Nat. Prod. 65: 1793-1797. 2002.
Pitt et al., "Type Characterization and Antibiotic Susceptibility of Burkholderia (Pseudomonas) Cepacia Isolates from Patients with Cystic Fibrosis in the United Kingdom and the Republic of Ireland" J. Med. Microbiol. 44: 203-210. 1996.
Ramette et al., "Species Abundance and Diversity of Burkholderia cepacia Complex in the Environment" Appl. Environ. Microbiol. 71: 1193-1201. 2005.
Reis et al., "Burkholderia tropica sp. nov., a Novel Nitrogen-Fixing, Plant-Associated Bacterium" Int. J. Syst. Evol. Microbiol. 54: 2155-2162. 2004.
Salama et al., "Potency of Spore-γ-Endotoxin Complexes of Bacillus thuringiensis Against Some Cotton Pests" Z. Angew. Entomol. 91: 388-398. 1981.
Selva et al., "Targeted Screening for Elongation Factor Tu Binding Antibiotics" J. Antibiot. 50: 22-26. 1997.
Selvakumar et al., "Production and Bioassay of Bialaphos Biosynthesized by Streptomyces hydroscopicus NRRL B-16256," Bioprocess Engineering 20:459-462. 1999.
Shao et al., "Biosynthesis of 2-Hydroxyethylphosphate, an Unexpected Intermediate Common to Multiple Phosphonate Biosynthetic Pathways," J. Biol. Chem. 283:23161-23168. 2008.
Shoji et al., "Isolation of Cepafungins I, II and III from Pseudomonas Species", J. Antibiotics, 43, 783-787. 1990.
Singh et al., "Development of a Simple Assay Protocol for High-Throughput Screening of Mycobacterium tuberculosis Glutamine Synthetase for the Identification of Novel Inhibitors", Journal of Biomolecular Screening, 10(7): 725-729. 2005.
Singh et al., "Development of a Simple High-Throughput Screening Protocol Based on Biosynthetic Activity of Mycobacterium Tuberculosis Glutamine Synthetase for the Identification of Novel Inhibitors", J Biomol Screen11: 10351042. 2006.
Spilker et al., "PCR-Based Assay for Differentiation of Pseudomonas aeruginosa from other Pseudomonas Species Recovered From Cystic Fibrosis Patients" J. Clin. Microbiol. 42: 2074-2079. 2004.
Stead et al., "Induction of Phenazine Biosynthesis in Cultures of Pseudomonas aeruginosa by L-N-(3-oxohexanoyl) Homoserine Lactone" FEMS Microbio. Letters 140:15-22. 1996.
Sultan et al., "Novel Oxidized Derivatives of Antifungal Pyrrolnitrin from the Bacterium Burkholderia cepacia K87," J. Antibiotics 61: 420-425. 2008.
Tachibana et al., "Inhibition of Glutamine Synthetase and Quantitative Changes of Free Amino Acids in Shoots of Bialaphos Treated Japanese Barnyard Millet", J. Pesticide Science, 11:27-31. 1986.
Takahashi et al., "Martefragin A, a Novel Indole Alkaloid Isolated from a Red Alga, Inhibits Lipid Peroxidation" Chem Pharm. Bull. 46: 1527-1529. 1998.
Takita et al., "Chemistry of Bleomycin. XIX Revised Structures of Bleomycin and Phleomycin" J. Antibiot. 31: 801-804. 1978.
Thompson et al., "Spinosad—A Case Study: An Example from a Natural Products Discovery Programme" Pest Management Sci. 56: 696-702. 2000.
Tran Van et al., "Repeated Beneficial Effects of Rice Inoculation with a Strain of Burkholderia vietnamiensis on Early and Late Yield Component in Low Fertility Sulphate Acid Soils of Vietnam" Plant and Soil 218: 273-284. 2000.
Tsuruo et al., "Rhizoxin, a Macrocyclic Lactone Antibiotic, as a New Antitumor Agent Against Human and Murine Tumor Cells and their Vincristine-Resistant Sublines" Cancer Res. 46: 381-385. 1986.
Umehara et al., "Studies of New Antiplatelet Agents WS-30581 A and B" J. Antibiot. 37: 1153-1160. 1984.
Vandamme et al. "Polyphasic Taxonomic Study of the Emended Genus Arcobacter with Arcobacter butzleri comb. nov. and Arcobacter skirrowii sp. nov., an Aerotolerant Bacterium Isolated from Veterinary Specimens" Int. J. Syst. Bacteriol. 42: 344-356. 1992.
Vanderwall et al., "A Model of the Structure of HOO-Co Bleomycin Bound to d(CCAGTACTGG): Recognition at the d(GpT)site and Implications for Double-Stranded DNA Cleavage" Chem. Biol. 4: 373-387. 1997.
Vencill et al., "Herbicide Resistance: Toward an Understanding of Resistance Development and the Impact of Herbicide-Resistant Crops", Weed Science. 60: 2-30. 2012.
Vermis et al. "Evaluation of Species-Specific RecA-Based PCR Tests for Genomovar Level Identification Within the Burkholderia cepacia Complex" J. Med. Microbiol. 51: 937-940. 2002.
Vial et al., "Burkholderia Diversity and Versatility: An Inventory of the Extracellular Products", J. Microbiol. Biotechnol. 17:9. 1407-1429. 2007.
Watanabe et al, "A New Antibiotic SF2583A, 4-Chloro-5-(3'indoly)oxazole, Produced by Streptomyces" Meiji Seika Kenkyu Nenpo 27: 55-62. 1988.
Wayne et al., "Report of the Ad Hoc Committee on Reconciliation of Approaches to Bacterial Systematics" Int. J. Syst. Bacteriology. 37: 463-464. 1987.
Werner et al., "Uptake of Indolmycin in Gram-positive Bacteria." Antimicrob. Agents Chemotherapy 18: 858-862. 1980.
Wilson et al., "Toxicity of Rhizonin A, Isolated from Rhizopus microsporus, in Laboratory Animals" Food Chem. Toxicol. 22: 275-281. 1984.
Zeck, "A Rating System for Field Evaluation of Root-Knot Nematode Infestations," Pflanzenschutz-Nachrichten Bayer 24,1: 141-144. 1971.
Zhou et al., "Antimicrobial Susceptibility and Synergy Studies of Burkholderia cepacia Complex Isolated From Patients with Cystic Fibrosis" Antimicrob. Agents and Chemotherapy 51: 1085-1088. 2007.
International Search Report and Written Opinion for Application No. PCT/US2011/026016 dated Jan. 18, 2012.
International Preliminary Report on Patentability for Application No. PCT/US2011/0260126 dated Aug. 28, 2012.
Burkholderia andropogonis: Psuedomonas woodsii ,CW00B006C (ATCC PTA-4234) accessed from http://www.atcc.org/Products/All/PTA-4234 on Mar. 12, 2014.
International Search Report and Written Opinion for Application No. PCT/US2014/015799 dated May 27, 2014.
Schweizer, et al., "Mechanisms of antibiotic resistance in Burkholderia pseudomallei: implications for treatment of melioidosis", Future Microbiolo., Dec. 2012, vol. 7. No. 12, pp. 1389-1399.
Stokell, et al., Rapid emergence of a ceftazidime-resistant Burkholderia multivorans strain in a cystic fibrosis patient, J. Cyst. Fibros., Mar. 9, 2013. vol. 12 No. 6, pp. 812-816.

\* cited by examiner

*UTC (back)*
*A396 @ 5 mg/mL (middle)*
*A396 @ 10 mg/mL (front)*

US 8,822,193 B2

ISOLATED BACTERIAL STRAIN OF THE GENUS *BURKHOLDERIA* AND PESTICIDAL METABOLITES THEREFROM

PRIORITY CLAIM

This application is a continuation-in-part of application Ser. No. 13/034,575, filed Feb. 24, 2011, the contents of which are incorporated herein by reference. Application Ser. No. 13/034,575 claims priority to U.S. application Ser. No. 61/308,287, filed Feb. 25, 2010 and priority to application Ser. No. 61/406,541, filed Oct. 25, 2010 under 35 U.S.C. 119(e). The contents of U.S. application Ser. No. 61/308,287, filed Feb. 25, 2010 and U.S. application Ser. No. 61/406,541, filed Oct. 25, 2010 are herein incorporated by reference

SEQUENCE LISTING

The instant application contains a Sequence Listing which has been submitted in ASCII format via EFS-Web and is hereby incorporated by reference in its entirety. Said ASCII copy, is named MOI-42016-CIP1-SEQ.txt and is 49 kB in size.

TECHNICAL FIELD

Provided herein is a species of *Burkholderia* sp with no known pathogenicity to vertebrates, such as mammals, fish and birds but pesticidal activity against plants, insects, fungi and nematodes. Also provided are natural products derived from a culture of said species and methods of controlling germination and growth of dicotyledenous, monocotyledonous and sedge weeds, modulating growth of fungi and controlling pests such as insects and nematodes using said natural products.

BACKGROUND

Natural products are substances produced by microbes, plants, and other organisms. Microbial natural products offer an abundant source of chemical diversity, and there is a long history of utilizing natural products for pharmaceutical purposes. One such compound is FR901228 isolated from *Chromobacterium* and has been found to be useful as an antibacterial agent and antitumor agent (see, for example, Ueda et al., U.S. Pat. No. 7,396,665).

However, secondary metabolites produced by microbes have also been successfully found to have uses for weed and pest control in agricultural applications (see, for example, Nakajima et al. 1991; Duke et al., 2000; Lydon & Duke, 1999; Gerwick et al., U.S. Pat. No. 7,393,812). Microbial natural products have been also successfully developed into agricultural insecticides (see, for example, Salama et al. 1981; Thompson et al., 2000; Krieg et al. 1983). Sometimes, such natural products have been combined with chemical pesticides (see, for example, Gottlieb, U.S. Pat. No. 4,808,207).

*Burkholderia*

The *Burkholderia* genus, β-subdivision of the proteobacteria, comprises more than 40 species that inhabit diverse ecological niches (Compant et al., 2008). The bacterial species in the genus *Burkholderia* are ubiquitous organisms in soil and rhizosphere (Coenye and Vandamme, 2003; Parke and Gurian-Sherman, 2001). Traditionally, they have been known as plant pathogens, *B. cepacia* being the first one discovered and identified as the pathogen causing disease in onions (Burkholder, 1950). Several *Burkholderia* species have developed beneficial interactions with their plant hosts (see, for example, Cabballero-Mellado et al., 2004, Chen et al., 2007). Some *Burkholderia* species have also been found to be opportunistic human pathogens (see, for example, Cheng and Currie, 2005 and Nierman et al., 2004). Additionally, some *Burkholderia* species have been found to have potential as biocontrol products (see for example, Burkhead et al., 1994; Knudsen et al., 1987; Jansiewicz et al., 1988; Gouge et al., US Patent Application No. 2003/0082147; Parke et al., U.S. Pat. No. 6,077,505; Casida et al., U.S. Pat. No. 6,689,357; Jeddeloh et al., WO2001055398; Zhang et al., U.S. Pat. No. 7,141,407). Some species of in this genus have been effective in bioremediation to decontaminate polluted soil or groundwater (see, for example, Leahy et al. 1996). Further, some *Burkholderia* species have been found to secrete a variety of extracellular enzymes with proteolytic, lipolytic and hemolytic activities, as well as toxins, antibiotics, and siderophores (see, for example, Ludovic et al., 2007; Nagamatsu, 2001).

Oxazoles, Thiazoles and Indoles

Oxazoles, thiazoles and indoles are widely distributed in plants, algae, sponges, and microorganisms. A large number of natural products contain one or more of the five-membered oxazole, thiazole and indole nucleus/moieties. These natural products exhibit a broad spectrum of biological activity of demonstrable therapeutic value. For example, bleomycin A (Tomohisa et al.), a widely prescribed anticancer drug, effects the oxidative degradation of DNA and uses a bithiazole moiety to bind its target DNA sequences (Vanderwall et al., 1997). Bacitracin (Ming et al., 2002), a thiazoline-containing peptide antibiotic, interdicts bacterial cell wall new biosynthesis by complexation with C55-bactoprenolpyrophosphate. Thiangazole (Kunze et al., 1993) contains a tandem array of one oxazole and three thiazolines and exhibits antiviral activity (Jansen et al., 1992). Yet other oxazole/thiazole-containing natural products such as thiostrepton (Anderson et al., 1970) and GE2270A (Selva et al., 1997) inhibit translation steps in bacterial protein synthesis. More than 1000 alkaloids with the indole skeleton have been reported from microorganisms. One-third of these compounds are peptides with masses beyond 500 Da where the indole is tryptophan derived. The structural variety of the remaining two-thirds is higher, and their biological activity seems to cover a broader range, including antimicrobial, antiviral, cytotoxic, insecticidal, antithrombotic, or enzyme inhibitory activity.

BRIEF SUMMARY

Provided herein is an isolated strain of a non-*Burkholderia cepacia*, non-*Burkholderia plantari*, non-*Burkholderia gladioli*, *Burkholderia* sp. which has the following characteristics:

a. Has a 16S rRNA gene sequence comprising a forward sequences having at least 99.0% identity to the sequences set forth in SEQ ID NO:8, 11 and 12 and a reverse sequence having at least 99.0% identity to SEQ ID NO:9, 10, 13-15;

b. Has pesticidal, in particular, herbicidal, insecticidal, fungicidal and nematicidal activity;

c. Produces at least one of the compounds selected from the group consisting of:

(i) a compound having the following properties: (a) a molecular weight of about 525-555 as determined by Liquid Chromatography/Mass Spectroscopy (LC/MS); (b) $^1H$ NMR values of 6.22, 5.81, 5.69, 5.66, 5.65, 4.64, 4.31, 3.93, 3.22, 3.21, 3.15, 3.10, 2.69, 2.62, 2.26, 2.23, 1.74, 1.15, 1.12, 1.05, 1.02; (c) has $^{13}C$ NMR values of 172.99, 172.93, 169.57, 169.23, 167.59, 130.74, 130.12, 129.93, 128.32, 73.49, 62.95, 59.42, 57.73, 38.39, 38.00, 35.49, 30.90, 30.36, 29.26, 18.59, 18.38, 18.09, 17.93, 12.51 and (c) an High Pressure Liquid Chromatography (HPLC) retention time of about 10-15 minutes, on a reversed phase C-18 HPLC column using a water:acetonitrile ($CH_3CN$) gradient;

(ii) a compound having an oxazolyl-indole structure comprising at least one indole moiety, at least one oxazole moiety, at least one substituted alkyl group and at least one carboxylic ester group; at least 17 carbons and at least 3 oxygen and 2 nitrogens;

(iii) a compound having an oxazolyl-benzyl structure comprising at least one benzyl moiety, at least one oxazole moiety, at least one substituted alkyl group and at least one amide group; at least 15 carbons and at least 2 oxygen and 2 nitrogens;

(iv) a compound having at least one ester, at least one amide, at least three methylene groups, at least one tetrahydropyranose moiety and at least three olefinic double bonds, at least six methyl groups, at least three hydroxyl groups, at least twenty five carbons and at least eight oxygen and one nitrogen and d. is non-pathogenic (non-infectious) to vertebrate animals, such as mammals, birds and fish;

e. is susceptible to kanamycin, chloramphenicol, ciprofloxacin, piperacillin, imipenem, and a combination of sulphamethoxazole and trimethoprim and f. contains the fatty acids 16:0, cyclo 17:0, 16:0 3-OH, 14:0, cyclo 19:0 ω8c, 18:0.

In a particular embodiment, the strain has the identifying characteristics of a *Burkholderia* A396 strain (NRRL Accession No. B-50319).

Disclosed herein are isolated compounds which are optionally obtainable or derived from *Burkholderia* species, or alternatively, organisms capable of producing these compounds that can be used to control various pests, particularly plant phytopathogenic pests, examples of which include but are not limited to insects, nematodes, bacteria, fungi. These compounds may also be used as herbicides.

In particular, the isolated pesticidal compounds may include but are not limited to:

(A) a compound having the following properties: (i) a molecular weight of about 525-555 as determined by Liquid Chromatography/Mass Spectroscopy (LC/MS); (ii) $^1$H NMR δ values of 6.22, 5.81, 5.69, 5.66, 5.65, 4.64, 4.31, 3.93, 3.22, 3.21, 3.15, 3.10, 2.69, 2.62, 2.26, 2.23, 1.74, 1.15, 1.12, 1.05, 1.02; (iii) has $^{13}$C NMR δ values of 172.99, 172.93, 169.57, 169.23, 167.59, 130.74, 130.12, 129.93, 128.32, 73.49, 62.95, 59.42, 57.73, 38.39, 38.00, 35.49, 30.90, 30.36, 29.26, 18.59, 18.38, 18.09, 17.93, 12.51 and (iv) an High Pressure Liquid Chromatography (HPLC) retention time of about 10-15 minutes, on a reversed phase C-18 HPLC column using a water:acetonitrile ($CH_3CN$) gradient;

(B) a compound having an oxazolyl-indole structure comprising at least one indole moiety, at least one oxazole moiety, at least one substituted alkyl group and at least one carboxylic ester group; at least 17 carbons and at least 3 oxygen and 2 nitrogens;

(C) a compound having an oxazolyl-benzyl structure comprising at least one benzyl moiety, at least one oxazole moiety, at least one substituted alkyl group and at least one amide group; at least 15 carbons and at least 2 oxygen and 2 nitrogens;

(D) a compound having at least one ester, at least one amide, at least three methylene groups, at least one tetrahydropyranose moiety and at least three olefinic double bonds, at least six methyl groups, at least three hydroxyl groups, at least twenty five carbons and at least eight oxygen and one nitrogen and (E) a compound having at least one ester, at least one amide, an epoxide methylene group, at least one tetrahydropyranose moiety, at least three olefinic double bonds, at least six methyl groups, at least three hydroxyl groups, at least 25 carbons, at least 8 oxygens and at least 1 nitrogen.

In a particular embodiment, the isolated compounds may include but are not limited to:

(A) a compound having an oxazolyl-indole structure comprising at least one indole moiety, at least one oxazole moiety, at least one substituted alkyl group, at least one carboxylic ester group, at least 17 carbons, at least 3 oxygens and at least 2 nitrogens; and which has at least one of the following: (i) a molecular weight of about 275-435; (ii) $^1$H NMR δ values at 8.44, 8.74, 8.19, 7.47, 7.31, 3.98, 2.82, 2.33, 1.08; (iii) $^{13}$C NMR δ values of δ 163.7, 161.2, 154.8, 136.1, 129.4, 125.4, 123.5, 123.3, 121.8, 121.5, 111.8, 104.7, 52.2, 37.3, 28.1, 22.7, 22.7; (iv) an High Pressure Liquid Chromatography (HPLC) retention time of about 10-20 minutes on a reversed phase C-18 HPLC column using a water:acetonitrile ($CH_3CN$) with a gradient solvent system and UV detection of 210 nm; (v) UV absorption bands at about 226, 275, 327 nm;

(B) a compound having an oxazolyl-benzyl structure comprising at least one benzyl moiety, at least one oxazole moiety, at least one substituted alkyl group and at least one amide group; at least 15 carbons and at least 2 oxygens, at least 2 nitrogens; and at least one of the following characteristics: (i) a molecular weight of about 240-290 as determined by Liquid Chromatography/Mass Spectroscopy (LC/MS); (ii) $^1$H NMR δ values at about 7.08, 7.06, 6.75, 3.75, 2.56, 2.15, 0.93, 0.93; (iii) $^{13}$C NMR δ values of 158.2, 156.3, 155.5, 132.6, 129.5, 129.5, 127.3, 121.8, 115.2, 115.2, 41.2, 35.3, 26.7, 21.5, 21.5; (iv) a High Pressure Liquid Chromatography (HPLC) retention time of about 6-15 minutes, on a reversed phase C-18 HPLC column using a water:acetonitrile ($CH_3CN$) gradient and (v) UV absorption bands at about 230, 285, 323 nm;

(C) a non-epoxide compound comprising at least one ester, at least one amide, at least three methylene groups, at least one tetrahydropyranose moiety and at least three olefinic double bonds, at least six methyl groups, at least three hydroxyl groups, at least twenty five carbons, at least eight oxygens and one nitrogen and at least one of the following characteristics: (i) a molecular weight of about 530-580 as determined by Liquid Chromatography/Mass Spectroscopy (LC/MS); (ii) $^1$H NMR δ values of 6.40, 6.39, 6.00, 5.97, 5.67, 5.54, 4.33, 3.77, 3.73, 3.70, 3.59, 3.47, 3.41, 2.44, 2.35, 2.26, 1.97, 1.81, 1.76, 1.42, 1.37, 1.16, 1.12, 1.04; (iii) $^{13}$C NMR δ values of 173.92, 166.06, 145.06, 138.76, 135.71, 129.99, 126.20, 123.35, 99.75, 82.20, 78.22, 76.69, 71.23, 70.79, 70.48, 69.84, 60.98, 48.84, 36.89, 33.09, 30.63, 28.55, 25.88, 20.37, 18.11, 14.90, 12.81, 9.41; (iv) a High Pressure Liquid Chromatography (HPLC) retention time of about 7-12 minutes, on a reversed phase C-18 HPLC column using a water:acetonitrile ($CH_3CN$) with a gradient solvent system and UV detection of 210 nm; (v) a molecular formula of $C_{28}H_{45}NO_{10}$ which was determined by interpretation of the ESIMS and NMR data analysis; (vi) UV absorption bands between about 210-450 nm;

(D) a compound comprising (i) at least one ester, at least one amide, an epoxide methylene group, at least one tetrahydropyranose moiety and at least three olefinic double bonds, at least six methyl groups, at least three hydroxyl groups, at least 25 carbons, at least 8 oxygens and at least 1 nitrogen, (ii) $^{13}$C NMR δ values of 174.03, 166.12, 143.63, 137.50, 134.39, 128.70, 126.68, 124.41, 98.09, 80.75, 76.84, 75.23, 69.87, 69.08, 68.69, 68.60, 48.83, 41.07, 35.45, 31.67, 29.19, 27.12, 24.55, 19.20, 18.95, 13.48, 11.39, 8.04, (iii) a molecular formula of $C_{28}H_{43}NO_9$ and at least one of: (i) $^1H$ NMR δ values at about 6.41, 6.40, 6.01, 5.97, 5.67, 5.55, 4.33, 3.77, 3.75, 3.72, 3.64, 3.59, 3.54, 3.52, 2.44, 2.34, 2.25, 1.96, 1.81, 1.76, 1.42, 1.38, 1.17, 1.12, 1.04; (ii) an High Pressure Liquid Chromatography (HPLC) retention time of about 6-15 minutes, on a reversed phase C-18 HPLC column using a water:acetonitrile ($CH_3CN$) gradient; (iii) UV absorption band between about 210-450 nm and most particularly at about 234 nm.

In a more particular embodiment, provided are compounds including but not limited to:

(A) a compound having the structure ##STR001##

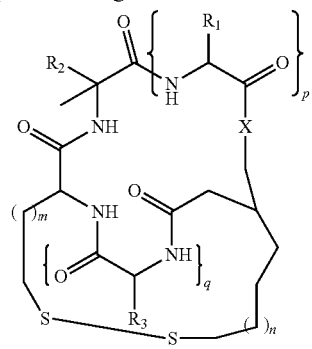

or a pesticidally acceptable salt or steriosomers thereof, wherein M is 1, 2, 3 or 4; n is 0, 1, 2, or 3; p and q are independently 1 or 2; X is O, NH or NR; R1, R2 and R3 are the same or different and independently an amino acid side-chain moiety or an amino acid side-chain derivative and R is a lower chain alkyl, aryl or arylalkyl moiety;

(B) a compound having the structure ##STR002##

STR002##

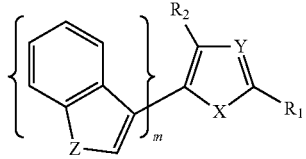

wherein X, Y and Z are each independently —O, —$NR_1$, or —S, wherein $R_1$ is —H or $C_1$-$C_{10}$ alkyl; $R_1$, $R_2$ and m are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl and "m" may be located anywhere on the oxazole ring;

(C) a compound having the structure ##STR002a##

STR002a##

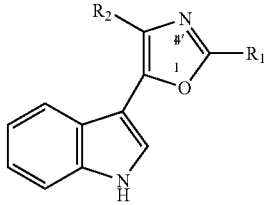

wherein $R_1$ is —H or $C_1$-$C_{10}$ alkyl; $R_2$ is an alkyl ester;

(D) a compound having the structure ##STR003##

STR003##

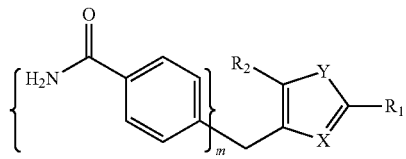

wherein: X and Y are each independently —OH, —$NR_1$, or —S, wherein $R_1$ is —H or $C_1$-$C_{10}$ alkyl; $R_1$, $R_2$ and m, a substituent on the oxazole ring, are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;

(E) a compound having the structure ##STR003a##

STR003a##

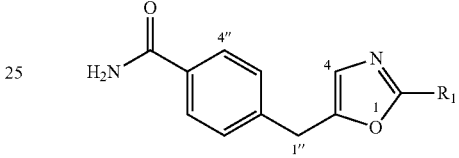

wherein $R_1$ is —H or $C_1$-$C_{10}$ alkyl;

(F) a compound having the structure ##STR004a##

STR004a##

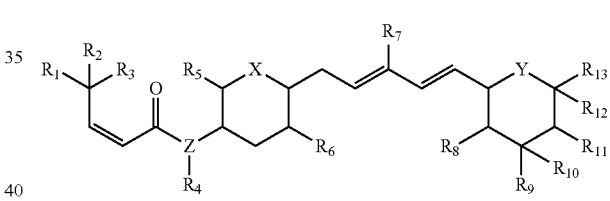

Wherein X, Y and Z are each independently —O, —NR, or —S, wherein R is H or $C_1$-$C_{10}$ alkyl; $R_1$, $R_2$, $R_3$, $R_4$, $R_5$, $R_6$, $R_7$, $R_8$, $R_9$, $R_{10}$, $R_{11}$, $R_{12}$, and $R_{13}$ are each independently H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl.

(G) a compound having the structure ##STR004b##

STR004b##

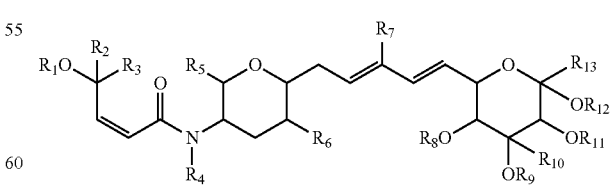

wherein $R_1$, $R_2$, $R_3$, $R_4$, $R_5$, $R_6$, $R_7$, $R_8$, $R_9$, $R_{10}$, $R_{11}$, $R_{12}$, and $R_{13}$ are each independently H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;

(H) a compound having the structure ##STR004c##

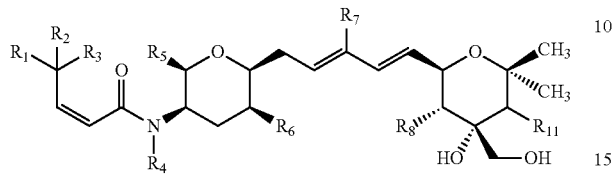

wherein $R_1$, $R_2$, $R_3$, $R_4$, $R_5$, $R_6$, $R_7$, $R_8$, $R_{11}$, are each independently H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;

(I) a compound having the structure ##STR005##

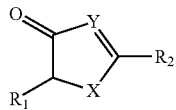

wherein X and Y are each independently —OH, —$NR_1$, or —S, wherein $R_1$, $R_2$ are each independently —H, alkyl (e.g., $C_1$-$C_{10}$ alkyl), substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;

(J) a compound having the structure ##STR006a##

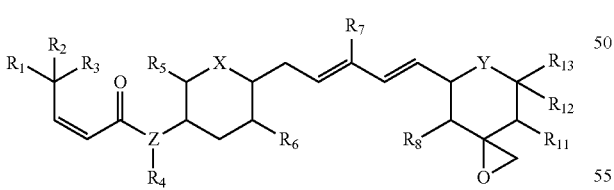

Wherein X, Y and Z are each independently —O, —NR, or —S, wherein R is H or $C_1$-$C_{10}$ alkyl; $R_1$, $R_2$, $R_3$, $R_4$, $R_5$, $R_6$, $R_7$, $R_8$, $R_{11}$, $R_{12}$, and $R_{13}$ are each independently H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl.

In a most particular embodiment, the compounds may include but are not limited to
(i) templazole A;
(ii) templazole B;
(iii) templamide A;
(iv) templamide B;
(v) FR90128;

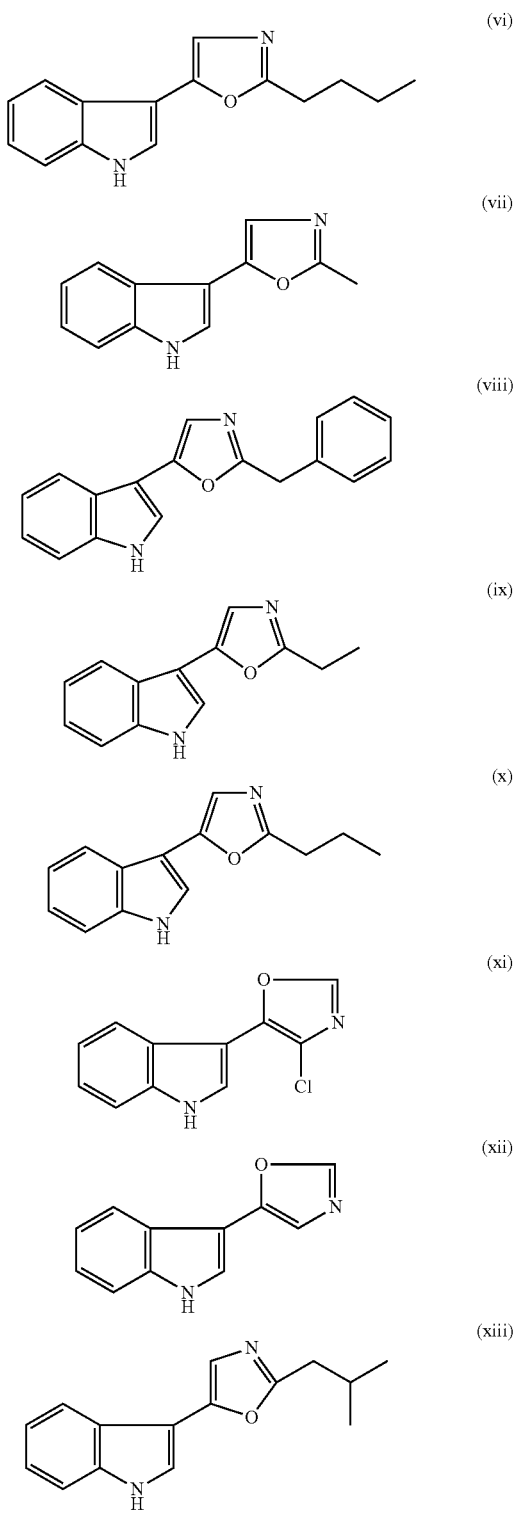

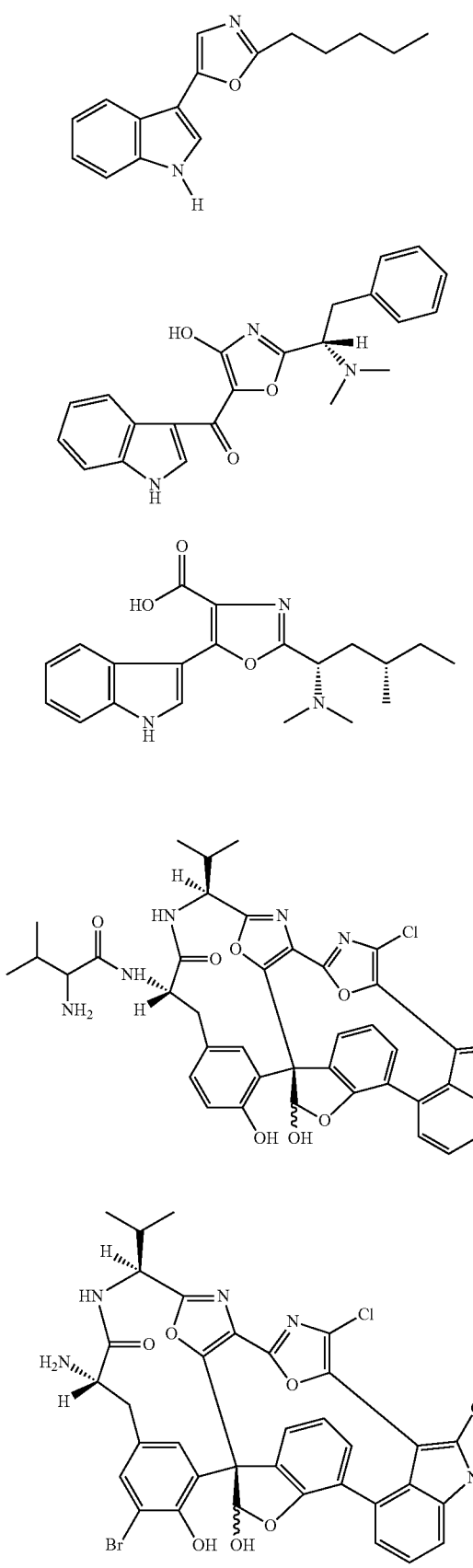
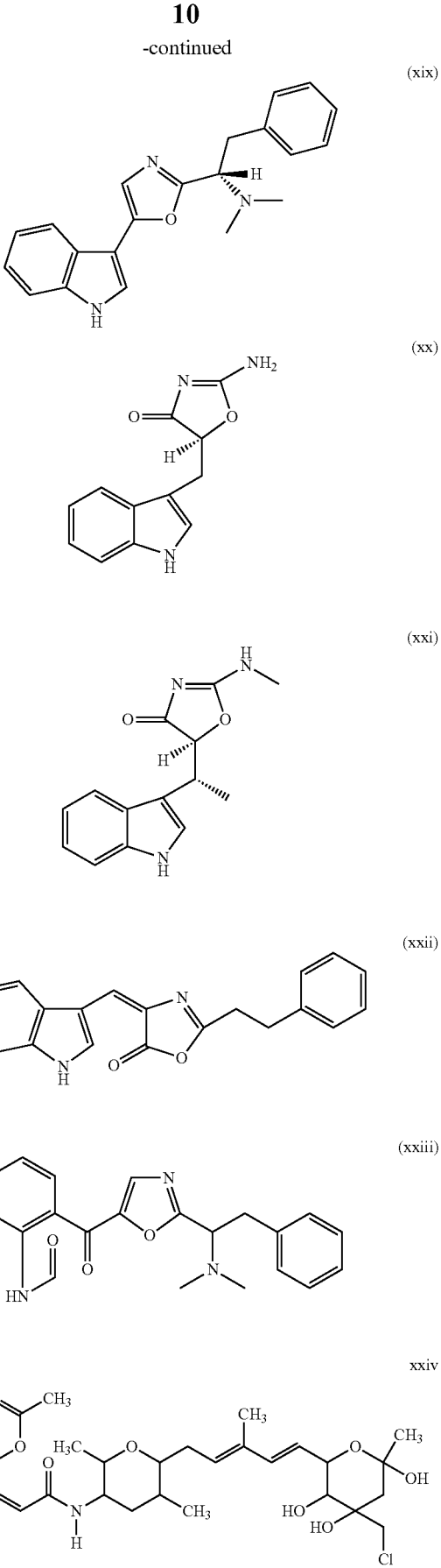

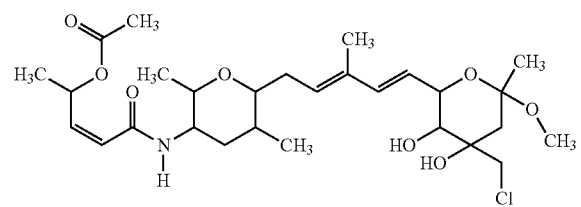
xxv
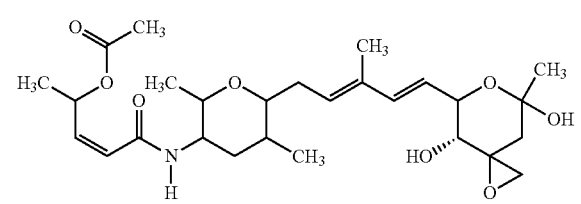
xxvi
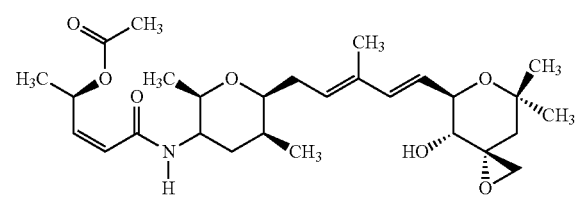
xxvii
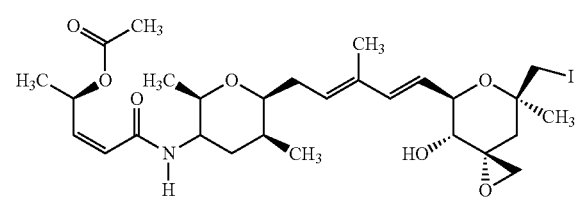
xxviii
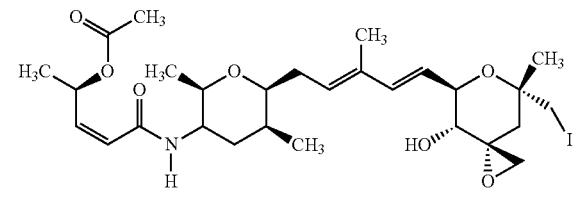
xxix
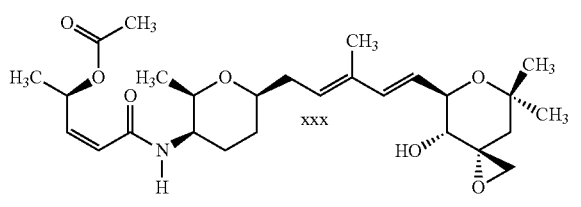
xxx
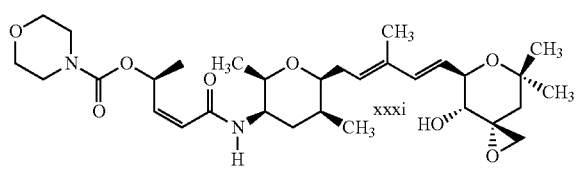
xxxi
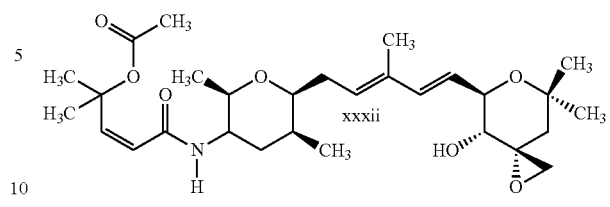
xxxii
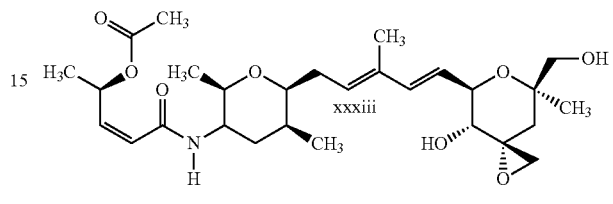
xxxiii
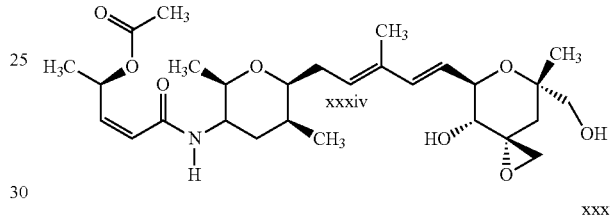
xxxiv
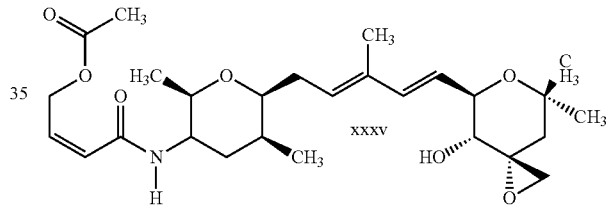
xxxv
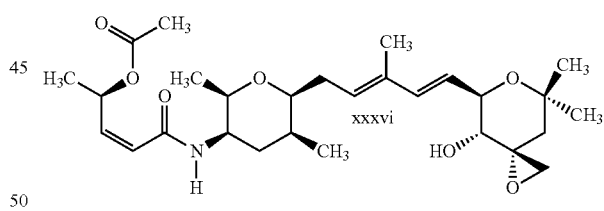
xxxvi
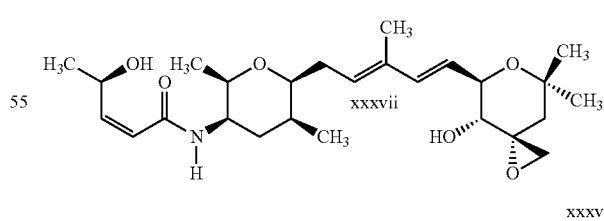
xxxvii
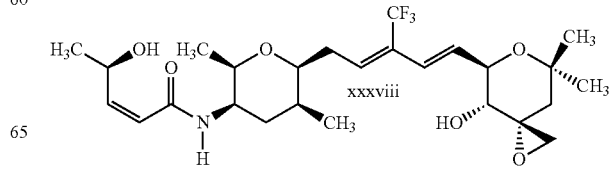
xxxviii

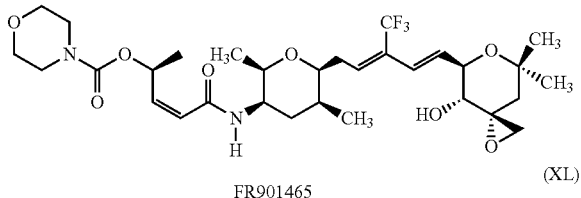

-continued xxxix (XL)

FR901465

Also provided are methods of obtaining the compounds set forth above. In particular, the method comprises culturing the *Burkholderia* strain disclosed herein and producing the compound. Further provided is a method for isolating these compounds by isolating the compound(s) produced by a *Burkholderia* strain comprising isolating compounds produced from a supernatant of a culture of said *Burkholderia* strain.

Further provided is a combination comprising (a) a first substance selected from the group consisting of (i) a pure culture, whole cell broth, comprising or cell fraction, filtrate or supernatant derived from the *Burkholderia* strain set forth above or extract thereof for use optionally as a pesticide; (ii) one or more of the compounds set forth above (b) optionally a second substance, wherein said second substance is a chemical or biological pesticide and (c) optionally at least one of a carrier, diluent, surfactant, adjuvant, or pesticide. In a particular embodiment, the combination is a composition. In a related aspect, provided herein is a seed coated with said composition. The seed may be a genetically modified seed that is herbicide resistant.

In a related aspect, disclosed is a method for modulating pest infestation in a plant comprising applying to the plant and/or seeds thereof and/or substrate used for growing said plant and/or a method for modulating emergence and/or growth of monocotyledonous, sedge or dicotyledonous weeds comprising applying to said weed or soil an amount of (I) (a) the isolated compounds set forth above and (b) optionally another substance, wherein said substance is a pesticide (e.g. nematocide, herbicide, fungicide, insecticide) or (II) the composition or combination set forth above in an amount effective to modulate pest infestation and/or emergence or growth of monocotyledonous, sedge or dicotyledonous weeds.

In another related aspect, provided is the use of the strains, cultures, extracts, supernatants, combinations, compounds set forth above for modulating pest infestation in a plant comprising applying to the plant and/or seeds thereof and/or substrate used for growing said plant and/or a method for modulating emergence and/or growth of monocotyledonous, sedge or dicotyledonous weeds. The weeds may be grass weeds (e.g., *Digitaria sanguinalis, Echinochloa grus-gali, Phalaris minor* and *Lolium perenne*), sedge weeds (e.g., *Cyperus difformis*) or broadleaf weeds (e.g., *Brassica juncea, Trifolium repens, Conyza canadensis, Conyza bonariensis, Amaranthus palmeri, Amaranthus rudis, Ambrosia artemisifolia, Ambrosia trifida, Kochia scoparia, Solanum nigrum, Oxalis stricta, Chenopodium album, Medicago polymorpha, Taraxacum oficinale, Convolvulus arvensos, Pueraria lobata, Malva parviflora, Gallium aparine*). Further provided are seeds coated with the combinations, cultures, extracts, strains, compounds supernatant, whole cell broth, cell fractions set forth above. The seeds may be genetically modified seeds that may be herbicide resistant.

Figure 1:
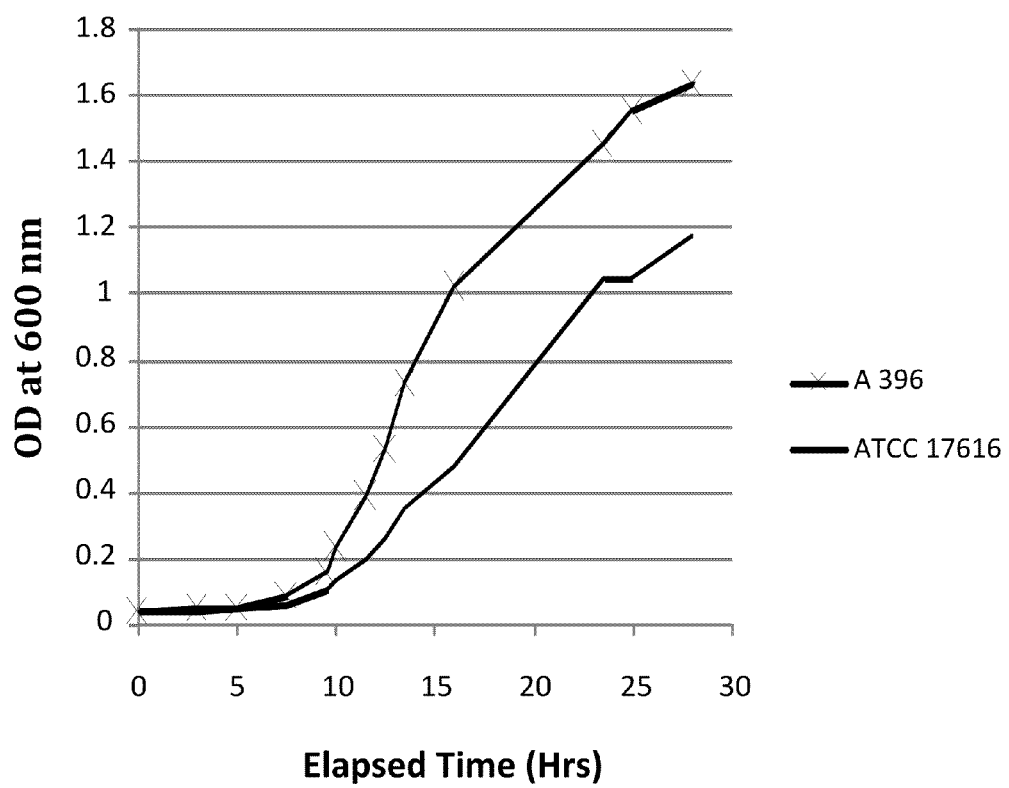
FIG. 1 shows the comparison of the growth rate of *Burkholderia* A396 to *Burkholderia multivorans* ATCC 17616.

FIG. 2 shows the effect of untreated control ("UTC") and *Burkholderia* A396 extract at 5 mg/mL and 10 mg/mL on bindweed.

FIG. 3 shows the effect of untreated control ("UTC") and *Burkholderia* A396 extract at 1.25 mg/mL, 2.5 mg/mL, 5.0 mg/mL, and 10.0 mg/mL on pigweed.

FIG. 4 shows the effect of filter-sterilized *Burkholderia* A396 broth diluted by half ("½x") and undiluted ("1x") on Cabbage looper (*Tricoplusia nth.*

FIG. 5 shows the effect of *Burkholderia* A396 culture broth diluted by half ("½x") and undiluted ("1x") on Beet armyworm (*Spodoptera exigua*).

FIG. 6 shows the effect of *Burkholderia* A396 culture broth on the motility of juvenile root-knot nematodes (*Meloidogyne incognita*).

FIG. 7 is a schematic representation of purification scheme for obtaining the templazole and templamide compounds.

FIG. 8 shows results of an in vitro assay to test the fungicidal effect of FR90128 on *Botrytis cinerea* (left) and *Phytophtora* sp. (right).

FIG. 9 shows the effect of *Burkholderia* A396 culture broth on the average gall index (% control) of cucumber roots cv. Toschka inoculated with 3000 eggs of *Meloidogyne* sp. 14 days after inoculation and application.

FIG. 10 Effect of *Burkholderia* A396 culture broth on the average gall index of cucumber roots cv. Toschka inoculated with 3000 eggs of *Meloidogyne* sp. 14 days after inoculation and application.

DETAILED DESCRIPTION OF EMBODIMENTS

While the compositions and methods heretofore are susceptible to various modifications and alternative forms, exemplary embodiments will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Where a range of values is provided, it is understood that each intervening value, to the tenth of the unit of the lower limit unless the context clearly dictates otherwise, between the upper and lower limit of that range and any other stated or intervening value in that stated range, is included therein. Smaller ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," and the include plural references unless the context clearly dictates otherwise.

As defined herein, "derived from" means directly isolated or obtained from a particular source or alternatively having identifying characteristics of a substance or organism isolated or obtained from a particular source.

As defined herein, an "isolated compound" is essentially free of other compounds or substances, e.g., at least about 20% pure, preferably at least about 40% pure, more preferably about 60% pure, even more preferably about 80% pure, most preferably about 90% pure, and even most preferably about 95% pure, as determined by analytical methods, including but not limited to chromatographic methods, electrophoretic methods.

As used herein, the term "alkyl" refers to a monovalent straight or branched chain hydrocarbon group having from one to about 12 carbon atoms, including methyl, ethyl, n-propyl, isopropyl, n-butyl, isobutyl, tert-butyl, n-hexyl, and the like.

As used herein, "substituted alkyl" refers to alkyl groups further bearing one or more substituents selected from hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, amino, amido, —C(O)H, acyl, oxyacyl, carboxyl, sulfonyl, sulfonamide, sulfuryl, and the like.

As used herein, "alkenyl" refers to straight or branched chain hydrocarbyl groups having one or more carbon-carbon double bonds, and having in the range of about 2 up to 12 carbon atoms, and "substituted alkenyl" refers to alkenyl groups further bearing one or more substituents as set forth above.

As used herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "heteroaryl" refers to aromatic rings containing one or more heteroatoms (e.g., N, O, S, or the like) as part of the ring structure, and having in the range of 3 up to 14 carbon atoms and "substituted heteroaryl" refers to heteroaryl groups further bearing one or more substituents as set forth above.

As used herein, "alkoxy" refers to the moiety —O-alkyl-, wherein alkyl is as defined above, and "substituted alkoxy" refers to alkoxyl groups further bearing one or more substituents as set forth above.

As used herein, "thioalkyl" refers to the moiety —S-alkyl-, wherein alkyl is as defined above, and "substituted thioalkyl" refers to thioalkyl groups further bearing one or more substituents as set forth above.

As used herein, "cycloalkyl" refers to ring-containing alkyl groups containing in the range of about 3 up to 8 carbon atoms, and "substituted cycloalkyl" refers to cycloalkyl groups further bearing one or more substituents as set forth above.

As used herein, "heterocyclic", refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituent's as set forth above.

The *Burkholderia* Strain

The *Burkholderia* strain set forth herein is a non-*Burkholderia cepacia* complex, non-*Burkholderia plantari*, non-*Burkholderia gladioli*, *Burkholderia* sp and non-pathogenic to vertebrates, such as birds, mammals and fish. This strain may be isolated from a soil sample using procedures known in the art and described by Lorch et al., 1995. The *Burkholderia* strain may be isolated from many different types of soil or growth medium. The sample is then plated on potato dextrose agar (PDA). The bacteria are gram negative, and it forms round, opaque cream-colored colonies that change to pink and pinkish-brown in color and mucoid or slimy over time.

Colonies are isolated from the potato dextrose agar plates and screened for those that have biological, genetic, biochemical and/or enzymatic characteristics of the *Burkholderia* strain of the present invention set forth in the Examples below. In particular, the *Burkholderia* strain has a 16S rRNA gene comprising a forward sequence that is at least about 99.0%, preferably about 99.5%, more preferably about 99.9% and most preferably about 100% identical to the sequence set forth in SEQ ID NO: 8, 11 and 12 and a forward sequence that is at least about 99.0%, preferably about 99.5%, more preferably about 99.9% and most preferably about 100% identical to the sequence set forth in SEQ ID NO: 9, 10, 13, 14 and 15 as determined by clustal analysis. Furthermore, as set forth below, this *Burkholderia* strain may, as set forth below, have pesticidal activity, particularly, virucidal, herbicidal, germicidal, fungicidal, nematicidal, bactericidal and insecticidal and more particularly, herbicidal, insecticidal, fungicidal and nematicidal activity. It is not pathogenic to vertebrate animals, such as mammals, birds, and fish.

Additionally, the *Burkholderia* strain produces at least the pesticidal compounds set forth in the instant disclosure.

The *Burkholderia* strain is susceptible to kanamycin, chloramphenicol, ciprofloxacin, piperacillin, imipenem, and a combination of sulphamethoxazole and trimethoprim and contains the fatty acids 16:0, cyclo 17:0, 16:0 3-OH, 14:0, cyclo 19:0, 18:0.

This *Burkholderia* strain may be obtained by culturing a microorganism having the identifying characteristics of *Burkholderia* A396 (NRRL Accession No. B-50319) on Potato Dextrose Agar (PDA) or in a fermentation medium containing defined carbon sources such as glucose, maltose, fructose, galactose, and undefined nitrogen sources such as peptone, tryptone, soytone, and NZ amine.

Pesticidal Compounds

The pesticidal compound disclosed herein may have the following properties: (a) is obtainable from a novel *Burkholderia* species, e.g., A396; (b) is, in particular, toxic to most common agricultural insect pests; (c) has a molecular weight of about 525-555 and more particularly, 540 as determined by Liquid Chromatography/Mass Spectroscopy (LC/MS); (d) has $^1$H NMR values of 6.22, 5.81, 5.69, 5.66, 5.65, 4.64, 4.31, 3.93, 3.22, 3.21, 3.15, 3.10, 2.69, 2.62, 2.26, 2.23, 1.74, 1.15, 1.12, 1.05, 1.02; (d) has $^{13}$C NMR values of 172.99, 172.93, 169.57, 169.23, 167.59, 130.74, 130.12, 129.93, 128.32, 73.49, 62.95, 59.42, 57.73, 38.39, 38.00, 35.49, 30.90, 30.36, 29.26, 18.59, 18.38, 18.09, 17.93, 12.51 (e) has an High Pressure Liquid Chromatography (HPLC) retention time of about 10-15 minutes, more specifically about 12 minutes and even more specifically about 12.14 min on a reversed phase C-18 HPLC (Phenomenex, Luna 5µ C18 (2) 100A, 100×4.60 mm) column using a water:acetonitrile (CH$_3$CN) with a gradient solvent system (0-20 min 90-0% aqueous CH$_3$CN, 20-24 min 100% CH$_3$CN, 24-27 min, 0-90% aqueous CH$_3$CN, 27-30 min 90% aqueous CH$_3$CN) at 0.5 mL/min flow rate and UV detection of 210 nm (f) has a molecular formula, C$_{24}$H$_{36}$N$_4$O$_6$S$_2$, which is determined by interpretation of $^1$H, $^{13}$C NMR and LC/MS data (g) a $^{13}$C NMR spectrum with signals for all 24 carbons, including 5 methyl, 4 methylene, 9 methine, and 6 quaternary carbons and (g) $^1$H NMR spectrum displaying characteristics of a typical depsipeptide, illustrating three-amino protons [4.63, 4.31, 3.93], and one ester carbinol proton [5.69]. In a particular embodiment, the compound has the structure ##STR001##:

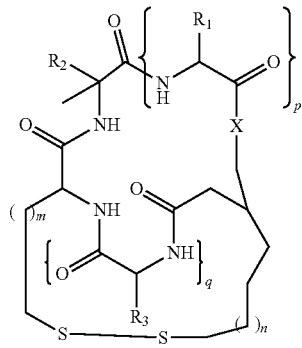

Or a pesticidally acceptable salt or stereoisomers thereof, wherein M is 1, 2, 3 or 4; n is 0, 1, 2, or 3; p and q are independently 1 or 2; X is O, NH or NR; $R_1$, $R_2$ and $R_3$ are the same or different and independently an amino acid side-chain moiety or an amino acid side-chain derivative and R is a lower chain alkyl, aryl or arylalkyl moiety.

In an even more particular embodiment, the compound has the structure of FR90128:

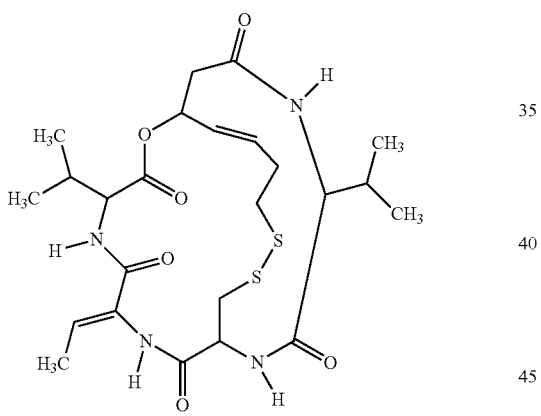

Provided herewith are compounds set forth in ##STR002##:

STR002##

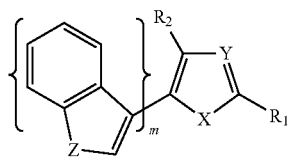

wherein: X, Y and Z are each independently —O—, —$NR_1$—, or —S—, wherein $R_1$ is —H or $C_1$-$C_{10}$ alkyl; $R_1$, $R_2$ and m are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl.

In an even another particular embodiment, Family ##STR002## compounds may be the compounds set forth in (vi)-(xix).

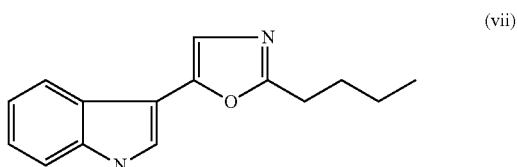
(vii)

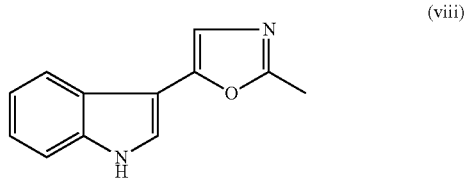
(viii)

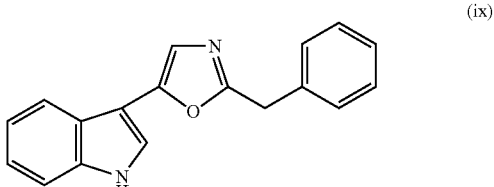
(ix)

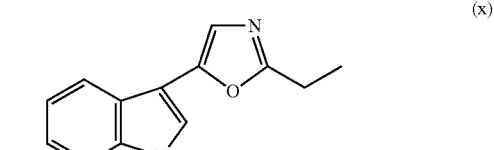
(x)

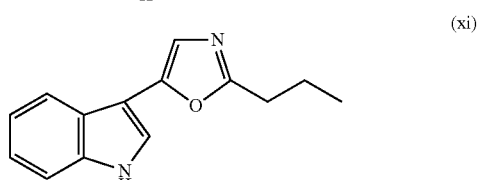
(xi)

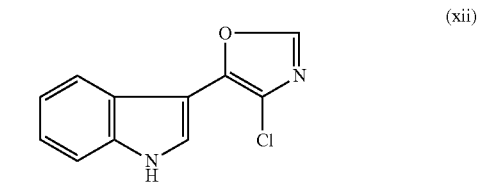
(xii)

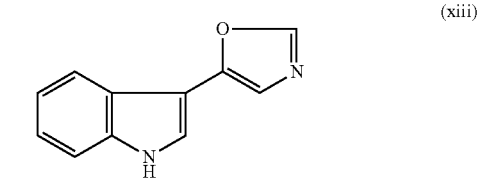
(xiii)

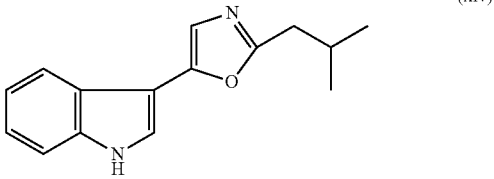
(xiv)

-continued

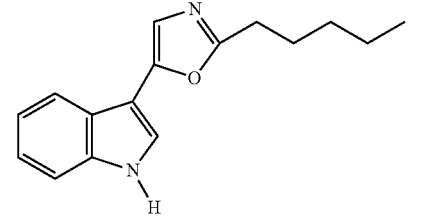
(xv)

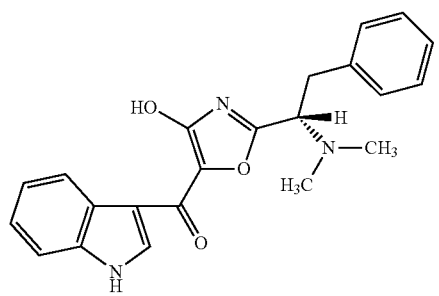
(xvi)

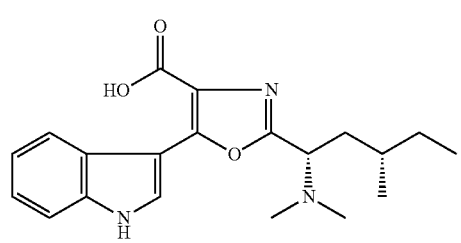
(xvii)

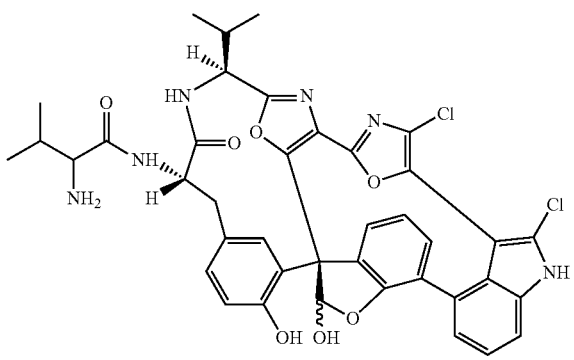
(xviii)

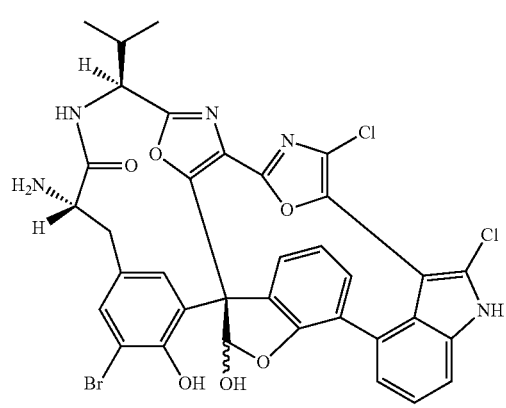
(xix)

-continued

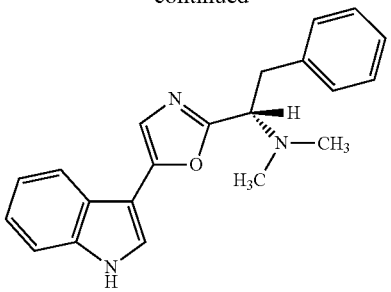

These are from either natural materials or compounds obtained from commercial sources or by chemical synthesis. Natural sources of Family ##STR002## compounds include, but are not limited to, microorganisms, alga, and sponges. In a more particular embodiment, microorganisms which include the Family ##STR002## compounds include but are not limited to, or alternatively, Family ##STR002## compounds may be derived from species such as *Streptoverticillium waksmanii* (compound vi) (Umehara, et al., 1984), *Streptomyces pimprina* (compound vii) (Naiket al., 2001), *Streptoverticillium olivoreticuli* (compounds viii, ix, x) (Koyama Y., et al., 1981), *Streptomyces* sp (compounds xi, xii) (Watabe et al., 1988), *Pseudomonas syringae* (compounds xiii, xiv) (Pettit et al., 2002). Family ##STR002## compounds may also be derived from algae including but not limited to red alga (compound xv) (N'Diaye, et al., 1996), red alga *Martensia fragilis* (compound xvi) (Takahashi S. et al., 1998), *Diazona chinensis* (compounds xvii & xviii) (Lindquist N. et al., 1991), *Rhodophycota haraldiophyllum* sp (compound xix) (Guella et al., 1994).

Also provided is ##STR003##:

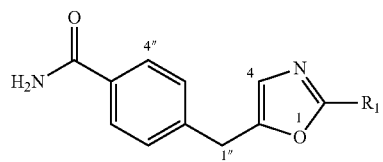

wherein: X and Y are each independently —OH, —NR$_1$, or —S, wherein R$_1$ is —H or C$_1$-C$_{10}$ alkyl; R$_1$, R$_2$ and m, a substituent on the oxazole ring, are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl.

Further provided is ##STR005##:

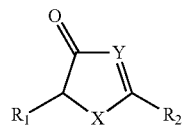

wherein X and Y are each independently —OH, —NR$_1$, or —S, wherein R$_1$, R$_2$ are each independently —H, alkyl (e.g., C$_1$-C$_{10}$alkyl), substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl.

In a particular embodiment, Family ##STR005## compounds such as compounds from xx-xxiii set forth below may be derived from natural or commercial sources or by chemical synthesis:

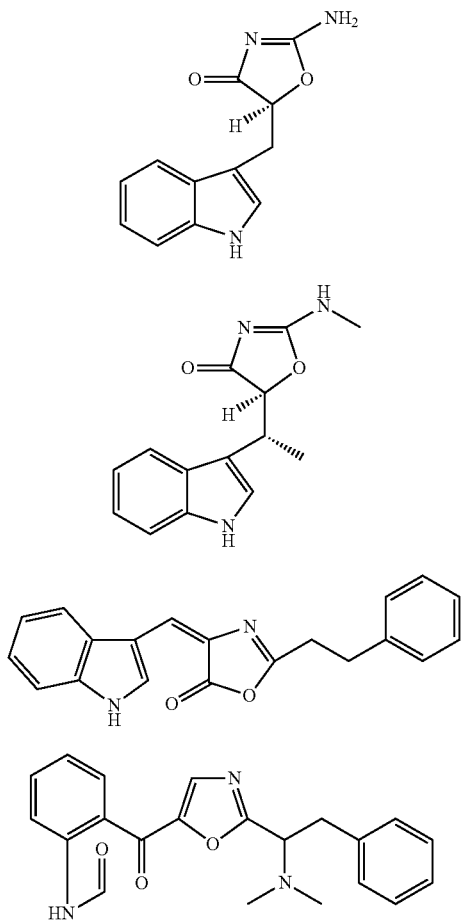

Natural sources of Family ##STR005## compounds include, but are not limited to plants, corals, microorganisms, and sponges. The microorganisms include, but are not limited to *Streptomyces griseus* (compound xx) (Hirota et al., 1978), *Streptomyces albus* (compound xxi) (Werner et al., 1980). Family STR004 compounds may also be derived from algae including but not limited to *Haraldiophyllum* sp (compound xxii (Guella et al., 2006), and red algae (compound xxiii) (N'Diaye et al., 1994).

In one embodiment, the compound may be derived from or is obtainable from a microorganism, and in particular from *Burkholderia* species and characterized as having a structure comprising at least one ester, at least one amide, at least three methylene groups, at least one tetrahydropyranose moiety and at least three olefinic double bonds, at least six methyl groups, at least three hydroxyl groups, at least twenty five carbons and at least eight oxygen and one nitrogen. The compound further comprises at least one of the following characteristics:

(a) pesticidal properties and in particular, nematicidal, fungicidal, insecticidal and herbicidal properties;

(b) a molecular weight of about 530-580 and more particularly, 555 as determined by Liquid Chromatography/Mass Spectroscopy (LC/MS);

(c) $^1$H NMR values of δ 6.40, 6.39, 6.00, 5.97, 5.67, 5.54, 4.33, 3.77, 3.73, 3.70, 3.59, 3.47, 3.41, 2.44, 2.35, 2.26, 1.97, 1.81, 1.76, 1.42, 1.37, 1.16, 1.12, 1.04;

(d) $^{13}$C NMR values of δ 173.92, 166.06, 145.06, 138.76, 135.71, 129.99, 126.20, 123.35, 99.75, 82.20, 78.22, 76.69, 71.23, 70.79, 70.48, 69.84, 60.98, 48.84, 36.89, 33.09, 30.63, 28.55, 25.88, 20.37, 18.11, 14.90, 12.81, 9.41;

(e) an High Pressure Liquid Chromatography (HPLC) retention time of about 7-12 minutes, more specifically about 10 minutes and even more specifically about 10.98 min on a reversed phase C-18 HPLC (Phenomenex, Luna 5μ C18(2) 100 A, 100×4.60 mm) column using a water:acetonitrile (CH$_3$CN) with a gradient solvent system (0-20 min; 90-0% aqueous CH$_3$CN, 20-24 min; 100% CH$_3$CN, 24-27 min; 0-90% aqueous CH$_3$CN, 27-30 min; 90% aqueous CH$_3$CN) at 0.5 mL/min flow rate and UV detection of 210 nm;

(f) $^{13}$C NMR spectrum which exhibits 28 discrete carbon signals which may be attributed to six methyls, four methylene carbons, and thirteen methines including five sp$^2$, four quaternary carbons;

(g) a molecular formula of C$_{28}$H$_{45}$NO$_{10}$ which was determined by interpretation of the ESIMS and NMR data analysis;

(h) UV absorption bands between about 210-450 nm and most particularly at about 234 nm.

Also provided are compounds having the structure ##STR004a##:

STR004a##

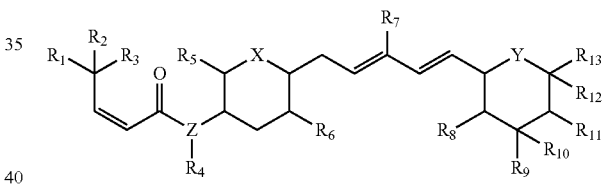

Wherein X, Y and Z are each independently —O, —NR, or —S, wherein R is H or C$_1$-C$_{10}$alkyl; R$_1$, R$_2$, R$_3$, R$_4$, R$_5$, R$_6$, R$_7$, R$_8$, R$_9$, R$_{10}$, R$_{11}$, R$_{12}$, and R$_{13}$ are each independently H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl.

In a particular embodiment, the compound has the structure set forth in ##STR004b##:

STR004b##

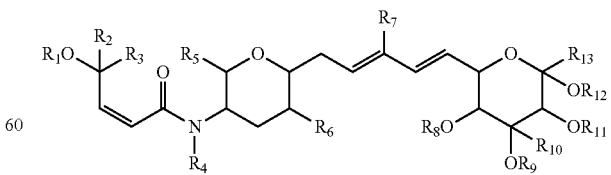

wherein R$_1$, R$_2$, R$_3$, R$_4$, R$_5$, R$_6$, R$_7$, R$_8$, R$_9$, R$_{10}$, R$_{11}$, R$_{12}$, and R$_{13}$ are as previously defined for ##STR004a##.

In a more particular embodiment, the compound is Templamide A with the following structure:

Templamide A

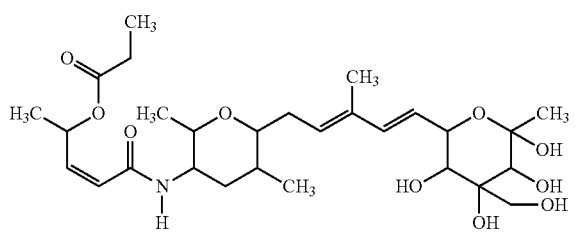

In another embodiment, provided is a compound having formula ##STR004c##:

STR004c##

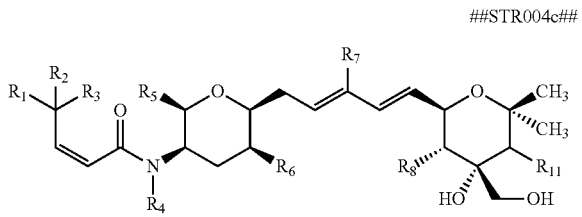

Wherein $R_1$, $R_2$, $R_3$, $R_4$, $R_5$, $R_6$, $R_7$, $R_8$, and $R_{11}$ are as previously defined for ##STR004a##.

In another embodiment, provided is a compound which may be derived from *Burkholderia* species and characterized as having a structure comprising at least one ester, at least one amide, an epoxide methylene group, at least one tetrahydropyranose moiety and at least three olefinic double bonds, at least six methyl groups, at least three hydroxyl groups, at least 25 carbons and at least 8 oxygen and 1 nitrogen, and pesticide activity. The compound further comprises at least one of the following characteristics:

(a) pesticidal properties and in particular, insecticidal, fungicidal, nematocidal and herbicidal properties;

(b) a molecular weight of about 520-560 and particularly 537 as determined by Liquid Chromatography/Mass Spectroscopy (LC/MS);

(c) $^1$H NMR δ values at about 6.41, 6.40, 6.01, 5.97, 5.67, 5.55, 4.33, 3.77, 3.75, 3.72, 3.64, 3.59, 3.54, 3.52, 2.44, 2.34, 2.25, 1.96, 1.81, 1.76, 1.42, 1.38, 1.17, 1.12, 1.04;

(d) $^{13}$C NMR values of δ 174.03, 166.12, 143.63, 137.50, 134.39, 128.70, 126.68, 124.41, 98.09, 80.75, 76.84, 75.23, 69.87, 69.08, 68.69, 68.60, 48.83, 41.07, 35.45, 31.67, 29.19, 27.12, 24.55, 19.20, 18.95, 13.48, 11.39, 8.04;

(e) High Pressure Liquid Chromatography (HPLC) retention time of about 6-15 minutes, more specifically about 8 minutes on a reversed phase C-18 HPLC column using a water:acetonitrile ($CH_3CN$) gradient, particularly, an High Pressure Liquid Chromatography (HPLC) retention time of about 8-15 minutes, more specifically about 11 minutes and even more specifically about 11.73 min on a reversed phase C-18 HPLC (Phenomenex, Luna 5μ C18(2) 100A, 100×4.60 mm) column using a water:acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm;

(f) a molecular formula of $C_{28}H_{43}NO_9$ which was determined by interpretation of the ESIMS and NMR data analysis;

(g) UV absorption bands at about 210-450 nm and most particularly at about 234 nm.

In a particular embodiment, the compound has the structure ##STR006a##:

STR006a##

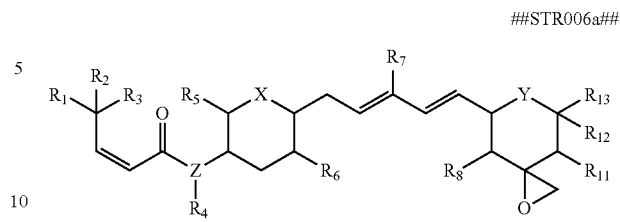

Wherein X, Y and Z are each independently —O—, —NR, or —S—, wherein R is H or $C_1$-$C_{10}$ alkyl; $R_1$, $R_2$, $R_3$, $R_4$, $R_5$, $R_6$, $R_7$, $R_8$, $R_{11}$, $R_{12}$, and $R_{13}$ are each independently H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl.

In a particular embodiment, the compound has the structure:

Templamide A

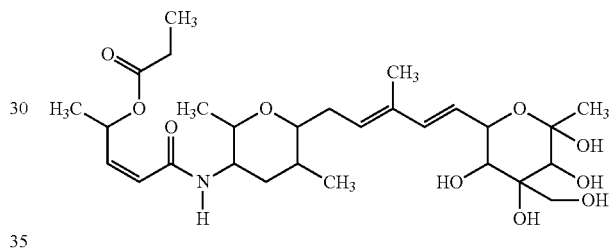

In another embodiment, provided is a compound having formula ##STR006b##:

STR006b##

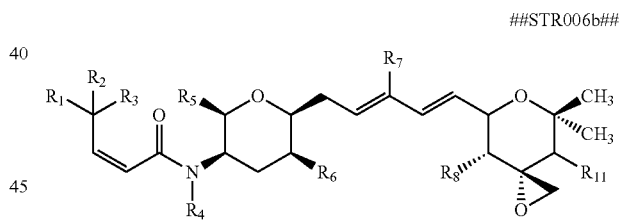

Wherein $R_1$, $R_2$, $R_3$, $R_4$, $R_5$, $R_6$, $R_7$, $R_8$, and $R_{11}$, are as previously defined for ##STR006a##.

In a more particular embodiment, the compound is Templamide B with the following structure:

Templamide B

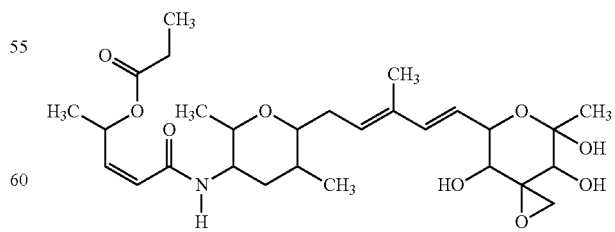

In yet another particular embodiment, the compound may be derived from *Burkholderia* species and characterized as having a structure comprising at least one ester, at least one amide, an epoxide methylene group, at least one tetrahydropyranose moiety and at least three olefinic double bonds, at least six methyl groups, at least three hydroxyl groups, at least 25 carbons and at least 8 oxygens and at least 1 nitrogen. The compound further comprises at least one of the following characteristics:

(a) pesticidal properties and in particular, insecticidal, fungicidal, nematicidal and herbicidal properties;

(b) a molecular weight of about 510-550 and particularly about 523 as determined by Liquid Chromatography/Mass Spectroscopy (LC/MS);

(c) $^1$H NMR δ values at about 6.41, 6.40, 6.01, 5.98, 5.68, 5.56, 4.33, 3.77, 3.75, 3.72, 3.65, 3.59, 3.55, 3.50, 2.44, 2.26, 2.04, 1.96, 1.81, 1.75, 1.37, 1.17, 1.04;

(d) $^{13}$C NMR δ values of 172.22, 167.55, 144.98, 138.94, 135.84, 130.14, 125.85, 123.37, 99.54, 82.19, 78.28, 76.69, 71.31, 70.13, 69.68, 48.83, 42.52, 36.89, 33.11, 30.63, 25.99, 21.20, 20.38, 18.14, 14.93, 12.84;

(e) an High Pressure Liquid Chromatography (HPLC) retention time of about 6-15 minutes, more specifically about 8 minutes on a reversed phase C-18 HPLC column using a water:acetonitrile (CH$_3$CN) gradient, particularly, an High Pressure Liquid Chromatography (HPLC) retention time of about 8-15 minutes, more specifically about 10 minutes and even more specifically about 10.98 min on a reversed phase C-18 HPLC (Phenomenex, Luna 5μ C18(2) 100 A, 100×4.60 mm) column using a water:acetonitrile (CH$_3$CN) with a gradient solvent system (0-20 min; 90-0% aqueous CH$_3$CN, 20-24 min; 100% CH$_3$CN, 24-27 min; 0-90% aqueous CH$_3$CN, 27-30 min; 90% aqueous CH$_3$CN) at 0.5 mL/min flow rate and UV detection at 210 nm;

(f) a molecular formula of C$_{27}$H$_{41}$NO$_9$ which was determined by interpretation of the ESIMS and NMR data analysis;

(g) UV absorption bands at about 210-450 nm and most particularly at about 234 nm.

In a more particular embodiment, the compound is a known compound FR901465 which was isolated earlier from culture broth of a bacterium of *Pseudomonas* sp. No. 2663 (Nakajima et al. 1996) and had been reported to have anticancer activity with the following structure:

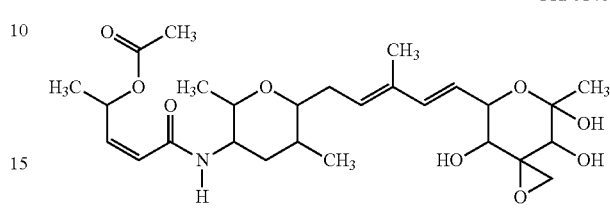

FR901465

In an even another particular embodiment, Family ##STR006a## compounds may be the compounds set forth in xxiv to xxxix. These are from either natural materials or compounds obtained from commercial sources or by chemical synthesis. Natural sources of Family ##STR006a## compounds include, but are not limited to, microorganisms, alga, and sponges. In a more particular embodiment, microorganisms which include the Family ##STR006a## compounds which may be derived from species such as *Pseudomonas* sp. No. 2663 (compounds xxiv-xxvi) (Nakajima et al., 1996). The synthetic analogues of the FR901464 (xxvii-xxxix) which have been synthesized and patented as anticancer compounds (see Koide et al., US Patent Application No. 2008/0096879 A1).

xxiv

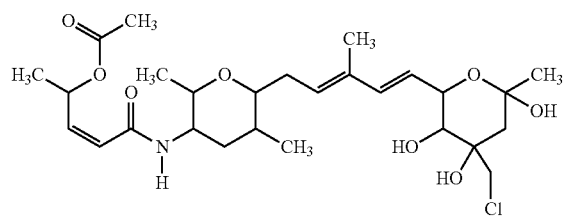

xxv

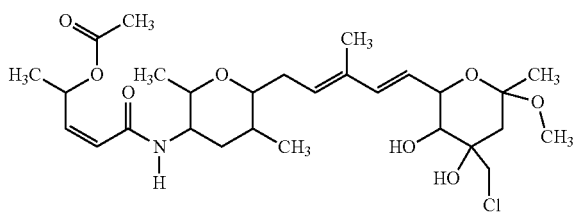

xxvi

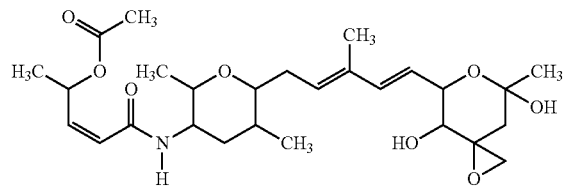

xxvii

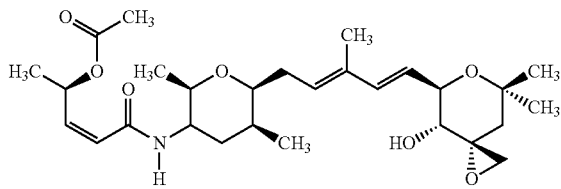

xxviii

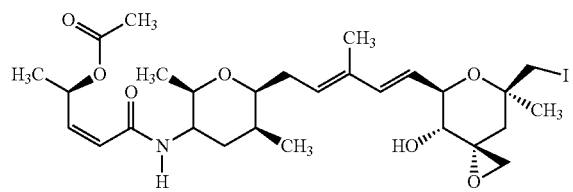

xxix

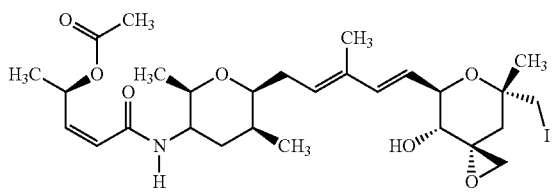

-continued
xxx
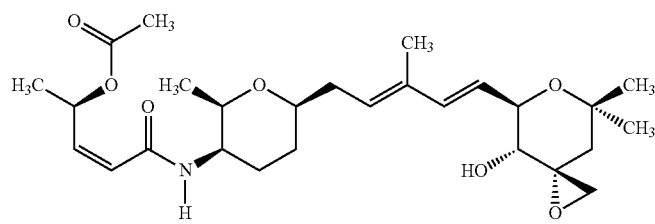
xxxi
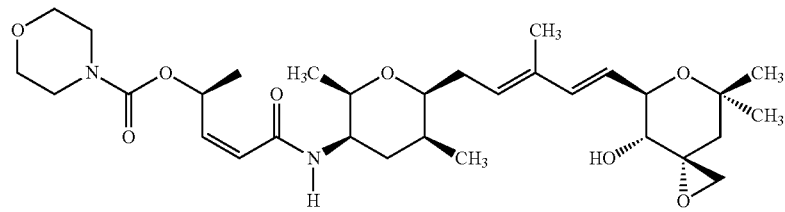
xxxii
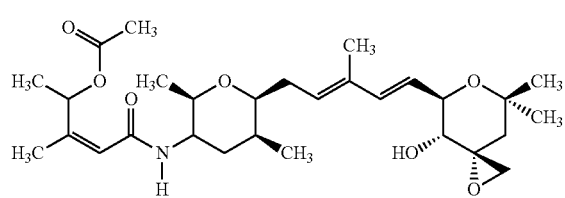
xxxiii
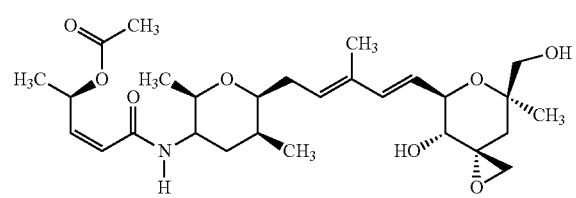
xxxiv
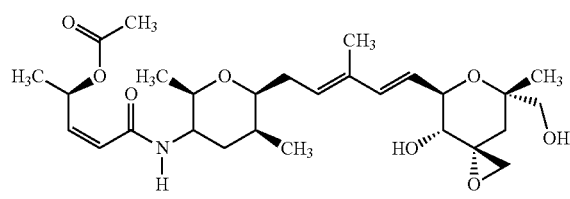
xxxv
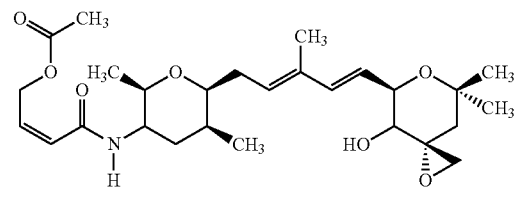
xxxvi
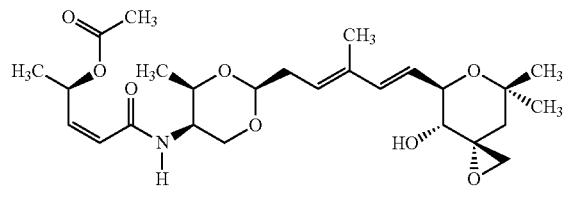
xxxvii
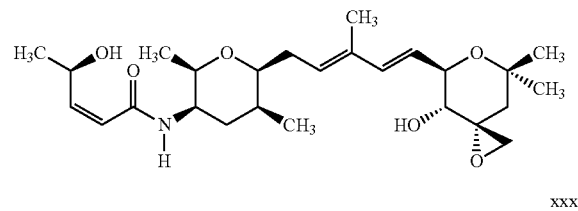
xxxviii
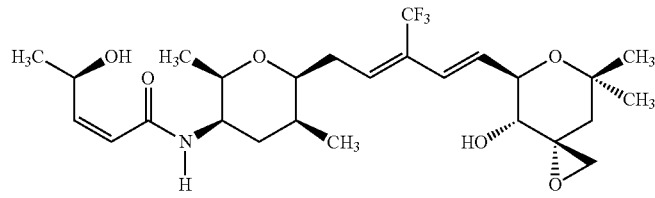
xxxix
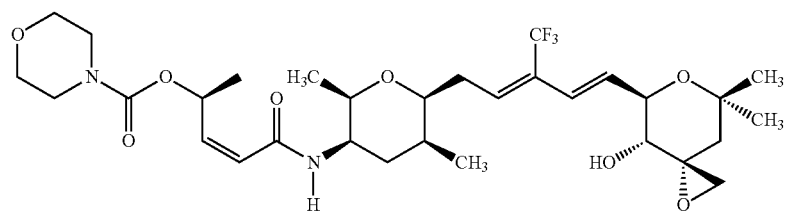

Compositions

A substantially pure culture, cell fraction or supernatant and compounds produced by the *Burkholderia* strain of the present invention, may be formulated into pesticidal compositions.

The substances set forth above can be formulated in any manner. Non-limiting formulation examples include but are not limited to emulsifiable concentrates (EC), wettable powders (WP), soluble liquids (SL), aerosols, ultra-low volume concentrate solutions (ULV), soluble powders (SP), microencapsulation, water dispersed granules, flowables (FL), microemulsions (ME), nano-emulsions (NE), etc. In particular, the concentrate, powders, granules and emulsions may be freeze-dried. In any formulation described herein, percent of the active ingredient is within a range of 0.01% to 99.99%.

The compositions may be in the form of a liquid, gel or solid. Liquid compositions comprise pesticidal compounds derived from said *Burkholderia* strain, e.g. a strain having the identifying characteristics of *Burkholderia* A396 (NRRL Accession No. B-50319).

A solid composition can be prepared by suspending a solid carrier in a solution of pesticidal compounds and drying the suspension under mild conditions, such as evaporation at room temperature or vacuum evaporation at 65° C. or lower.

A composition of the invention may comprise gel-encapsulated compounds derived from the *Burkholderia* strain of the present invention. Such gel-encapsulated materials can be prepared by mixing a gel-forming agent (e.g., gelatin, cellulose, or lignin) with a solution of pesticidal compounds used in the method of the invention; and inducing gel formation of the agent.

The composition may additionally comprise a surfactant to be used for the purpose of emulsification, dispersion, wetting, spreading, integration, disintegration control, stabilization of active ingredients, and improvement of fluidity or rust inhibition. In a particular embodiment, the surfactant is a non-phytotoxic non-ionic surfactant which preferably belongs to EPA List 4B. In another particular embodiment, the nonionic surfactant is polyoxyethylene (20) monolaurate. The concentration of surfactants may range between 0.1-35% of the total formulation, preferred range is 5-25%. The choice of dispersing and emulsifying agents, such as non-ionic, anionic, amphoteric and cationic dispersing and emulsifying agents, and the amount employed is determined by the nature of the composition and the ability of the agent to facilitate the dispersion of these compositions.

The composition may further comprise another microorganism and/or pesticide (e.g, nematocide, fungicide, insecticide). The microorganism may include but is not limited to an agent derived from *Bacillus* sp., *Pseudomonas* sp., *Brevabacillus* sp *Lecanicillium* sp., non-*Ampelomyces* sp., *Pseudozyma* sp., *Streptomyces* sp, *Burkholderia* sp, *Trichoderma* sp, *Gliocladium* sp. Alternatively, the agent may be a natural oil or oil-product having fungicidal and/or insecticidal activity (e.g., paraffinic oil, tea tree oil, lemongrass oil, clove oil, cinnamon oil, citrus oil, rosemary oil).

The composition, in particular, may further comprise an insecticide. The insecticide may include but is not limited to avermectin, *Bacillus thuringiensis*, neem oil and azadiractin, spinosads. *Chromobacterium subsugae*, eucalyptus extract, entomopathogenic bacterium or fungi such a *Beauveria bassiana*, and *Metarrhizium anisopliae* and chemical insecticides including but not limited to organochlorine compounds, organophosphorous compounds, carbamates, pyrethroids, and neonicotinoids.

The composition my further comprise a nematicide. The nematicide may include, but is not limited to chemical nematicides such as fenamiphos, aldicarb, oxamyl, carbofuran, natural product neamticide, avermectin, the fungi *Paecilomyces lilacinas* and *Muscodor* spp., the bacteria *Bacillus firmus* and other *Bacillus* spp. and *Pasteuria penetrans*.

The composition may further comprise a biofungicide such as extract of *R. sachalinensis* (Regalia) or a fungicide. Such fungicides include, but are not limited to, a single site antifungal agent which may include but is not limited to benzimidazole, a demethylation inhibitor (DMI) (e.g., imidazole, piperazine, pyrimidine, triazole), morpholine, hydroxypyrimidine, anilinopyrimidine, phosphorothiolate, quinone outside inhibitor, quinoline, dicarboximide, carboximide, phenylamide, anilinopyrimidine, phenylpyrrole, aromatic hydrocarbon, cinnamic acid, hydroxyanilide, antibiotic, polyoxin, acylamine, phthalimide, benzenoid (xylylalanine). In yet a further embodiment, the antifungal agent is a demethylation inhibitor selected from the group consisting of imidazole (e.g., triflumizole), piperazine, pyrimidine and triazole (e.g., bitertanol, myclobutanil, penconazole, propiconazole, triadimefon, bromuconazole, cyproconazole, diniconazole, fenbuconazole, hexaconazole, tebuconazole, tetraconazole, propiconazole).

The antimicrobial agent may also be a multi-site non-inorganic, chemical fungicide selected from the group consisting of a nitrile (e.g., chloronitrile or fludioxonil), quinoxaline, sulphamide, phosphonate, phosphite, dithiocarbamate, chloralkylhios, phenylpyridin-amine, cyano-acetamide oxime.

The compositions may be applied using methods known in the art. Specifically, these compositions may be applied to plants or plant parts. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment of the plants and plant parts with the compositions set forth above may be carried out directly or by allowing the compositions to act on their surroundings, habitat or storage space by, for example, immersion, spraying, evaporation, fogging, scattering, painting on, injecting. In the case that the composition is applied to a seed, the composition may be applied to the seed as one or more coats prior to planting the seed using one or more coats using methods known in the art.

As noted above, the compositions may be herbicidal compositions. The composition may further comprise one or more herbicides. These may include, but are not limited to, a bioherbicide and/or a chemical herbicide. The bioherbicide may be selected from the group consisting of clove, cinnamon, lemongrass, citrus oils, orange peel oil, tentoxin, cornexistin, AAL-toxin, leptospermone, thaxtomin, sarmentine, momilactone B, sorgoleone, ascaulatoxin and ascaulatoxin aglycone. The chemical herbicide may include, but is not limited to, diflufenzopyr and salts thereof, dicamba and salts thereof, topramezone, tembotrione, S-metolachlor, atrazine, mesotrione, primisulfuron-methyl, 2,4-dichlorophenoxyacetic acid, nicosulfuron, thifensulfuron-methyl, asulam, metribuzin, diclofop-methyl, fluazifop, fenoxaprop-p-ethyl, asulam, oxyfluorfen, rimsulfuron, mecoprop, and quinclorac, thiobencarb, clomazone, cyhalofop, propanil, bensulfuron-methyl, penoxsulam, triclopyr, imazethapyr, halosulfuron-methyl, pendimethalin, bispyribac-sodium, carfentrazone ethyl, sodium bentazon/sodium acifluorfen, glyphosate, glufosinate and orthosulfamuron.

Herbicidal compositions may be applied in liquid or solid form as pre-emergence or post-emergence formulations.

For pre-emergence dry formulations, the granule size of the carrier is typically 1-2 mm (diameter) but the granules can be either smaller or larger depending on the required ground coverage. Granules may comprise porous or non-porous particles.

For post-emergence formulations, the formulation components used may contain smectite clays, attapulgite clays and similar swelling clays, thickeners such as xanthan gums, gum Arabic and other polysaccharide thickeners as well as dispersion stabilizers such as nonionic surfactants (for example polyoxyethylene (20) monolaurate).

Uses

The compositions and pesticidal compounds derived from the *Burkholderia* strain set forth herein may be used as pesticides, particularly as insecticides, nematocides, fungicides and herbicides.

Specifically, nematodes that may be controlled using the method set forth above include but are not limited to parasitic nematodes such as root-knot, ring, sting, lance, cyst, and lesion nematodes, including but not limited to *Meloidogyne, Heterodera* and *Globodera* spp; particularly *Meloidogyne incognita* (root knot nematodes), as well as *Globodera rostochiensis* and *globodera pailida* (potato cyst nematodes); *Heterodera glycines* (soybean cyst nematode); *Heterodera schachtii* (beet cyst nematode); and *Heterodera avenae* (cereal cyst nematode).

Phytopathogenic insects controlled by the method of the present invention include but are not limited to insects from the order (a) Lepidoptera, for example, *Acleris* spp., *Adoxophyes* spp., *Aegeria* spp., *Agrotis* spp., *Alabama argillaceae, Amylois* spp., *Anticarsia gemmatalis, Archips* spp., *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora gossypiella, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;

(b) Coleoptera, for example, *Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp-, *Scarabeidae, Sitophilus* spp., *Sitotroga* spp., *Tenebrio* spp., *Tribolium* spp. and *Trogoderma* spp.; (c) Orthoptera, for example, *Blatta* spp., *Blattella* spp., *Gryllotalpa* spp., *Leucophaea maderae, Locusta* spp., *Periplaneta* spp. and *Schistocerca* spp.; (d) Isoptera, for example, *Reticulitermes* spp.; (e) Psocoptera, for example, *Liposcelis* spp.; (f) Anoplura, for example, *Haematopinus* spp., *Linognathus* spp., *Pediculus* spp., *Pemphigus* spp. and *Phylloxera* spp.; (g) *Mallophaga*, for example, *Damalinea* spp. and *Trichodectes* spp.; (h) Thysanoptera, for example, *Frankliniella* spp., *Hercinotnrips* spp., *Taeniothrips* spp., *Thrips palmi, Thrips tabaci* and *Scirtothrips aurantii*; (i) Heteroptera, for example, *Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp. and *Tniatoma* spp.; (j) Homoptera, for example, *Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lecanium corni, Lepidosaphes* spp., *Macrosiphus* spp., *Myzus* spp., *Nephotettix* spp., *Nilaparvata* spp., *Paratoria* spp., *Pemphigus* spp., *Planococcus* spp., *Pseudaulacaspis* spp., *Pseudococcus* spp., *Psylla* spp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri*; (k) Hymenoptera, for example, *Acromyrmex, Atta* spp., *Cephus* spp., *Diprion* spp., *Diprionidae, Gilpinia polytoma, Hoplocampa* spp., *Lasius* spp., *Monomorium pharaonis, Neodiprion* spp., *Solenopsis* spp. and *Vespa* spp.; (l) Diptera, for example, *Aedes* spp., *Antherigona soccata, Bibio hortulanus, Calliphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp.; (m) Siphonaptera, for example, *Ceratophyllus* spp. and *Xenopsylla cheopis* and (n) from the order Thysanura, for example, *Lepisma saccharina*. The active ingredients according to the invention may further be used for controlling crucifer flea beetles (*Phyllotreta* spp.), root maggots (*Delia* spp.), cabbage seedpod weevil (*Ceutorhynchus* spp.) and aphids in oil seed crops such as canola (rape), mustard seed, and hybrids thereof, and also rice and maize.

In a particular embodiment, the insect may be a member of the *Spodoptera*, more particularly, *Spodoptera exigua, Myzus persicae, Plutella xylostella* or *Euschistus* sp.

The substances and compositions may also be used to modulate emergence in either a pre-emergent or post-emergent formulation of monocotyledonous, sedge or dicotyledonous weeds. In a particular embodiment, the weeds may be

*Chenopodium* sp. (e.g., *Chenopodium album, Chenopodium murale*), *Abutilon* sp. (e.g., *Abutilon theophrasti*), *Helianthus* sp. (e.g., *Helianthus annuus*), *Ambrosia* sp. (e.g., *Ambrosia* artemesifolia, *Ambrosia* trifida), *Amaranthus* sp. (e.g., *Amaranthus retroflexus, Amaranthus palmeri, Amaranthus rudis, Amaranthus spinosus, Amaranthus tuberculatus*), *Convolvulus* sp. (e.g., *Convolvulus arvensis*), *Brassica* sp. (e.g., *Brassica kaber*), *Taraxacum* sp. (e.g., *Taraxacum officinale*), *Solanum* sp. (e.g., *Solanum nigrum, Solanum elaeagnifolium, Solanum physalifolium, Solanum ptycanthum*), *Malva* sp. (e.g., *Malva neglecta, Malva parviflora*), *Setaria* sp. (e.g., *Setaria lutescens*), *Bromus* sp. (e.g., *Bromus tectorum, *Bromus diandrus, Bromus hordeaceus*), *Poa* sp. (e.g., *Poa annua, Poa pratensis*), *Lolium* sp. (e.g., *Lolium perenne, Lolium rigidum, Lolium multiflorum* L. var. *Pace*), *Festuca* sp. (e.g., *Festuca* arundinaceae, *Festuca rubra*), *Echinochloa* sp. (e.g., *Echinochloa crus-galli, Echinochloa colona*), *Oxalis* sp. (e.g., *Oxalis stricta, Oxalis pes-caprae, Oxalis corniculata*); *Cyperus* sp. (e.g., *Cyperus difformis, Cyperus esculentum, Cyperus rotundus, Cyperus brevifolius*); *Conyza* sp. (e.g., *Conyza canadensis, Conyza sumatrensis, Conyza bonariensis*); *Sagina* sp. (e.g., *Sagina procumbens*); *Pueraria lobata, Veronica* sp. (e.g., *Veronica hederafolia*), *Stellaria* sp. (e.g., *Stellaria media*), *Rorippa* sp. (e.g., *Rorippa islandica*), *Senecio* sp. (e.g., *Senecio vulgaris*), *Lamium* sp. (e.g., *Lamium amplexicaule*), *Digitaria* sp. (e.g., *Digitaria sanguinalis, Digitaria ischaemum*), *Trifolium* sp. (e.g., *Trifolium repens, Trifolium hirtum, Trifolium incarnatum, Trifolium pratense*), *Alhagi maurorum, Astragalus* spp., *Medicago* sp. (e.g. *Medicago lupulina, Medicago polymorpha*), *Melilotus* sp., *Sesbania* sp. (e.g. *Sesbania punicea, Sesbania exaltata*), *Vicia* sp. (e.g. *Vicia sativa, Vicia villosa*), *Gallium* sp. (e.g., *Gallium aparine*), *Galinsoga* sp. (e.g., *Galinsoga aristatula*), *Cardamine* sp. (e.g., *Cardamine flexuosa, Cardamine hirsuta*), *Kochia* sp. (e.g., *Kochia scoparia*), *Eleusine* sp. (e.g., *Eleusine indica*), *Portulaca* sp. (e.g., *Portulaca oleraceae*), *Plantago* sp. (e.g., *Plantago lanceolata*), *Euphorbia* sp. (e.g., *Euphornia supina, Euphorbia maculate, Euphorbia esula, Euphorbia prostrata*), *Erodium* sp. (e.g., *Erodium cicutarium*), *Sonchus* sp., (e.g., *Sonchus oleraceus*), *Lactuca* sp. (e.g., *Lactuca serriola*), *Capsella* sp. (e.g., *Capsella bursa-pastoris*), *Leptochloa* sp. (e.g., *Leptochloa fascicularis, Leptochloa virgata*), *Raphanus* sp. (e.g., *Raphanus raphanistrum*), *Calandrinia* sp. (e.g., *Calandrinia ciliata*), *Paspalum* sp. (e.g., *Paspalum dilatatum*), *Gnaphalium* sp., *Cynodon* sp. (e.g., *Cynodon dactylon, Cynodon hirsutus*), *Polygonum* sp. (e.g., *Polygonum arenastrum, Polygonum lapathifolium,*), *Avena fatua, Hordeum* sp. (e.g., *Hordeum leporinum*), *Urtica* sp. (e.g., *Urtica urens*), *Tribulus terrestris, Sisymbrium* sp. (e.g., *Sisymbrium irio*), *Cenchrus* sp., *Salsola* sp. (e.g., *Salsola tragus, Salsola kali*), *Amsinckia* sp. (e.g., *Amsinckia lycopsoides*), *Ipomoea* sp., *Claytonia perfoliata, Polypogon* sp. (e.g., *Polypogon monspeliensis*), *Xanthium* sp., *Hypochaeris radicata, Physalis* sp., *Eragrostis* sp., *Verbascum* sp., *Chamomilla suaveolens, Centaurea* sp. (e.g., *Centaurea solstitialis*), *Epilobium brachycarpum, Panicum* sp. (e.g., *Panicum capilare, Panicum dichotomiflorum*), *Rumex acetosella,* *Eclipta* sp. (e.g., *Eclipta alba, Eclipta prostrata*), *Ludwigia* sp., *Urochloa* sp. (e.g. *Urochloa platyphylla, Urochloa panicoides*), *Leersia* sp., *Sesbania* sp. (*Sesbania herbacea*), *Rotala* sp., *Ammania* sp., *Alternathera philoxeroides, Commelina* sp., *Sorghum halepense, Parthenium hysterophorus, Chloris truncata*, and species in the Fabaceae family.

The *Burkholderia* strain, compounds and compositions set forth above may also be used as a fungicide. The targeted fungus may be a *Fusarium* sp., *Botrytis* sp., *Monilinia* sp., *Colletotrichum* sp, *Verticillium* sp.; *Microphomina* sp., *Phytophtora* sp, *Mucor* sp., *Podosphaera* sp. *Rhizoctonia* sp., *Peronospora* sp., *Geotrichum* sp., *Phoma*, and *Penicillium*. In another most particular embodiment, the bacteria are *Xanthomonas*.

The invention will now be described in greater detail by reference to the following non-limiting examples.

EXAMPLES

The compositions and methods set forth above will be further illustrated in the following, non-limiting Examples. The examples are illustrative of various embodiments only and do not limit the claimed invention regarding the materials, conditions, weight ratios, process parameters and the like recited herein.

1. Example 1

Isolation and Identification of the Microbe 1.1 Isolation of the Microorganism The microbe is isolated using established techniques know to the art from a soil sample collected under an evergreen tree at the Rinnoji Temple, Nikko, Japan. The isolation is done using potato dextrose agar (PDA) using a procedure described in detail by Lorch et al., 1995. In this procedure, the soil sample is first diluted in sterile water, after which it is plated in a solid agar medium such as potato dextrose agar (PDA). The plates are grown at 25° C. for five days, after which individual microbial colonies are isolated into separate PDA plates. The isolated bacterium is gram negative, and it forms round, opaque cream-colored colonies that change to pink and pinkish-brown in color and mucoid or slimy over time.

1.2. Identification on the Microorganism

The microbe is identified based on gene sequencing using universal bacterial primers to amplify the 16S rRNA region. The following protocol is used: *Burkholderia* sp A396 is cultured on potato-dextrose agar plates. Growth from a 24 hour-old plate is scraped with a sterile loop and re-suspended in DNA extraction buffer. DNA is extracted using the MoBio Ultra Clean Microbial DNA extraction kit. DNA extract is checked for quality/quantity by running 5 μl on a 1% agarose gel.

PCR reactions are set up as follows: 2 μl DNA extract, 5 μl PCR buffer, 1 μl dNTPs (10 mM each), 1.25 μl forward primer (27F; 5'-AGAGTTTGATCCTGGCTCAG-3' (SEQ ID NO:1), 1.25 μl reverse primer (907R; 5'-CCGTCAATTCCTTTGAGTTT-3' (SEQ ID NO:2)) and 0.25 μl Taq enzyme. The reaction volume is made up to 50 μl using sterile nuclease-free water. The PCR reaction includes an initial denaturation step at 95° C. for 10 minutes, followed by 30 cycles of 94° C./30 sec, 57° C./20 sec, 72° C./30 sec, and a final extension step at 72° C. for 10 minutes.

The product's approximate concentration and size is calculated by running a 5 μl volume on a 1% agarose gel and comparing the product band to a mass ladder.

Excess primers, dNTPs and enzyme are removed from the PCR product with the MoBio PCR clean up kit. The cleaned PCR product as directly sequenced using primers 27F (same as above), 530F (5'-GTGCCAGCCGCCGCGG-3' (SEQ ID NO:3)), 1114F (5'-GCAACGAGCGCAACCC (SEQ ID NO:4)) and 1525R (5'-AAGGAGGTGWTCCARCC-3' (SEQ ID NO:5)), 1100R (5'-GGGTTGCGCTCGTTG-3' (SEQ ID NO:6)), 519R (5'-GWATTACCGCGGCKGCTG-3' (SEQ ID NO:7).

The 16S rRNA gene sequence of strain A396 is compared with the available 16s rRNA gene sequences of representatives of the β-proteobacteria using BLAST. Strain A395 A396 is closely related to members of the *Burkholderia cepacia* complex, with 99% or higher similarity to several isolates of *Burkholderia multivorans, Burkholderia vietnamensis*, and *Burkholderia cepacia*. A BLAST search excluding the *B. cepacia* complex, showed 98% similarity to *B. plantarii, B. gladioli* and *Burkholderia* sp. isolates.

A distance tree of results using the neighbor joining method, showed that A396 is related to *Burkholderia multi-* vorans and other *Burkholderia cepacia* complex isolates. *Burkholderia plantarii* and *Burkholderia glumae* grouped in a separate branch of the tree.

The isolated *Burkholderia* strain was found to contain the following sequences: forward sequence, DNA sequence with 27F primer, 815 nucleotides (SEQ ID NO:8); reverse sequence, 1453 bp, using primers 1525R, 1100R, 519R (SEQ ID NO:9); reverse sequence 824 bp using primer 907R (SEQ NO: 10); forward sequence 1152 bp using primer 530F (SEQ ID NO:11); forward sequence 1067 bp using 1114F primer (SEQ ID NO:12); reverse sequence 1223 bp using 1525R primer (SEQ NO:13); reverse sequence 1216 bp using 1100R primer (SEQ ID NO:14); reverse sequence 1194 bp using 519R primer (SEQ ID NO:15).

1.3. Proof that *Burkholderia* A396 does not Belong to *Burkholderia cepacia* Complex 1.3.1 Molecular Biology Work Using Specific PCR Primers In order to confirm the identification of *Burkholderia* A396 as *Burkholderia multivorans*, additional sequencing of housekeeping genes is performed. *Burkholderia multivorans* is a known member of the *Burkholderia cepacia* complex. Efforts are focused on PCR of recA genes, as described by Mahenthiralingam et al., 2000. The following primers are used: (a) BCR1 and BCR2 set forth in Mahenthiralingam et al., 2000 to confirm *B. cepacia* complex match and (b) BCRBM1 and BCRBM2 set forth Mahenthiralingam et al, 2000 to confirm *B. multivorans* match. A product-yielding PCR reaction for the first primer set would confirm that the microbe belongs to the *B. cepacia* complex. A product-yielding PCR reaction for the second primer set would confirm that the microbe is indeed *B. multivorans*.

No PCR product is obtained for either pair of primers. The performance of the PCR reaction and primers is tested using *Burkholderia multivorans* ATCC 17616 (positive control) and *Pseudomonas fluorescens* (negative control). Strong bands are observed both for *B. multivorans* using both sets of primers. No bands are observed for *Pseudomonas fluorescens*. The results indicate that A396 is a *Burkholderia*, but not a member of the *B. cepacia* complex, and not *Burkholderia multivorans*. This is also demonstrated in a comparative culture experiment in which both A396 and a type culture of *B. multivorans* are grown side-by-side in a shake culture, and the growth is monitored daily using optical density measurements at 600 nm. Under the set conditions, the novel species A396 grew much faster than the *B. multivorans* type strain (FIG. 1).

1.3.2 DNA-DNA Hybridization

In order to confirm that isolate A396 is a new species of *Burkholderia*, a DNA-DNA hybridization experiment with *Burkholderia multivorans* (the closest 16S rRNA sequence match) is conducted. Biomass for both A396 and *B. multivorans* is produced in ISP2 broth, grown over 48 hours at 200 rpm/25° C. in Fernbach flasks. The biomass is aseptically harvested by centrifugation. The broth is decanted and the cell pellet is resuspended in a 1:1 solution of water: isopropanol. DNA-DNA hybridization experiments are performed by the DSMZ, the German Collection of Microorganisms and Cell Cultures in Germany. DNA is isolated using a French pressure cell (Thermo Spectronic) and is purified by chromatography on hydroxyapatite as described by Cashion et al., 1977. DNA-DNA hybridization is carried out as described by De Ley et al., 1970 under consideration of the modifications described by Huss et al., 1983 using a model Cary 100 Bio UV/VIS-spectrophotometer equipped with a Peltier thermostatted 6×6 multicell changer and a temperature controller with in-situ temperature probe (Varian). DSMZ reported % DNA-DNA similarly between A396 and *Burkholderia multivorans* of 37.4%. The results indicate that *Burkholderia* sp strain A396 does not belong to the species *Burkholderia multivorans* when the recommendations of a threshold value of 70% DNA-DNA similarity for the definition of bacterial species by the ad hoc committee (Wayne et al., 1987) are considered.

1.4. Biochemical Profile Using Biolog GN2 Plates

For the carbon source utilization profile, A396 is grown overnight on Potato Dextrose Agar (PDA). The culture is transferred to BUG agar to produce an adequate culture for Biolog experiments as recommended by the manufacturer (Biolog, Hayward, Calif.).

The biochemical profile of the microorganism is determined by inoculating onto a Biolog GN2 plate and reading the plate after a 24-hour incubation using the MicroLog 4-automated microstation system. Identification of the unknown bacteria is attempted by comparing its carbon utilization pattern with the Microlog 4 Gram negative database.

No clear definitive matches are found to the Biolog profile. The closest matches all had less than 35% similarity with A396: *Pseudomonas spinosa* (*Burkholderia*), *Burkholderia cepacia*, and *Burkholderia pseudomallei*. The results are shown in Table I.

TABLE 1

Biochemical Profile of A396

| Substrate | Result | Substrate | Result |
|---|---|---|---|
| Cyclodextrin | − | L-arabinose | − |
| Dextrin | − | D-arabitol | − |
| Glycogen | − | D-cellobiose | − |
| Tween 40 | + | Erythritol | − |
| Tween 80 | + | D-Fructose | − |
| N-acetyl-D-Galactoseamine | − | L-Fucose | − |
| N-acetyl-D-glucosamine | − | D-Galactose | +/− |
| Adonitol | − | Gentibiose | − |
| Succinic Acid Mon-methyl ester | − | D-Glucose | + |
| Acetic acid | − | m-Inositol | − |
| Cis-aconitic acid | − | D-Lactose | − |
| Citric acid | − | Lactulose | − |
| Formic acid | + | Maltose | − |
| D-Galactonic Acid Lactone | − | D-Mannitol | − |
| D-Galacturonic Acid | − | D-Mannose | − |
| D-Gluconic acid | − | D-Melibiose | − |
| D-Glucosaminic acid | − | β-methyl-D-glucoside | − |
| D-Glucuronic Acid | − | D-Psicose | − |
| α-hydroxyburytic acid | − | D-Raffinose | − |
| β-hydroxybutyric acid | + | L-Rhamonose | − |
| γ-hydroxybutyric acid | − | D-Sorbitol | − |
| p-hydroxyphenylacetic acid | − | Sucrose | − |
| Itaconic acid | − | D-Trehalose | + |
| α-keto butyric acid | − | Turanose | − |
| α-keto glutaric acid | − | Xylitol | − |
| α-ket valeric acid | − | Pyruvic Acid Methyl esther | − |
| D,L-Lactic acid | − | Uridine | − |
| Malonic acid | − | Thymidine | − |
| Propionic acid | + | Phenyethyl-amine | − |
| Quinic acid | − | Putrescine | − |
| D-Saccharic acid | − | 2-aminoethanol | − |
| Sebacic acid | − | 2,3-Butanediol | − |
| Succinic Acid | + | Glycerol | +/− |
| Bromosuccinic acid | − | D,L-a-glycerol phosphate | +/− |
| Succinamic acid | − | α-D-Glucose-1-phosphate | − |
| Glucuronamide | − | D-glucose-6-phosphate | + |
| L-alaninamide | + | γ-amino butyric acid | + |
| D-Alanine | − | Urocanic acid | − |
| L-alanine | + | Inosine | − |
| L-alanyl-glycine | − | L-phenylalanine | + |
| L-asparagine | + | L-proline | − |

TABLE 1-continued

Biochemical Profile of A396

| Substrate | Result | Substrate | Result |
|---|---|---|---|
| L-aspartic acid | +/− | L-pyroglutamic acid | − |
| L-glutamic acid | + | D-serine | − |
| Glycyl-L-Aspartic acid | − | L-serine | − |
| Glycyl-L-glutamic acid | − | L-threonine | − |
| L-histidine | − | D,L-carnitine | − |
| Hydroxy-L-proline | + | L-ornithine | − |
| L-leucine | − | | |

1.5. Fatty Acid Composition

After incubation for 24 hours at 28° C., a loopful of well-grown cells are harvested and fatty acid methyl esters are prepared, separated and identified using the Sherlock Microbial Identification System (MIDI) as described (see Vandamme et al., 1992). The predominant fatty acids present in the Burkholderia A396 are as follows: 16:0 (24.4%), cyclo 17:0 (7.1%), 16:0 3-OH (4.4%), 14:0 (3.6%), 19:0 ω8c (2.6%) cyclo, 18:0 (1.0%). Summed feature 8 (comprising 18:1 ω7c) and summed feature 3 (comprising of 16:1 ω7c and 16:1 ω6c) corresponded to 26.2% and 20.2% of the total peak area, respectively. Summed feature 2 comprising 12:0 ALDE, 16:1 iso I, and 14:0 3-OH) corresponded to 5.8% of the total peak area while summed feature 5 comprising 18:0 ANTE and 18:2 ω-6,9c corresponded to 0.4%. Other fatty acids detected in A396 in minor quantities included: 13:1 at 12-13 (0.2%), 14:1 ω5c (0.2%), 15:0 3-OH (0.13%), 17:1 ω7c (0.14%), 17:0 (0.15%), 16:0 iso 3-OH (0.2%), 16:0 2-OH (0.8%), 18:1 ω7c 11-methyl (0.15%), and 18:1 2-OH (0.4%).

A comparison of the fatty acid composition of A396 with those of known microbial strains in the MIDI database suggested that the fatty acids in the novel strain A396 were most similar with those of *Burkholderia cenocepacia*.

1.6 Resistance to Antibiotics

Antibiotic susceptibility of *Burkholderia* A396 is tested using antibiotic disks on Muller-Hinton medium as described in PML Microbiological's technical data sheet #535. Results obtained after 72-hour incubation at 25° C. are presented in Table 2 below.

TABLE 2

Susceptibility of MBI-206 to various antibiotics.

| | Concentration (ug) | Susceptible |
|---|---|---|
| Tetracycline | 30 | − |
| Kanamycin | 30 | +++ |
| Erythromycin | 15 | − |
| Streptomycin | 10 | − |
| Penicillin | 10 | − |
| Ampicillin | 10 | − |
| Oxytetracycline | 30 | − |
| Chloramphenicol | 30 | ++ |
| Ciprofloxacin | 5 | ++ |
| Gentamicin | 10 | − |
| Piperacillin | 100 | +++ |
| Cefuroxime | 30 | − |
| Imipenem | 10 | +++ |
| Sulphamethoxazole-Trimethoprim | 23.75/25 | ++ |

+++ very susceptible,
++ susceptible,
− resistant

The results indicate that the antibiotic susceptibility spectrum of *Burkholderia* A396 is quite different from pathogenic *B. cepacia* complex strains. *Burkholderia* A396 is susceptible to kanamycin, chloramphenicol, ciprofloxacin, piperacillin, imipenem, and a combination of sulphamethoxazole and trimethoprim. As a comparison, Zhou et al., 2007 tested the susceptibility of 2,621 different strains in *B. cepacia* complex isolated from cystic fibrosis patients, and found that only 7% and 5% of all strains were susceptible to imipenem or ciprofloxacin, respectively. They also found 85% of all strains to be resistant to chloramphenicol (15% susceptible), and 95% to be resistant (5% susceptible) to the combination of sulphamethoxazole and trimethoprim. Results of Zhou et al., 2007 are similar to those of Pitt et al., 1996 who determined antibiotic resistance among 366 *B. cepacia* isolates and reported that most of them are resistant to ciprofloxacin, cefuroxime, imipenem, chloramphenicol, tetracycline, and sulphametoxacole.

2. Example 2

*Burkholderia* sp. as an Herbicide 2.1 Study #1

To confirm the activity found in the initial herbicide screen, an in vivo study is conducted using the Amberlite 7 XAD resin extract derived from a 5-day old whole cell broth of the novel *Burkholderia* species. The dried crude extract is resuspended in 4% ethanol and 0.2% non-ionic surfactant (glycosperse) at a concentration of 10 mg/mL, and further diluted to a concentration of 5.0 mg/mL. The two samples are sprayed on 4-week old plants of bindweed (*Convolvulus arvensis*), and the plants are kept under growth lights at 25° C. for 2 weeks, at which point, the phytotoxicity evaluations are performed. In the same study, 2-week old redroot pigweed plants are sprayed with increasing concentrations of the crude extract derived from the bacterial culture. The test concentrations are 1.25, 2.5, 5.0 and 10.0 mg/mL, and the plants are incubated as described above before phytotoxicity evaluations.

Figure 2:
Figure 3:
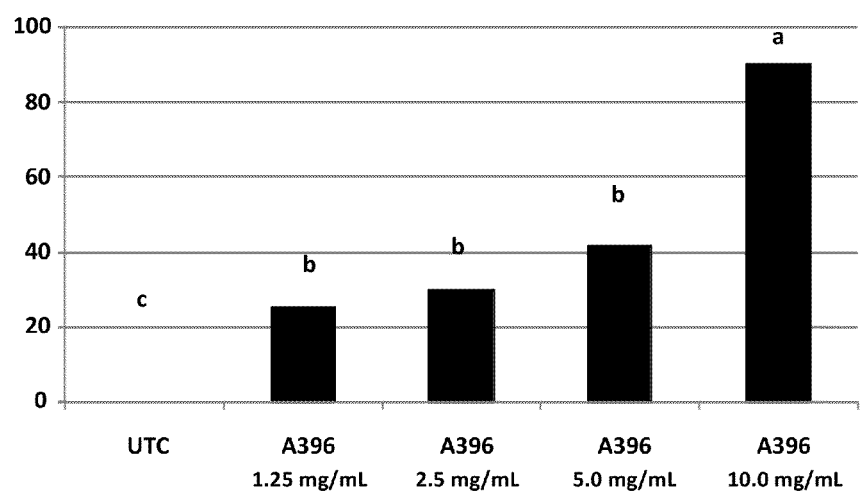
Figure 4:
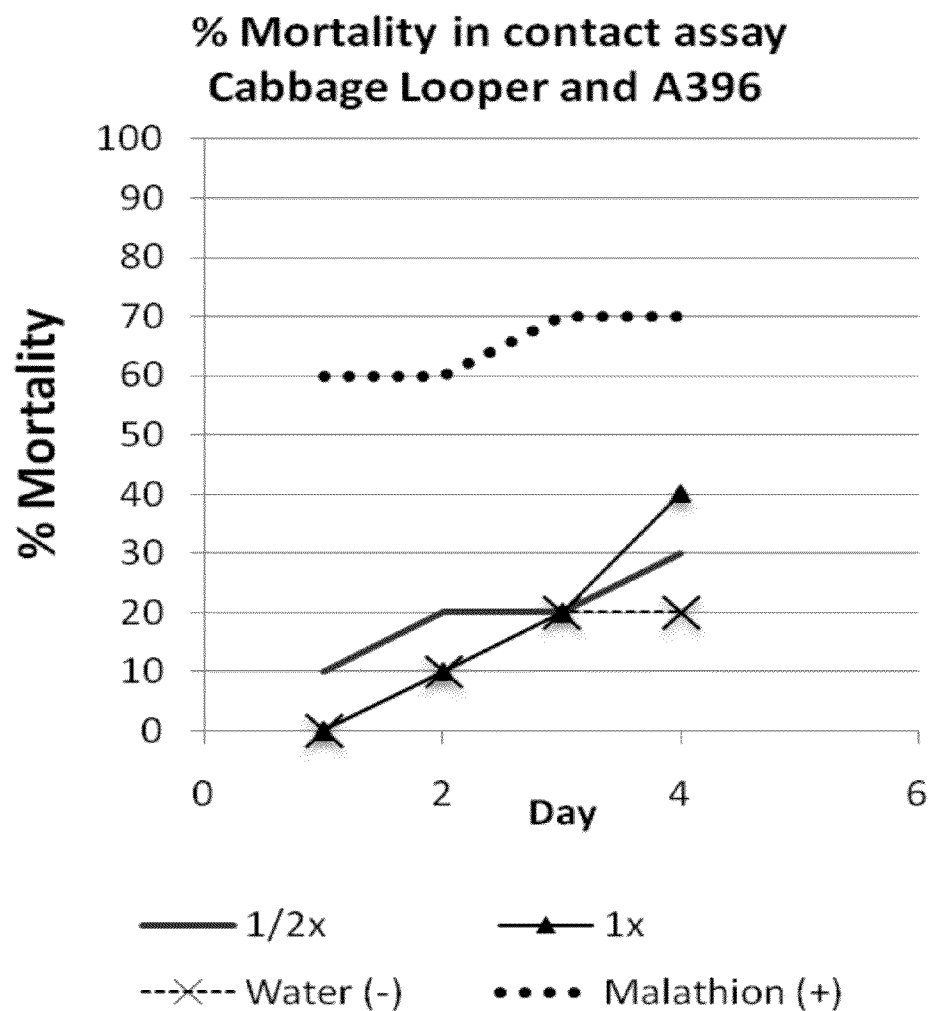
Figure 5:
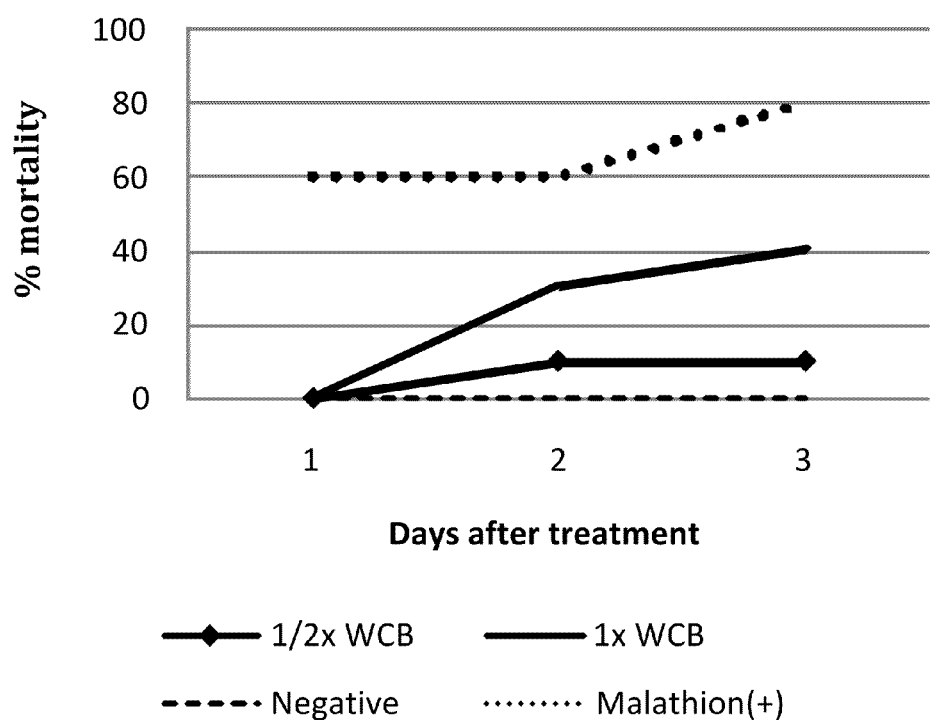
Figure 6:
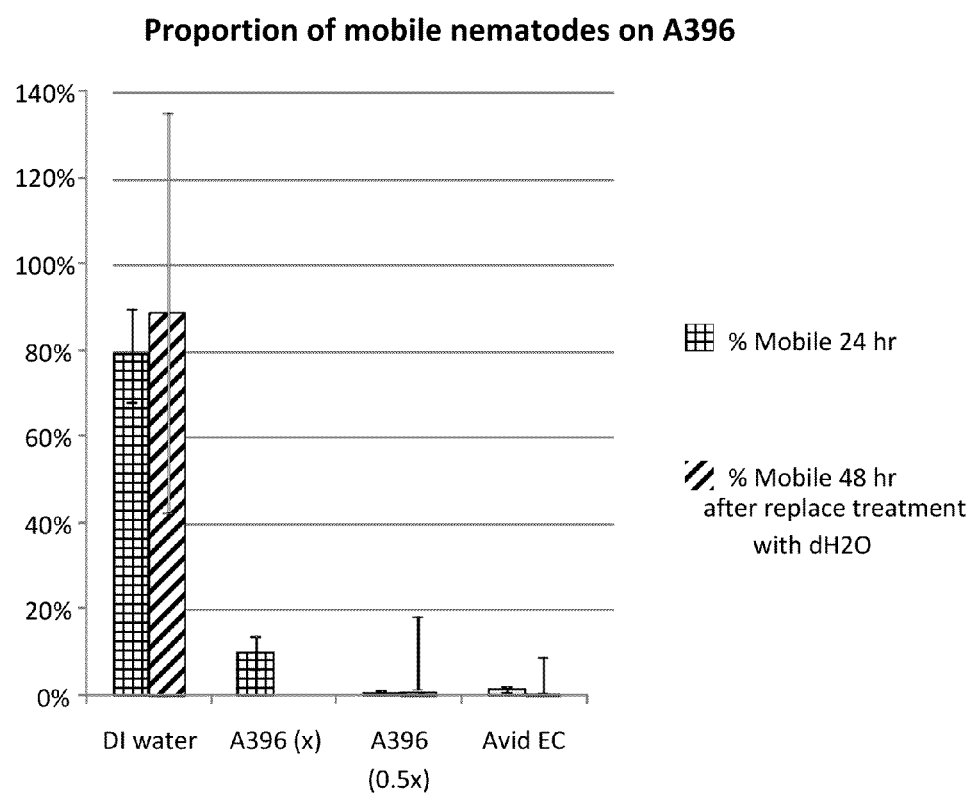

Results presented in FIG. 2 (bindweed) and 3 (pigweed) show the phytotoxic effect of *Burkholderia* crude extract at different concentrations, and they show good herbicidal effect on pigweed even at low treatment concentrations. Both extract treatments (5 and 10 mg/mL) result in stunting on bindweed.

2.2 Study #2

A novel strain of *Burkholderia* sp. A396 is grown in an undefined mineral medium for 5 days (25° C., 200 rpm). The whole cell broth is extracted using XAD7 resin. The dried crude extract is resuspended in 4% ethanol and 0.2% non-ionic surfactant at a concentration of 10 mg/mL, and further diluted to concentrations of 5.0, 2.5, and 1.25 mg/mL. All four test solutions are then tested on the following broadleaf and grass weed species listed in Table 3:

TABLE 3

Broadleaf and Grass Weed Species Tested

| Common Name | Scientific Name |
|---|---|
| Lambsquarter | *Chenopodium album* |
| Horseweed | *Conyza canadensis* |
| Curlydock | *Rumex crispus* |
| Crabgrass | *Digitaria sanguinalis* |
| Bluegrass | *Poa annua* |
| Dandelion | *Taraxacum officinale* |
| Nightshade | *Solanum nigrum* |
| Mustard | *Brassica kaber* |
| Mallow | *Malva neglecta* |
| Cocklebur | *Xanthium pensylvanicum* |
| Bermuda Grass | *Cynodon dactylon* |

TABLE 3-continued

| Broadleaf and Grass Weed Species Tested | |
|---|---|
| Common Name | Scientific Name |
| Foxtail | *Setaria lutescens* |
| Sowthistle | *Sonchus oleraceus* |

A solution of 0.2% glycosperse and Roundup at 6 fl oz per gallon rate is used as negative and positive controls, respectively.

All plant species are tested in 4"×4" plastic pots in three replicates. The untreated control plants are sprayed with the carrier solution (4% Ethanol, 0.2% glycosperse) and the positive control plants with Roundup at a rate corresponding to 6 fl. oz/acre. Treated plants are kept in a greenhouse under 12 h light/12 h dark conditions. Phytotoxicity data taken 22 days after treatment for species #1-8 and 12 days for species #9-12 are presented in Tables 5 and 6, respectively. The rating scale for both tables is shown in Table 4:

TABLE 4

| Rating Scale | |
|---|---|
| Rating Scale | % Control |
| 0 | 0 |
| 1 | <10 |
| 2 | 25 |
| 3 | 50 |
| 4 | 75 |
| 5 | 100 |

In a separate experiment, using the same design as described above, systemic activity is tested. A 10 mg/ml crude extract supernatant of *Burkholderia* sp. A396 is painted onto first true leaves of Ragweed, Mustard, Nightshade, Crabgrass, Wheat and Barnyard Grass. Seedlings are evaluated 7 days after treatment. Observed symptoms include: burning, warping, bleaching Herbicidal activity is observed in the next leaf above the treated leaf in Ragweed, Mustard and Nightshade. No systemic activity is observed in the tested grasses. In a second experiment. five fractions of the same crude extract (10 mg/ml) are evaluated using the same experimental design as described above. Seedlings of Mustard, Wheat and Crabgrass are treated. Seven and 20 days after treatment, symptoms of herbicidal activity are observed in Mustard from four out of the five fractions (091113B4F6, 091113B4F7, 091113B4F8 and 091113B4F9) using a C-18 column (Phenomenex Sepra C18-E, 50 μm, 65 Å). Symptoms are observed in the next leaf above the treated leaf. No systemic activity is observed in the tested grasses.

3. Example 3

*Burkholderia* sp. as an Insecticide

3.1. Contact Activity Studies

The following assay is used in the initial screening phase to determine if the compounds derived from a culture of the novel *Burkholderia* species has contact activity against a Lepidopteran pest (larvae). It is further used as a tool for the bioassay-guided fractionation to determine the active fractions and peaks derived from the whole-cell-broth extract. The test is conducted in individual 1.25 oz plastic cups using

TABLE 5

| Phytotoxicity Data for Species #1-8 | | | | | | | | |
|---|---|---|---|---|---|---|---|---|
| Treatment | Horseweed | Lambsquarter | Dandelion | Curlydock | Crabgrass | Mustard | Nightshade | Bluegrass |
| UTC | 0.0 | 0.0 | 0.0 | 0.0 | 0.0 | 0.7 | 0.0 | 0.0 |
| 1.25 mg/mL | 0.0 | 4.7 | 0.0 | 0.0 | 0.0 | 4.3 | 0.0 | 0.0 |
| 2.5 mg/mL | 0.7 | 4.5 | 0.0 | 0.0 | 0.0 | 4.7 | 0.0 | 0.0 |
| 5.0 mg/mL | 4.3 | 5.0 | 0.0 | 0.0 | 0.0 | 5.0 | 0.0 | 0.0 |
| 10.0 mg/mL | 4.7 | 5.0 | 0.0 | 0.0* | 0.0 | 5.0 | 1.5 | 0.0 |
| Roundup | 5.0 | 5.0 | 5.0 | 5.0 | 5.0 | 5.0 | 5.0 | 5.0 |

*stunting that resulted in plants approximately half the size of untreated plants

TABLE 6

| Phytotoxicity Data for Species #9-12 | | | | | |
|---|---|---|---|---|---|
| Treatment | Cocklebur | Foxtail | Bermuda Grass | Sowthistle | Mallow |
| UTC | 0.0 | 0.7 | 0.0 | 0.0 | 2.8 |
| 1.25 mg/mL | 0.5 | 0.3 | 0.3 | 0.0 | 2.0 |
| 2.5 mg/mL | 0.5 | 0.7 | 0.5 | 0.0 | 2.7 |
| 5.0 mg/mL | 0.8 | 0.3 | 0.2 | 0.0 | 2.2 |
| 10.0 mg/mL | 0.7 | 0.7 | 0.3 | 0.2 | 1.7 |
| Roundup | 4.7 | 4.8 | 4.7 | 5.0 | 5.0 |

Based on the results obtained in these studies, the compounds extracted from fermentation broths of the isolated *Burkholderia* species had herbicidal activity against several weed species are tested. Of the twelve species tested, Lambsquarters and mustard are most susceptible, followed by mallow and horseweed. Extract concentration as low as 1.25 mg/mL is able to provide almost complete control of Lambsquarters and mustard, whereas higher concentration is required for the mallow and horseweed.

either Cabbage looper (*Tricoplusia ni*) late third instar larvae or Beet Armyworm (*Spodoptera exigua*) early third instar larvae. A 1 cm×1 cm piece of solid Beet armyworm diet is placed in the center of each cup together with one larvae. A 1 μl aliquot of each treatment (whole cell broth or extract from a 5-day-old *Burkholderia* A396 culture) is injected on each larvae thorax (dorsal side) using a Hamilton Precision Syringe. Each treatment is replicated ten times. Water is used as a negative control treatment and malathion as the positive control treatment. After injection, each cup is covered with parafilm with an airhole, and the cups are incubated for three days at 26° C. Mortality evaluations are done daily, starting 24 hours after the treatment.

FIGS. 4 and 5 present the results from contact activity tests. According to the results, the filter-sterilized broth from a *Burkholderia* sp culture killed about 40% of all test insects within 3 days. Diluted broth (50%) has lower activity, resulting in about 10% control in both insects tested.

3.2. Activity Against Larvae Through Feeding

Direct toxicity via feeding is tested using the diet-overlay tests with following 96-well plate assay format using microtiter plates with 200 µl of solid, artificial Beet Armyworm diet in each well. One hundred (100) microliters of each test sample is pipetted on the top of the diet (one sample in each well), and the sample is let dry under flowing air until the surface is dry. Each sample (filter-sterilized through a 0.2 micron filter) is tested in six replicates, and water and a commercial Bt (*B. thuringiensis*) product are used as negative and positive controls, respectively. One third instar larvae of the test insect (Cabbage looper—*Trichoplusia ni*; Beet armyworm—*Spodoptera exiqua*; Diamondback Moth—*Plutella xylostella*) is placed in each well, and the plate is covered with plastic cover with airholes. The plates with insects are incubated at 26° C. for 6 days with daily mortality evaluations.

FIG. 5 represents data from a diet overlay study with Beet Armyworm (*Spodoptera exigua*) early third instar larvae tested at four different broth concentrations: 1× (100%), ¼× (25%), ⅛× (12.5%), 1/16× (6.125%). The data shows that the undiluted, filter-sterilized broth is able to give 100% control at the end of the 7-day incubation period. Similar control is obtained with a 4-fold dilution of the broth, and in the end of the study, both undiluted and 4-fold diluted broths are comparable to Bt used as a positive control. However, the effect of Bt is significantly faster than that of the *Burkholderia* broths. Efficacy against armyworm larvae is dependent on broth concentration, and the two lowest broth concentrations (12.5% and 6.125%) provided less control than the two highest ones. However, the performance of the 12.5% dilution is not much lower than the 25% dilution. The 16-fold dilution of broth is clearly not efficient enough, and it only provided partial (33%) control of armyworm larvae during this 7-day study. The corresponding mortality rates for the same broth dilution used on cabbage loopers and diamondback moth larvae are a little higher with 6.125% broth killing 80% and 50% of larvae, respectively.

3.3. In Vitro Activity Against Sucking Insects

Five stinkbug (*Euschistus* sp.) adults are placed in each 16 oz plastic container lined with a piece of paper towel. A microcentrifuge tube containing 2 mL of each test sample (filter sterilized whole broth) is capped with a cotton ball, and laid down on the bottom of the plastic container. One sunflower seed is placed next to the tube as bait. Water and a commercial product with a mixture of pyrethrin and PBO at a recommended rate are used as negative and positive controls, respectively. Each container is closed with a lid, and they are incubated at 25° C. for 7 days with daily mortality checks.

Results are presented below in Table 7 and they show about 80% control of sucking insect (stinkbug) by day 7 in this in vitro system with 50% diluted broth. In this study, the diluted fermentation broth of *Burkholderia* A396 is more effective in controlling stinkbugs than the commercial product used as a positive control. Interestingly, the non-diluted broth resulted in lower insect control, which might be an indication of antifeedant (feeding inhibition) properties of the active secondary metabolites produced by this new species of *Burkholderia*.

TABLE 7

Effect of A396 on Stinkbugs

| Treatment | % control (Day 3) | % control (Day 5) | % control (Day 7) |
|---|---|---|---|
| A396 undil. broth (1x) | 0 | 0 | 40 |
| A396 broth dil. 50% (0.5x) | 20 | 20 | 80 |
| Pyrethrin + PBO (pos control) | 0 | 0 | 40 |
| Water (neg control) | 0 | 0 | 0 |

4. Example 4

Sucking Insect Test In Vivo

The in vivo efficacy of the filtered whole cell broth is tested in a plant assay with mustard plants and green peach aphid (*Myzus persicae*) as the test insect. Approximately one-month-old Florida Broadleaf mustard (*Brassica* sp.) plants are sprayed with two different concentrations (1× and 0.5×) of the filter sterilized whole cell broth of *Burkholderia* sp. using a Paasche airbrush. Water and a commercial product of avermectin (Avid) are used as negative and positive controls, respectively. The plants are allowed to dry on the benchtop, after which they are placed in a 6-cup plastic container with a lid with airholes. Ten aphids at various developmental stages are placed on each test plant, and the plants are incubated under growth lamps for 7 days at 25° C. Daily evaluations for the number of aphids on each plant (summarized in table Table 8 below) are made and recorded in a notebook.

TABLE 8

In vivo Efficacy of A396 on Green Peach Aphids

| Treatment | # live aphids Day 0 | # live aphids Day 2 | # live aphids Day 4 | # live aphids Day 7 |
|---|---|---|---|---|
| A396 undiluted broth (1x) | 10 | 36 | 88 | 145 |
| A396 broth diluted (0.5x) | 10 | 47 | 138 | 217 |
| Avermectin (pos control) | 10 | 0 | 0 | 0 |
| Water (neg control) | 10 | 140 | 364 | 393 |

According to the results, both concentrations of the filter-sterilized broth derived from a culture of a novel species of *Burkholderia* are able to control the population growth of a sucking insect, *M. persicae*.

5. Example 5

Nematocidal Activity 5.1 Study #1

To assess the effect of filter-sterilized *Burkholderia* sp A396 culture broth on the motility (and subsequent recovery) of juvenile (J2) root-knot nematodes (*Meloidogyne incognita* VW6), the following test is conducted on 24-well plastic cell-culture plates:

A 300-ul aliquot of each test solution (either 1× or 0.5× filter-sterilized broth) is added into appropriate wells after which, fifteen nematodes dispensed in 10 μl of DI water are added into each well, plate is closed with a lid, and incubated at 25° C. for 24 hours. Water and Avid at 20,000× dilution are used as negative and positive controls, respectively. Effect of each compound on nematode mobility is checked after 24 hours by probing each nematode with a needle, and the proportion of immobile nematodes in each treatment is recorded in a notebook using a % scale. To assess the recovery of mobility in each treatment, a volume of 200 μl is removed from each well, and the remaining solution in each well is diluted by adding 2 mL of DI water. Plates are again incubated for 24 hours as described above, after which the second mobility evaluation is performed.

The results presented in FIG. 6 show the filter-sterilized broth at both test concentrations can immobilize the free-living juvenile root-knot nematodes. This effect lasts at least for 24-hours, which suggests that *Burkholderia* A396 broth can be used to prevent plants from nematode infections.

5.2 Study #2

Materials and Methods

Mini Drench Test: *Burkholderia* A396 whole cell broth is tested in a greenhouse assay conducted in 45 ml pots. Cucumber seeds cv. Toshka are sown directly into pots filled with a sandy loam soil. Ten days later, pots were each treated with 5 ml of a suspension. Specific amounts used are shown in Table 9:

TABLE 9

| Compounds | *Burkholderia* strain A396 |
|---|---|
| | Fosthiazate (Standard, EC 150) (positive control) |
| Test species | *Meloidogyne* sp. applied at 3000 eggs per mini drench pot (in 2 ml) |
| Test plant | *Cucumis sativus* (cucumber cv. Toschka) |
| Test formulation | 100% liquid formulation |
| Test concentrations | 100, 50, 25, 12.5, 6, 3, 1.5 ml/L |
| Test application | Drench application |

Figure 9:
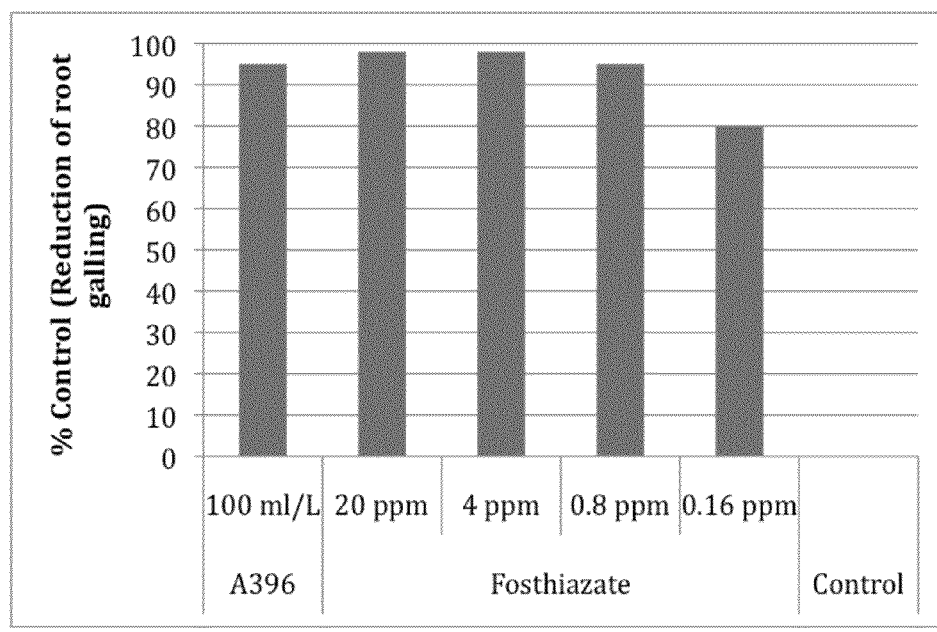
Figure 10:
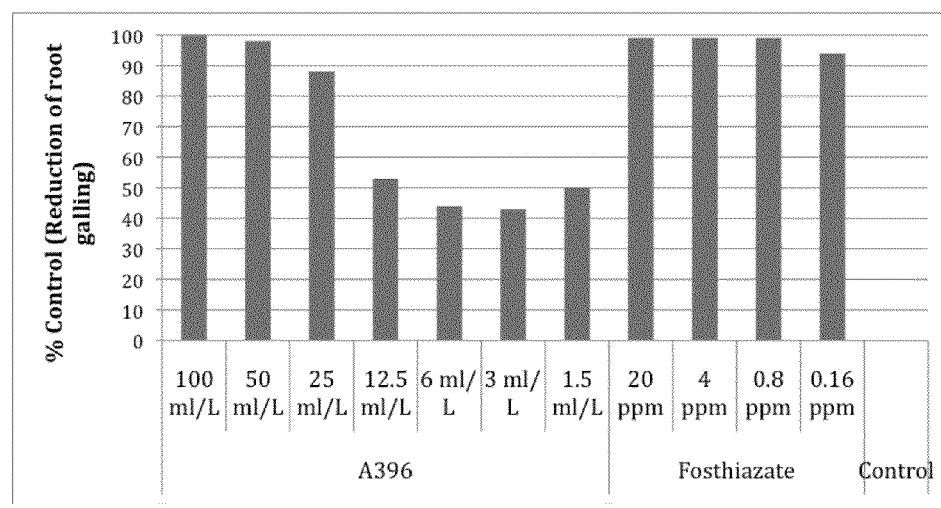

As indicated in Table 9, pots are inoculated with 3000 eggs of *M. incognita*. Four replicates were prepared for each treatment and rate. The trial was harvested fourteen days after trial application and inoculation. Root galling was assessed according to Zeck's gall index (Zeck, 1971). Phytotoxicity was measured as a reduction of root galling in comparison to the control. The results are shown in FIGS. 9 and 10.

In Mini Drench Test no. 1 (see FIG. 9), the activity of the treatment was very high and a reduction of almost 100% was observed when applied at a concentration of 100 ml/L *Burkholderia* A396. Fosthiazate performed as usual (100% control at 20 ppm).

In Mini Drench Test no. 2 (see FIG. 10) a 100% reduction of root galling was achieved at the highest concentration of 100 ml/L dropping to approximately 50% at 1.5 ml/L. Fosthiazate performed as usual (100% control at 20 ppm).

5.3 Study #3

To demonstrate the nematicidal activity of *Burkholderia* A396, a greenhouse study on cucumber (*Cucumis sativus*) is performed using a whole cell broth of *Burkholderia* A396 as the test product to control root knot nematodes (*Meloidogyne incognita*). One cucumber plant per pot is planted in soil and grown in a greenhouse under artificial lights at 28° C. Each pot with a plant is treated with an aliquot (about 80 mL) of either the undiluted test product or a test product diluted to 5% with water. Each *Burkholderia* A396 treatment as well as a positive control treatment with Temik (at a label rate) and a negative control with no additions consisted of five replicates. Plants are grown in a greenhouse for 60 days, after which each plant was harvested and evaluated for fresh shoot and root weights. Number of nematode eggs in each pot was recorded and a parameter indicating the number of eggs per a gram of root mass was calculated. Statistical analysis (ANOVA) is performed, and the statistical differences among treatment means at $p<0.1$ was calculated. Data presented in Table 10 below shows that even though not statistically different from the untreated control, the pots treated with A396 whole cell broth contained less nematode eggs than the untreated control pots. The effect calculated as number of eggs per root mass is more clear when undiluted broth is used as a treatment.

TABLE 10

The effect of A396 whole cell broth on the cucumber shoot and root weight, total number of *M. incognita* eggs per pot and the number of eggs per gram of root mass.

| | shoot fresh wt | root fresh wt | # of eggs | # of eggs/g of root |
|---|---|---|---|---|
| untreated | 15.22 b | 11.76 bc | 67693 a | 5252.0 ab |
| A396 5% v/v | 11.89 b | 6.914 c | 56084 a | 8419.4 a |
| A 396 undiluted | 15.66 b | 11.09 bc | 40463 a | 3929.2 ab |
| Temik 15 G 5 lb/a | 29.54 a | 29.74 a | 68907 a | 2604.4 b |
| LSD at p < 0.1 | 5.34 | 6.9879 | 36509.2 | 3317.07 |

6. Example 6

Isolation of Templazole A and B

Methods and Materials

The following procedure is used for the purification of Templazole A and B extracted from cell culture of *Burkholderia* sp (see FIG. 7):

The culture broth derived from the 10-L fermentation *Burkholderia* (A396) in Hy soy growth medium is extracted with Amberlite XAD-7 resin (Asolkar et al., 2006) by shaking the cell suspension with resin at 225 rpm for two hours at room temperature. The resin and cell mass are collected by filtration through cheesecloth and washed with DI water to remove salts. The resin, cell mass, and cheesecloth are then soaked for 2 h in acetone after which the acetone is filtered and dried under vacuum using rotary evaporator to give the crude extract. The crude extract is then fractionated by using reversed-phase C18 vacuum liquid chromatography ($H_2O$/$CH_3OH$; gradient 90:20 to 0:100%) to give 10 fractions. These fractions are then concentrated to dryness using rotary evaporator and the resulting dry residues are screened for biological activity using 96 well plate lettuce seeding assay. The active fractions are then subjected to reversed phase HPLC (Spectra System P4000 (Thermo Scientific) to give pure compounds, which are then screened in above mentioned bioassays to locate/identify the active compounds. To confirm the identity of the compound, additional spectroscopic data such as LC/MS and NMR is recorded.

The active fraction 4 is purified further by using HPLC C-18 column (Phenomenex, Luna 10u C18(2) 100 A, 250×30), water:acetonitrile gradient solvent system (0-10 min; 80% aqueous $CH_3CN$, 10-25 min; 80-65% aqueous $CH_3CN$, 25-50 min; 65-50% aqueous $CH_3CN$, 50-60 min; 50-70% $CH_3CN$, 60-80 min; 70-0% aqueous $CH_3CN$, 80-85 min; 0-20% aqueous $CH_3CN$) at 8 mL/min flow rate and UV detection of 210 nm, to give templazole B, retention time 46.65 min. The other active fraction 6 is also purified using HPLC C-18 column (Phenomenex, Luna 10u C18(2) 100 A, 250×30), water:acetonitrile gradient solvent system (0-10 min; 80% aqueous $CH_3CN$, 10-25 min; 80-60% aqueous $CH_3CN$, 25-50 min; 60-40% aqueous $CH_3CN$, 50-60 min; 40% $CH_3CN$, 60-80 min; 40-0% aqueous $CH_3CN$, 80-85 min; 0-20% aqueous $CH_3CN$) at 8 mL/min flow rate and UV detection of 210 nm, to give templazole A, retention time 70.82 min.

Mass spectroscopy analysis of pure compounds is performed on a Thermo Finnigan LCQ Deca XP Plus electrospray (ESI) instrument using both positive and negative ionization modes in a full scan mode (m/z 100-1500 Da) on a LCQ DECA XP$^{plus}$ Mass Spectrometer (Thermo Electron Corp., San Jose, Calif.). Thermo high performance liquid chromatography (HPLC) instrument equipped with Finnigan Surveyor PDA plus detector, autosampler plus, MS pump and a 4.6 mm×100 mm Luna C18 5 μm column (Phenomenex). The solvent system consists of water (solvent A) and acetonitrile (solvent B). The mobile phase begins at 10% solvent B and is linearly increased to 100% solvent B over 20 min and then kept for 4 min, and finally returned to 10% solvent B over 3 min and kept for 3 min. The flow rate is 0.5 mL/min. The injection volume was 10 μL and the samples are kept at room temperature in an auto sampler. The compounds are analyzed by LC-MS utilizing the LC and reversed phase chromatography. Mass spectroscopy analysis of the present compounds is performed under the following conditions: The flow rate of the nitrogen gas was fixed at 30 and 15 arb for the sheath and aux/sweep gas flow rate, respectively. Electrospray ionization was performed with a spray voltage set at 5000 V and a capillary voltage at 35.0 V. The capillary temperature was set at 400° C. The data was analyzed on Xcalibur software. The active compound templazole A has a molecular mass of 298 and showed m/z ion at 297.34 in negative ionization mode. The LC-MS chromatogram for templazole B suggests a molecular mass of 258 and exhibited m/z ion at 257.74 in negative ionization mode.

$^1$H, $^{13}$C and 2D NMR spectra were measured on a Bruker 500 MHz 600 MHz gradient field spectrometer. The reference is set on the internal standard tetramethylsilane (TMS, 0.00 ppm).

For structure elucidation of templazole A, the purified compound with a molecular weight 298 is further analyzed using a 500 MHz NMR instrument, and has $^1$H NMR δ values at 8.44, 8.74, 8.19, 7.47, 7.31, 3.98, 2.82, 2.33, 1.08 and has $^{13}$C NMR δ values of 163.7, 161.2, 154.8, 136.1, 129.4, 125.4, 123.5, 123.3, 121.8, 121.5, 111.8, 104.7, 52.2, 37.3, 28.1, 22.7, 22.7. Templazole A has UV absorption bands at 226, 275, 327 nm, which suggested the presence of indole and oxazole rings. The molecular formula, $C_{17}H_{18}N_2O_3$, was determined by interpretation of $^1$H, $^{13}$C NMR and HRESI MS data m/z 299.1396 (M+H)$^+$ (Calcd for $C_{17}H_{19}N_2O_3$, 299.1397), which entails a high degree of unsaturation shown by 10 double bond equivalents. The $^{13}$C NMR spectrum revealed signals for all 17 carbons, including two methyls, a methoxy, a methylene carbon, an aliphatic methine, an ester carbonyl, and eleven aromatic carbons. The presence of 3'-substituted indole was revealed from $^1$H—$^1$H COSY and HMBC spectral data. The $^1$H—$^1$H COSY and HMBC also indicated the presence of a carboxylic acid methyl ester group and a —CH$_2$—CH—(CH$_3$)$_2$ side chain. From the detailed analysis of $^1$H—$^1$H COSY, $^{13}$C, and HMBC data it was derived that the compound contained an oxazole nucleus. From the 2D analysis it was found that the iso-butyl side chain was attached at C-2 position, a carboxylic acid methyl ester at C-4 position and the indole unit at C-5 position to give templazole A.

The second herbicidally active compound, templazole B, with a molecular weight 258 is further analyzed using a 500 MHz NMR instrument, and has $^1$H NMR δ values at 7.08, 7.06, 6.75, 3.75, 2.56, 2.15, 0.93, 0.93 and $^{13}$C NMR values of δ 158.2, 156.3, 155.5, 132.6, 129.5, 129.5, 127.3, 121.8, 115.2, 115.2, 41.2, 35.3, 26.7, 21.5, 21.5. The molecular formula, is assigned as $C_{15}H_{18}N_2O_2$, which is determined by interpretation of $^1$H, $^{13}$C NMR and mass data. The $^{13}$C NMR spectrum revealed signals for all 15 carbons, including two methyls, two methylene carbons, one aliphatic methine, one amide carbonyl, and nine aromatic carbons. The general nature of the structure was deduced from $^1$H and $^{13}$C NMR spectra that showed a para-substituted aromatic ring [δ 7.08 (2H, d, J=8.8 Hz), 6.75 (2H, d, J=8.8 Hz), and 132.7, 129.5, 115.2, 127.3, 115.2, 129.5]. The $^1$H NMR spectrum of this structure together with the $^1$H—$^1$H COSY and HSQC spectra, displayed characteristic signals for an isobutyl moiety [δ 0.93 (6H, d, J=6.9 Hz), 2.15 (1H, sept., J=6.9 Hz), 2.57 (2H, d, J=6.9 Hz). In addition, an olefinic/aromatic proton at (δ 7.06, s), and a carbonyl carbon group (δ 158.9) were also found in the $^1$H and $^{13}$C NMR spectra. On inspection of the HMBC spectrum, the H-1' signal in the isobutyl moiety correlated with the olefinic carbon (C-2, δ 156.3), and the olefinic proton H-4 correlated with (C-5, δ 155.5; C-2, 156.3 & C-1", 41.2). The methylene signal at δ 3.75 correlated with C-5, C-4 as well as the C-2" of the para-substituted aromatic moiety. All these observed correlations suggested the connectivity among the isobutyl, and the para-substituted benzyl moieties for the skeleton of the structure as shown. In addition, the carboxamide group is assigned at the para position of the benzyl moiety based on the HMBC correlation from the aromatic proton at H-4"& H-6" position. Thus, based on the above data, the structure was designated as templazole B.

7. Example 7

Isolation of FR90128

The whole cell broth from the fermentation of *Burkholderia* sp. in an undefined growth medium is extracted with Amberlite XAD-7 resin (Asolkar et al., 2006) by shaking the cell suspension with resin at 225 rpm for two hours at room temperature. The resin and cell mass are collected by filtration through cheesecloth and washed with DI water to remove salts. The resin, cell mass, and cheesecloth are then soaked for 2 h in acetone after which the acetone is filtered and dried under vacuum using rotary evaporator to give the crude extract. The crude extract is then fractionated by using reversed-phase C18 vacuum liquid chromatography (H$_2$O/CH$_3$OH; gradient 90:20 to 0:100%) to give 10 fractions. These fractions are then concentrated to dryness using rotary evaporator and the resulting dry residues are screened for biological activity using both insect bioassay as well as herbicidal bioassay. The active fractions are then subjected to reversed/normal phase HPLC (Spectra System P4000; Thermo Scientific) to give pure compounds, which are then screened in herbicidal, insecticidal and nematicidal bioassays described below to locate/identify the active compounds. To confirm the identity of the compound, additional spectroscopic data such as LC/MS and NMR is recorded.

Mass spectroscopy analysis of active peaks is performed on a Thermo Finnigan LCQ Deca XP Plus electrospray (ESI) instrument using both positive and negative ionization modes in a full scan mode (m/z 100-1500 Da) on a LCQ DECA XP$^{plus}$ Mass Spectrometer (Thermo Electron Corp., San Jose, Calif.). Thermo high performance liquid chromatography (HPLC) instrument equipped with Finnigan Surveyor PDA plus detector, autosampler plus, MS pump and a 4.6 mm×100 mm Luna C18 5 μm column (Phenomenex). The solvent system consists of water (solvent A) and acetonitrile (solvent B). The mobile phase begins at 10% solvent B and is linearly increased to 100% solvent B over 20 min and then kept for 4 min, and finally returned to 10% solvent B over 3 min and kept for 3 min. The flow rate is 0.5 mL/min. The injection volume is 10 μL and the samples are kept at room temperature in an auto sampler. The compounds are analyzed by LC-MS utilizing the LC and reversed phase chromatography. Mass spectroscopy analysis of the present compounds is performed under the following conditions: The flow rate of the nitrogen gas is fixed at 30 and 15 arb for the sheath and aux/sweep gas flow rate, respectively. Electrospray ionization is performed with a spray voltage set at 5000 V and a capillary voltage at 35.0 V. The capillary temperature is set at 400° C. The data is analyzed on Xcalibur software. Based on the LC-MS analysis, the active insecticidal compound from fraction 5 has a molecular mass of 540 in negative ionization mode.

For structure elucidation, the purified insecticidal compound from fraction 5 with molecular weight 540 is further analyzed using a 500 MHz NMR instrument, and has $^1$H NMR values at 6.22, 5.81, 5.69, 5.66, 5.65, 4.64, 4.31, 3.93, 3.22, 3.21, 3.15, 3.10, 2.69, 2.62, 2.26, 2.23, 1.74, 1.15, 1.12, 1.05, 1.02; and has $^{13}$C NMR values of 172.99, 172.93, 169.57, 169.23, 167.59, 130.74, 130.12, 129.93, 128.32, 73.49, 62.95, 59.42, 57.73, 38.39, 38.00, 35.49, 30.90, 30.36, 29.26, 18.59, 18.38, 18.09, 17.93, 12.51. The NMR data indicates that the compound contains amino, ester, carboxylic acid, aliphatic methyl, ethyl, methylene, oxymethylene, methine, oxymethine and sulfur groups. The detailed 1D and 2D NMR analysis confirms the structure for the compound as FR90128 as a known compound.

8. Example 8

Herbicidal Activity of FR90128

The herbicidal activity of the active compound FR90128 (MW 540) is tested in a laboratory assay using one-week old barnyard grass (*Echinochloa crus-galla*) seedlings in a 96-well plate platform. One grass seedling was placed in each of the wells containing 99 microliters of DI water. One microliter aliquot of the pure compound in ethanol (10 mg/mL) is added into each well, and the plate is sealed with a lid. One microliter of ethanol in 99 microliters of water is used as a negative control. The treatments were done in eight replicates, and the sealed plate is incubated in a greenhouse under artificial lights (12 hr light/dark cycle). After five days, the results are read. The grass seedlings in all eight wells that received the active compound are dead with no green tissue left, whereas the seedlings in the negative control wells were actively growing.

9. Example 9

Insecticidal Activity of FR90128

The insecticidal activity of the active compound FR90128 (MW 540) is tested in a laboratory assay using a contact bioassay system. The compound is dissolved in 100% ethanol to concentrations of 0.001, 0.005, 0.01, 0.025, 0.05, 0.1, 0.25, and 0.5 µg/µL. Individual early 3$^{rd}$ instar Beet Armyworm, *Spodoptera exigua*, larvae are placed in 1.25 ounce plastic cups with a 1 cm$^2$ piece of artificial diet (Bio-Serv). A Hamilton Micropipette is used to apply 1 µL of compound to the thorax of each larvae. Cups are covered with stretched parafilm and a single hole is cut into the parafilm for aeration. Ten larvae per concentration are treated. The assay is incubated at 25° C., 12 h light/12 h dark. Larvae are scored at 48 and 72 hours after application. Probit analysis is performed to assess LC$_{50}$ value which is found for compound (MW 540) as 0.213.

10. Example 10

Isolation of Templamide A, B, FR901465 and FR90128

Methods and Materials

Figure 7:
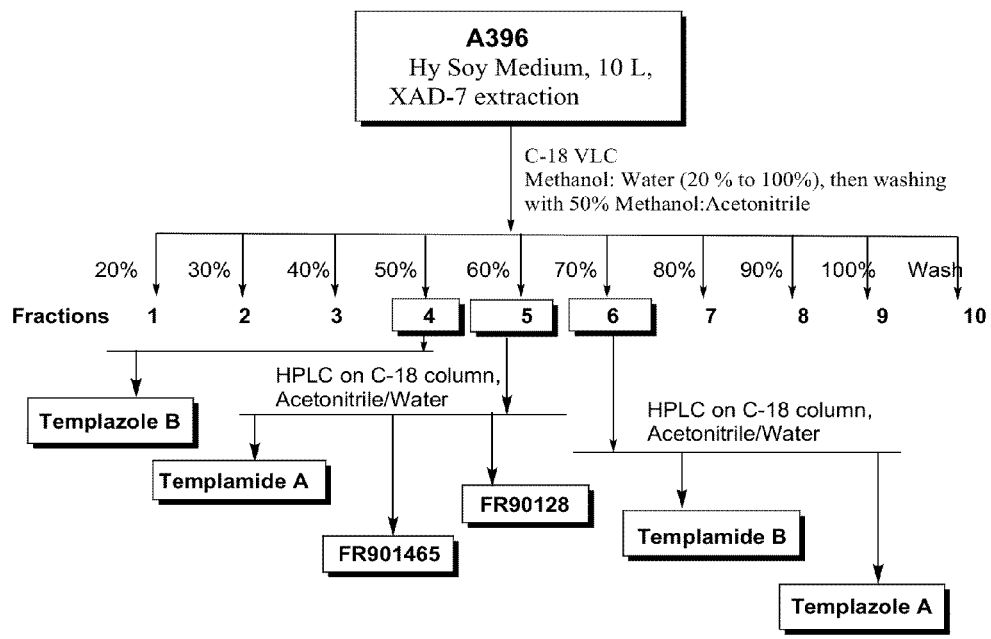

The following procedure is used for the purification of compounds extracted from cell culture of *Burkholderia* sp (see FIG. 7):

The culture broth derived from the 10-L fermentation *Burkholderia* (A396) in Hy soy growth medium is extracted with Amberlite XAD-7 resin (Asolkar et al., 2006) by shaking the cell suspension with resin at 225 rpm for two hours at room temperature. The resin and cell mass are collected by filtration through cheesecloth and washed with DI water to remove salts. The resin, cell mass, and cheesecloth are then soaked for 2 h in acetone after which the acetone is filtered and dried under vacuum using rotary evaporator to give the crude extract. The crude extract is then fractionated by using reversed-phase C18 vacuum liquid chromatography ($H_2O$/$CH_3OH$; gradient 90:20 to 0:100%) to give 10 fractions. These fractions are then concentrated to dryness using rotary evaporator and the resulting dry residues are screened for biological activity using 96 well plate lettuce seeding (herbicidal) and early 3$^{rd}$ instar Beet Armyworm (insecticidal) assay. The active fractions are then subjected to repeatedly to reversed phase HPLC separation (Spectra System P4000 (Thermo Scientific) to give pure compounds, which are then screened in above-mentioned bioassays to locate/identify the active compounds. To confirm the identity of the compound, additional spectroscopic data such as LC/MS, HRMS and NMR are recorded.

The active fraction 5 is purified further by using HPLC C-18 column (Phenomenex, Luna 10u C18(2) 100 A, 250×30), water:acetonitrile gradient solvent system (0-10 min; 80% aqueous $CH_3CN$, 10-25 min; 80-65% aqueous $CH_3CN$, 25-50 min; 65-50% aqueous $CH_3CN$, 50-60 min; 50-70% aqueous $CH_3CN$, 60-80 min; 70-0% aqueous $CH_3CN$, 80-85 min; 0-20% aqueous $CH_3CN$) at 8 mL/min flow rate and UV detection of 210 nm, to give templamide A, retention time 55.64 min and FR901465, retention time 63.59 min and FR90128, retention time 66.65 min respectively. The other active fraction 6 is also purified using HPLC C-18 column (Phenomenex, Luna 10u C18(2) 100 A, 250×30), water:acetonitrile gradient solvent system (0-10 min; 70-60% aqueous $CH_3CN$, 10-20 min; 60-40% aqueous $CH_3CN$, 20-50 min; 40-15% aqueous $CH_3CN$, 50-75 min; 15-0% $CH_3CN$, 75-85 min; 0-70% aqueous $CH_3CN$) at 8 mL/min flow rate and UV detection of 210 nm, to give templamide B, retention time 38.55 min.

Mass spectroscopy analysis of pure compounds is performed on a Thermo Finnigan LCQ Deca XP Plus electrospray (ESI) instrument using both positive and negative ionization modes in a full scan mode (m/z 100-1500 Da) on a LCQ DECA XP$^{plus}$ Mass Spectrometer (Thermo Electron Corp., San Jose, Calif.). Thermo high performance liquid chromatography (HPLC) instrument equipped with Finnigan Surveyor PDA plus detector, autosampler plus, MS pump and a 4.6 mm×100 mm Luna C18 5 μm column (Phenomenex) is used. The solvent system consists of water (solvent A) and acetonitrile (solvent B). The mobile phase begins at 10% solvent B and is linearly increased to 100% solvent B over 20 min and then kept for 4 min, and finally returns to 10% solvent B over 3 min and kept for 3 min. The flow rate is 0.5 mL/min. The injection volume is 10 μL and the samples are kept at room temperature in an auto sampler. The compounds are analyzed by LC-MS utilizing the LC and reversed phase chromatography. Mass spectroscopy analysis of the present compounds is performed under the following conditions: The flow rate of the nitrogen gas is fixed at 30 and 15 arb for the sheath and aux/sweep gas flow rate, respectively. Electrospray ionization is performed with a spray voltage set at 5000 V and a capillary voltage at 45.0 V. The capillary temperature is set at 300° C. The data is analyzed on Xcalibur software. The active compound templamide A has a molecular mass of 555 based on the m/z peak at 556.41 $[M+H]^+$ and 578.34

[M+Na]⁺ in positive ionization mode. The LC-MS analysis in positive mode ionization for templamide B suggests a molecular mass of 537 based m/z ions at 538.47 [M+H]⁺ and 560.65 [M+Na]⁺. The molecular weight for the compounds FR901465 and FR90128 are assigned as 523 and 540 respectively on the basis of LCMS analysis.

¹H, ¹³C and 2D NMR spectra are measured on a Bruker 600 MHz gradient field spectrometer. The reference is set on the internal standard tetramethylsilane (TMS, 0.00 ppm).

For structure elucidation of templamide A, the purified compound with molecular weight 555 is further analyzed using a 600 MHz NMR instrument, and has ¹H NMR δ values at 6.40, 6.39, 6.00, 5.97, 5.67, 5.54, 4.33, 3.77, 3.73, 3.70, 3.59, 3.47, 3.41, 2.44, 2.35, 2.26, 1.97, 1.81, 1.76, 1.42, 1.37, 1.16, 1.12, 1.04 and has ¹³C NMR values of δ 173.92, 166.06, 145.06, 138.76, 135.71, 129.99, 126.20, 123.35, 99.75, 82.20, 78.22, 76.69, 71.23, 70.79, 70.48, 69.84, 60.98, 48.84, 36.89, 33.09, 30.63, 28.55, 25.88, 20.37, 18.11, 14.90, 12.81, 9.41. The ¹³C NMR spectrum exhibits 28 discrete carbon signals which are attributed to six methyls, four methylene carbons, and thirteen methines including five sp², four quaternary carbons. The molecular formula, $C_{28}H_{45}NO_{10}$, is determined by interpretation of ¹H, ¹³C NMR and HRESI MS data. The detailed analysis of ¹H—¹H COSY, HMBC and HMQC spectral data reveals the following substructures (I-IV) and two isolated methylene & singlet methyl groups. These substructures are connected later using the key HMBC correlations to give the planer structure for the compound, which has been not yet reported in the literature and designated as templamide A. This polyketide molecule contains two tetrahydropyranose rings, and one conjugated amide.

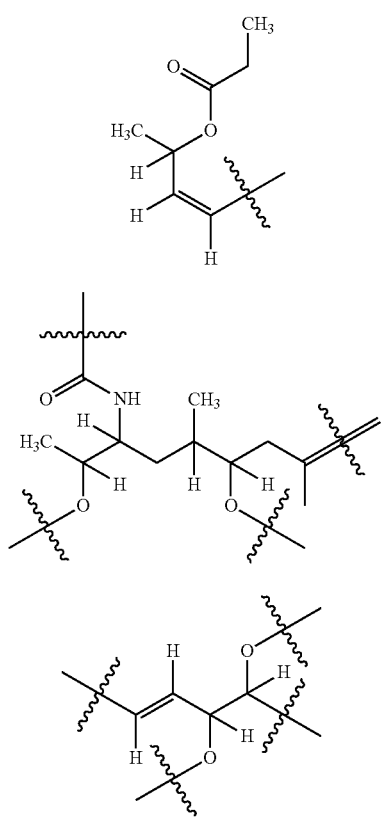

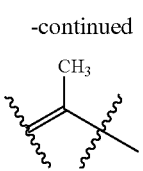

Substructures I-IV assigned by analysis of 1D & 2D NMR spectroscopic data.

The (+) ESIMS analysis for the second herbicidal compound, shows m/z ions at 538.47 [M+H]⁺ and 560.65 [M+Na]⁺ corresponding to the molecular weight of 537. The molecular formula of $C_{28}H_{43}NO_9$ is determined by interpretation of the ESIMS and NMR data analysis. The ¹H and ¹³C NMR of this compound is similar to that of templamide A except that a new isolated —CH₂— appear instead of the non-coupled methylene group in templamide A. The small germinal coupling constant of 4.3 Hz is characteristic of the presence of an epoxide methylene group. The presence of this epoxide is further confirmed from the ¹³C NMR shift from 60.98 in templamide A to 41.07 in compound with MW 537. The molecular formulae difference between these two compounds is reasonably explained by elimination of the water molecule followed by formation of epoxide. Thus, on the basis of based NMR and MS analysis the structure for the new compound was assigned and was designated as templamide B.

For structure elucidation, the purified compound from fraction 5 with molecular weight 523 is further analyzed using a 600 MHz NMR instrument, and has ¹H NMR δ values at 6.41, 6.40, 6.01, 5.98, 5.68, 5.56, 4.33, 3.77, 3.75, 3.72, 3.65, 3.59, 3.55, 3.50, 2.44, 2.26, 2.04, 1.96, 1.81, 1.75, 1.37, 1.17, 1.04; and has ¹³C NMR δ values of 172.22, 167.55, 144.98, 138.94, 135.84, 130.14, 125.85, 123.37, 99.54, 82.19, 78.28, 76.69, 71.31, 70.13, 69.68, 48.83, 42.52, 36.89, 33.11, 30.63, 25.99, 21.20, 20.38, 18.14, 14.93, 12.84. The detailed ¹H and ¹³C NMR analysis of compound suggested that this compound was quite similar to compound templamide B; the only difference was in the ester side chain; an acetate moiety was present instead of a propionate moiety in the side chain. The detailed 1D and 2D NMR analysis confirm the structure for the compound as FR901465 as a known compound.

Based on the LC-MS analysis, the other compound from fraction 5 has a molecular mass of 540 in negative ionization mode. For structure elucidation, the purified compound from fraction 5 with molecular weight 540 is further analyzed using a 500 MHz NMR instrument, and has ¹H NMR δ values at 6.22, 5.81, 5.69, 5.66, 5.65, 4.64, 4.31, 3.93, 3.22, 3.21, 3.15, 3.10, 2.69, 2.62, 2.26, 2.23, 1.74, 1.15, 1.12, 1.05, 1.02; and has ¹³C NMR values of 172.99, 172.93, 169.57, 169.23, 167.59, 130.74, 130.12, 129.93, 128.32, 73.49, 62.95, 59.42, 57.73, 38.39, 38.00, 35.49, 30.90, 30.36, 29.26, 18.59, 18.38, 18.09, 17.93, 12.51. The NMR data indicates that the compound contains amino, ester, carboxylic acid, aliphatic methyl, ethyl, methylene, oxymethylene, methine, oxymethine and sulfur groups. The detailed 1D and 2D NMR analysis confirm the structure for the compound as FR90128 as a known compound.

11. Example 11

Herbicidal Activity of Templamide A, Templamide B, FR901465 and FR90128

The herbicidal activity of templamide A, B, FR901465 and FR90128 are tested in a laboratory assay using one-week old barnyard grass (*Echinochloa crus-galla*) and lettuce (*Lactuca sativa* L.) seedlings in a 96-well plate platform. One seedling is placed in each of the wells containing 99 microliters of DI water. Into each well, a one microliter aliquot of the pure compound in ethanol (10 mg/mL) is added, and the plate is sealed with a lid. One microliter of ethanol in 99 microliters of water is used as a negative control. The treatments are done in eight replicates, and the sealed plate is incubated in a greenhouse under artificial lights (12 hr light/dark cycle). After five days, the results are read. The grass seedlings in all eight wells that received the active compound are dead with no green tissue left, whereas the seedlings in the negative control wells are actively growing. The herbicidal activity of templamide A against lettuce seedlings is slightly lower than for the grass. On the other hand, templamide B provides a better (100%) control of lettuce seedlings (used as a model system for broadleaf weeds) than templamide A (Table 11).

TABLE 11

Herbicidal Bioassay data for Templamide A, B, FR901465 and FR90128

| Compounds[1] | Grass seedlings (% Mortality) | Lettuce seedlings (% Mortality) |
| --- | --- | --- |
| Templamide A | 100 | 88 |
| Templamide B | 0 | 75 |
| FR901465 | 88 | 100 |
| FR90128 | 100 | 88 |
| Control | 0 | 0 |

[1]10 µg/mL concentration per well

12. Example 12

Insecticidal Activity of Active Compounds

The insecticidal activity of templamide A, B, FR901465 and FR90128 are tested in a laboratory assay using a 96-well diet overlay assay with 1$^{st}$ instar Beet Armyworm larvae using microtiter plates with 200 µl of solid, artificial Beet Armyworm diet in each well. One hundred (100) µl of each test sample is pipetted on the top of the diet (one sample in each well), and the sample is let dry under flowing air until the surface is dry. Each sample was tested in six replicates, and water and a commercial Bt (*B. thuringiensis*) product are used as negative and positive controls, respectively. One first instar larvae of the test insect (Beet armyworm—*Spodoptera exiqua*) was placed in each well, and the plate was covered with plastic cover with airholes. The plates with insects were incubated at 26° C. for 6 days with daily mortality evaluations. Based on the results presented in Table 12, templamide A and B results in 40% and 80% mortality, respectively.

TABLE 12

Insecticidal Bioassay data for Templamide A, B, FR901465 and FR90128 against 1$^{st}$ instar Beet Army Worm (*Spodoptera exigua*).

| Compounds[1] | (% Mortality) |
| --- | --- |
| Templamide A | 40 |
| Templamide B | 80 |
| FR901465 | 50 |
| FR90128 | 90 |

TABLE 12-continued

Insecticidal Bioassay data for Templamide A, B, FR901465 and FR90128 against 1$^{st}$ instar Beet Army Worm (*Spodoptera exigua*).

| Compounds[1] | (% Mortality) |
| --- | --- |
| Bt | 100 |
| Control | 0 |

[1]10 µg/mL concentration per well

Example 13

Fungicidal Activity of FR90128 (MW 540)

Figure 8:

Fungicidal activity of FR90128 (MW 540) against three plant pathogenic fungi (*Botrytis cinerea, Phytophtora* sp., *Monilinia fructicola*) is tested in an in vitro PDA (potato dextrose agar) plate assay. Plates are inoculated with the fungus using a plug method. After the fungus had established and started to grow on the growth medium, eight sterile filter paper disks are placed on each plate about 1 cm from the edge in a circle. Ten microliters of ethanol solution containing 20, 15, 10, 7.5, 5, 2.5 1.25 mg FR90128/mL is added into filter paper disks, and the solution is left to evaporate. One disk imbedded with 10 µL of pure ethanol is used as a negative control. The assay is done with three replicates. Plates are incubated at room temperature for 5 days, after which the fungicidal activity is recorded by measuring the inhibition zone around each filter paper disk corresponding to different concentrations of FR90128. According to the results, FR90128 has no effect on the growth of *Monilinia* but it is effective in controlling the hyphal growth of both *Botrytis* and *Phytophtora*. There seems to be a clear dose-response in inhibition with threshold concentrations of 10 mg/mL and 1.25 mg/mL for *Botrytis* and *Phytophtora*, respectively (FIG. 8).

Example 14

Herbicidal Effect of *Burkholderia* sp. A396 Formulations (Pre-Emergent)

To begin to describe the spectrum of pre-emergence activity, tests were conducted in petri dish or small pot conditions. In laboratory testing, 35 seeds were placed on a ring of blotter paper inside a 3 cm petri dish and supplied with 4 ml of MBI-010 (≤0.1 mg MBI-005/ml). Water was used as a negative control and oryzalin applied as a positive control. Petri dishes were randomly placed in a growth room at 25° C. and 50% RH. Treatments were replicated three times and germinated seeds were counted 7 and 14 days after application; water was added as necessary to maintain moisture levels inside each petri dish.

In pot testing, potting soil was placed into 4 inch square pot, into which were then inserted five weed tubers, rhizomes or other underground perennation structure, according to species. Pots were drenched with 20 mL MBI-010 at a range of dilutions with water. Treatments, including water as the negative control and glyphosate as the positive control, were replicated five times. Treatments were evaluated visually as number of germinating plants per pot and above-ground fresh weights per container were taken.

Results in Table 14 indicate broad spectrum activity on both annual grasses and broadleaves, as well as on some perennials.

TABLE 14A

| Pre-Emergent Effect of *Burkholderia* sp. A396 Formulations Pre- Emergent 010 | | | | | |
|---|---|---|---|---|---|
| Plant Category | Species (common name) | Species (scientific name) | Rating | Scale (lab/GH/field) | Product Embodiment |
| Grass, annual | Crabgrass | *Digitaria sanguinalis* | ++++ | petri dish | Supernatant |
| | Barnyardgrass | *Echionochloa crus-galli* | ++++ | petri dish | Supernatant |
| | Ryegrass | *Lolium perenne* | ++++ | petri dish | Supernatant |
| | Late Watergrass (R) | *Echinochloa phyllopogon* | + | petri dish | Supernatant |
| Broadleaf, annual | Mustard | *Brassica kaber* | ++++ | petri dish | Supernatant |
| | Crimson Clover | *Trifolium repens* | ++++ | petri dish | Supernatant |
| | Horseweed (R) | *Conyza canadensis* | ++++ | petri dish | Supernatant |
| | Palmer pigweed (R) | *Amaranthus palmerii* | ++++ | petri dish | Supernatant |
| Sdges, annual | Smallflower | *Cyperus difformis* | ++++ | petri dish | Supernatant |
| Broadleaf, perennial | Field Bindweed (root segments) | *Convolvulus arvensis* | ++++ | pots | Supernatant |
| Sedge, perennial | Puple Nutsedge (tubers) | *Cyperus rotundus* | + | pots | Supernatant |

| Rating | Scale Rating | Pre % Germinaton |
|---|---|---|
| 0 | No Effect | 95-100 |
| + | Poor | 41-95 |
| ++ | Fair | 16-40 |
| +++ | Good | 6-15 |
| ++++ | Great | 0-5 |
| S | | systemic |

Example 15

Herbicidal Effect of *Burkholderia* sp. A396 Formulations (Post-Emergent)

To begin to describe the spectrum of post-emergence activity, tests were conducted in laboratory and field conditions. For laboratory foliar applications, 3-10 plants (depending on the species) at the 1-2 leaf stage in 2.5 cm square pots containing potting soil were sprayed with MBI-010 at a rate of 40 gal/A using a cabinet track sprayer. Negative controls were sprayed with water and positive controls with glufosinate. Pots were randomly placed in a growth room at 25° C. and 50% RH, and watered as necessary. Treatments were replicated five times and evaluated at 7 and 14 days for visual % damage, with 0% indicating no damage and 100% indicating plant death.

In drench testing, potting soil was placed into 4 inch square pots containing plants at the 2-3 leaf stage. Pots were drenched with 20 mL MBI-010 at a range of dilutions with water. Treatments, including water as the negative control and oryzalin as the positive control, were replicated five times and kept in a growth room as described above. Treatments were evaluated visually on a percent control basis and above-ground fresh weights per container were taken.

In field testing, field soil containing weeds at the 1-5 leaf stage were treated with 50% 010+water solutions delivered via a hand sprayer to full coverage. Treatments, including water as the negative control and glufosinate as the positive control, were replicated 3 times and applied twice at a four week interval. Treatments were assessed for % control. Results in Table 15 indicate broad spectrum post-emergence activity on broadleaves, with little to no activity on grasses, either applied as a soil drench or as a foliar application.

TABLE 15A

| Post-Emergent Effect of *Burkholderia* sp. A396 Formulations. An S indicates an assay that successfully showed systemic activity, a 0 indicates no activity. | | | | | | |
|---|---|---|---|---|---|---|
| Plant Category | Species (common name) | Species (scientific name) | Mode | Rating | Test Scale (lab/GH/field) | Product Embodiment |
| Grass, annual | Crabgrass | *Digitaria sanguinalis* | Foliar | ++++ | Greenhouse | Prototype formulation |
| | Crabgrass | *Digitaria sanguinalis* | Drench | 0 | Greenhouse | Prototype formulation |
| | Barnyardgrass | *Echinochloa crus-galli* | Foliar | + | Greenhouse | Supernatant |

TABLE 15A-continued

| | | | | | | |
|---|---|---|---|---|---|---|
| | Barnyardgrass | *Echinochloa crus-galli* | Drench | 0 | Greenhouse | Supernatant |
| | Bluegrass | *Poa annua* | Foliar | 0 | Greenhouse | CE |
| Broadleaf, annual | Mustard | *Brassica kaber* | Foliar | ++++ | Greenhouse | Supernatant |
| | Mustard | *Brassica kaber* | Drench | +++ | Greenhouse | Supernatant |
| | Clover | *Trifolium repens* | Drench | ++++ | Greenhouse | Supernatant |
| | Lambsquarters | *Chenopodium album* | Drench | ++++ | Greenhouse | Supernatant |
| | Pigweed | *Amaranthus retroflexus* | Spot | +++ | Greenhouse | CE |
| | Pigweed | *Amaranthus retroflexus* | Foliar | ++++ | Greenhouse | Supernatant |
| | Ragweed | *Ambrosia artemisifolia* | Foliar | S | Greenhouse | WCB |
| | Black nightshade | *Solanum nigrum* | Spot | S | Greenhouse | WCB |
| | Horseweed | *Conyza canadensis* | Foliar | ++++ | Greenhouse | CE |
| | Yellow Starthistle | *Centaurea solstitialis* | Field | 0 | Field | Supernatant |
| | Mallow | *Malva* spp. | Field | ++ | Field | Supernatant |
| | Shepherd's Purse | *Capsella bursa-pastora* | Field | ++ | Field | Supernatant |
| | Henbit | *Lamium amplexicuale* | Field | 0 | Field | Supernatant |
| | California burclover | *Medicago polymorpha* | Field | +++ | Field | Supernatant |
| | Cutleaf geranium | *Geranium dissectum* | Field | ++ | Field | Supernatant |
| Broadleaf, perennial | Dandelion | *Taraxacum oficinale* | Foliar | ++ | Greenhouse | Supernatant |
| | Dandelion | *Taraxacum oficinale* | Drench | 0 | Greenhouse | Supernatant |
| | Dandelion | *Taraxacum oficinale* | Drench & Foliar | +++ | Greenhouse | Supernatant |
| | Bindweed | *Convolvulus arvensis* | Foliar | S | Greenhouse | WCB |
| | Curly Dock | *Rumex crispus* | Foliar | ++ | Greenhouse | CE |
| Crops | Fava Beans | | Foliar | ++++ | Greenhouse | WCB |
| | Snap Peas | | Foliar | ++ | Greenhouse | WCB |
| | Cucumber | | Foliar | ++++ | Greenhouse | WCB |
| | Radish | | Foliar | ++++ | Greenhouse | WCB |
| | Tomato | | Foliar | ++++ | Greenhouse | WCB |
| | Bean | | Foliar | ++ | Greenhouse | WCB |
| | Rice | | Foliar | 0 | Greenhouse | CE |
| | Wheat | | Foliar | 0 | Greenhouse | CE |
| | Sorghum | | Foliar | 0 | Greenhouse | CE |
| | Broccoli | | Foliar | 0 | Greenhouse | CE |
| | Peppers | *Capsicum annum* | Drench | 0 | Greenhouse | Supernatant |
| | Corn (conventional) | *Zea mays* | Foliar | 0 | Greenhouse | CE |
| | Libert Link Corn | *Zea mays* | Foliar | 0 | Greenhouse | CE |
| | Peanuts | *Arachis hypogaea* | Foliar | + | Greenhouse | Supernatant |

| Rating | Post % control | Scale Rating |
|---|---|---|
| 0 | 0 | No effect |
| + | 1-50 | Poor |
| ++ | 51-80 | Fair |
| +++ | 81-90 | Good |
| ++++ | 91-100 | Great |
| S | systemic | Systemic |

CE is concentrated extract; WCB is whole cell broth and Prototype Formulation is whocle cell broth with added surfactants (e.g. hostaphat or genapol)

Deposit of Biological Material

The following biological material has been deposited under the terms of the Budapest Treaty with the Agricultural Research Culture Collection (NRRL), 1815 N. University Street, Peoria, Ill. 61604 USA, and given the following number:

| Deposit | Accession Number | Date of Deposit |
| --- | --- | --- |
| Burkholderia sp. A396 | NRRL B-50319 | Sep. 15, 2009 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by government action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

LITERATURE CITED

Anderson, et al. "The structure of thiostrepton," Nature 225: 233-235. 1970.

Andra, "Endotoxin-like properties of a rhamnolipid exotoxin from *Burkholderia* (*Pseudomonas*) *plantarii*: immune cell stimulation and biophysical characterization." Biol. Chem. 387: 301-310.2006.

Arena, et al. "The mechanism of action of avermectins in *Caenorhabditis elegans*—correlation between activation of glutamate-sensitive chloride current, membrane binding and biological activity." J. Parasitol. 81: 286-294. 1995.

Asolkar, et al., "Weakly cytotoxic polyketides from a marine-derived Actinomycete of the genus *Streptomyces* strain CNQ-085." J. Nat. Prod. 69:1756-1759. 2006.

Burkhead, et al., "Pyrrolnitrin production by biological control agent *Pseudomonas cepacia* B37w in culture and in colonized wounds of potatoes." Appl. Environ. Microbiol. 60: 2031-2039. 1994.

Burkholder, W. H "Sour skin, a bacterial rot of onion bulbs." Phytopathology 40: 115-117. 1950.

Caballero-Mellado et al., "*Burkholderia unamae* sp. nov., an N2-fixing rhizospheric and endophytic species." Int. J. Syst. Evol. Microbiol. 54: 1165-1172. 2004.

Cashion et al. "Rapid method for base ratio determination of bacterial DNA." Anal. Biochem. 81: 461-466. 1977.

Casida, et al., U.S. Pat. No. 6,689,357.

Chen et al., "*Burkholderia nodosa* sp. nov., isolated from root nodules of the woody Brazilian legumes *Mimosa bimucronata* and *Mimosa scabrella*" Int. J. Syst. Evol. Microbiol. 57: 1055-1059. 2007.

Cheng, A. C. and Currie, B. J. "Melioidosis: epidemiology, pathophysiology, and management." Clin. Microbiol. 18: 383-416. 2005.

Coenye, T. and P. Vandamme, P. "Diversity and significance of *Burkholderia* species occupying diverse ecological niches." Environ. Microbiol. 5: 719-729.2003.

Compant, et al. "Diversity and occurrence of *Burkholderia* spp. in the natural environment." FEMS Microbiol. Rev. 32: 607-626. 2008.

De Ley et al. "The quantitative measurement of DNA hybridization from renaturation rates." Eur. J. Biochem. 12: 133-142. 1970.

Duke et al. "Natural products as sources for herbicides: current status and future trends." Weed Res 40: 99-111. 2000.

Gerwick et al., U.S. Pat. No. 7,393,812.

Gottlieb et al., U.S. Pat. No. 4,808,207.

Gouge et al., US Patent Application Pub. No. 2003/0082147.

Guella et al. "Almazole C, a new indole alkaloid bearing an unusually 2,5-disubstituted oxazole moiety and its putative biogenetic precursors, from a Senegalese Delesseriacean sea weed." Helv. Chim Acta 77: 1999-2006. 1994.

Guella et al. "Isolation, synthesis and photochemical properties of almazolone, a new indole alkaloid from a red alga of Senegal." Tetrahedron. 62: 1165-1170. 2006.

Henderson, P. J. and Lardy H. A. "Bongkrekic acid. An inhibitor of the adenine nucleotide translocase of mitochondria." J. Biol. Chem. 245: 1319-1326. 1970.

Hirota et al. "Isolation of indolmycin and its derivatives as antagonists of L-tryptophan." Agri. Biol. Chem. 42: 147-151. 1978.

Hu, F.-P. and Young, J. M. "Biocidal activity in plant pathogenic *Acidovorax, Burkholderia, Herbaspirillum, Ralstonia*, and *Xanthomonas* spp." J. Appl. Microbiol. 84: 263-271. 1998.

Huss et al. "Studies of the spectrophotometric determination of DNA hybridization from renaturation rates." System. Appl. Microbiol. 4: 184-192. 1983.

Jansiewicz, W. J. and Roitman J. "Biological control of blue mold and gray mold on apple and pear with *Pseudomonas cepacia*." Phytopathology 78: 1697-1700. 1988.

Jeddeloh et al., WO2001/055398.

Jansen et al. "Thiangazole: a novel inhibitor of HIV-1 from *Polyangium* Spec." Liebigs Ann. Chem. 4: 357-3359. 1992.

Jeong et al. "Toxoflavin produced by *Burkholderia glumae* causing rice grain rot is responsible for inducing bacterial wilt in many field crops." Plant Disease 87: 890-895. 2003.

Knudsen, G. R. and Spurr, J. "Field persistence and efficacy of five bacterial preparations for control of peanut leaf spot." Plant Disease 71: 442-445. 1987.

Koga-Ban et al. "cDNA sequences of three kinds of beta-tubulins from rice." DNA Research 2: 21-26. 1995.

Koide et al. US Patent Application Pub. No. 2008/0096879.

Koyama et al. "Isolation, characterization, and synthesis of pimprinine, pimrinrthine, and pimprinaphine, metabolites of *Streptoverticillium olivoreticuli*." Agri. Biol. Chem. 45: 1285-1287. 1981.

Krieg et al. "*Bacillus thuringiensis* var. *tenebrionis*: Ein neuer, gegenuber Larven von Coleopteren wirksamer Pathotyp." Z. Angew. Entomol. 96:500-508. 1983.

Kunze et al. "Thiangazole, a new thiazoline antibiotic from *Polyangium* sp (Myxobacteria Production, antimicrobial activity and mechanism of action." J. Antibiot., 46: 1752-1755. 1993.

Leahy et al. "Comparison of factors influencing trichloroethylene degradation by toluene-oxidizing bacteria." Appl. Environ. Microbiol. 62: 825-833. 1996.

Lessie et al. "Genomic complexity and plasticity of *Burkholderia cepacia*." FEMS Microbiol. Lett. 144: 117-128.1996.

Lindquist, N. et al. "Isolation and structure determination of diazonamides A and B, unusual cytotoxic metabolites from the marine ascidian *Diazona chinensis*." J. Am. Chem. Soc. 113: 2303-2304.1991.

Lorch, H et al. "Basic methods for counting microoganisms in soil and water. In *Methods in applied soil microbiology and biochemistry*. K. Alef and P. Nannipieri. Eds. San Diego, Calif., Academic Press: pp. 146-161.1995.

Ludovic et al. "*Burkholderia* diveristy and versatility: An inventory of the extracellular products." J. Microbiol. Biotechnol. 17: 1407-1429. 2007.

Lydon, J. and Duke, S. "Inhibitors of glutamine biosynthesis." in *Plant amino acids: Biochemistry and Biotechnology*. B. Singh., Ed. New York, USA, Marcel Decker. pp. 445-464.1999.

Mahenthiralingam et al. "DNA-based diagnostic approaches for identification of *Burkholderia cepacia* complex, *Burkholderia vietnamiensis, Burkholderia multivorans, Burkholderia stabilis*, and *Burkholderia cepacia* genomovars I and III." J. Clin. Microbiol. 38: 3165-3173.2000.

Ming, L.-J. and Epperson. "Metal binding and structure-activity relationship of the metalloantibiotic peptide bacitracin." Biochemistry 91: 46-58.2002.

Morita et al. "Biological activity of tropolone." Biol. Pharm. Bull. 26: 1487-1490. 2003.

Nagamatsu, T. "Syntheses, transformation, and biological activities of 7-azapteridine antibiotics: toxoflavin, fervenulin, reumycin, and their analogs". Recent Res. Devel. Org. Bioorg. Chem. 4: 97-121. 2001.

Naik et al., "Pimprine, an extracellular alkaloid produced by *Streptomyces* CDRIL-312: fermentation, isolation and pharmacological activity." J. Biotech. 88: 1-10.2001.

Nakajima et al., "Antitumor Substances, FR901463, FR901464 and FR901465.1. Taxonomy, Fermentation, Isolation, Physico-chemical Properties and Biological Activities." J. Antibiot. 49: 1196-1203. 1996.

Nakajima et al. U.S. Pat. No. 5,545,542.

Nakajima et al., "Hydantocidin: a new compound with herbicidal activity." J. Antibiot. 44: 293-300. 1991.

N'Diaye, I. et al., "Almazole A and amazole B, unusual marine alkaloids of an unidentified red seaweed of the family Delesseriaceae from the coasts of Senegal." Tet Lett. 35: 4827-4830. 1994.

N'Diaye, I. et al., "Almazole D, a new type of antibacterial 2,5-disubstituted oxazolic dipeptide from a red alga of the coast of Senegal." Tet Lett. 37: 3049-3050. 1996.

Nierman et al., "Structural flexibility in the *Burkholderia mallei* genome." Proc. Natl. Acad. Sci, USA 101: 14246-14251. 2004.

Okazaki et al., "Rhizobial strategies to enhance symbiotic interaction: Rhizobitoxine and 1-aminocyclopropane-1-carboxylate deaminase." Microbes Environ. 19: 99-111. 2004.

Parke, J. L. and D. Gurian-Sherman, D. 2001. "Diversity of the *Burkholderia cepacia* complex and implications for risk assessment of biological control strains." Annual Reviews in Phytopathology 39: 225-258. 2001.

Parke, et al. U.S. Pat. No. 6,077,505.

Pettit, G. et al. "Isolation of Labradorins 1 and 2 from *Pseudomonas syringae*." J. Nat. Prod. 65: 1793-1797.2002.

Pitt, et al., "Type characterization and antibiotic susceptibility of *Burkholderia (Pseudomonas) cepacia* isolates from patients with cystic fibrosis in the United Kingdom and the Republic of Ireland." J. Med. Microbiol. 44: 203-210. 1996.

Ramette et al., "Species abundance and diversity of *Burkholderia cepacia* complex in the environment." Appl. Environ. Microbiol. 71: 1193-1201.2005.

Resi et al., "*Burkholderia tropica* sp. nov., a novel nitrogen-fixing, plant-associated bacterium." Int. J. Syst. Evol. Microbiol. 54: 2155-2162. 2004.

Salama et al. "Potency of spore-gamma-endotoxin complexes of *Bacillus thuringiensis* against some cotton pests." Z. Angew. Entomol. 91: 388-398. 1981.

Selva et al., "Targeted screening for elongation factor Tu binding antibiotics." J. Antibiot. 50: 22-26. 1997.

Takahashi, S. et al. "Martetragin A, a novel indole alkaloid isolated from a red alga, inhibits lipid peroxidation." Chem. Pharm. Bull. 46: 1527-1529. 1998.

Thompson et al. "Spinosad—a case study: an example from a natural products discovery programme" Pest Management Science 56: 696-702. 2000.

Takita et al., "Chemistry of Bleomycin. XIX Revised structures of bleomycin and phleomycin." J. Antibiot. 31: 801-804. 1978.

Tran Van et al., "Repeated beneficial effects of rice inoculation with a strain of *Burkholderia vietnamiensis* on early and late yield component in low fertility sulphate acid soils of Vietnam." Plant and Soil 218: 273-284. 2000.

Tsuruo et al., "Rhizoxin, a macrocyclic lactone antibiotic, as a new antitumor agent against human and murine tumor cells and their vincristine-resistant sublines." Cancer Res. 46: 381-385. 1986.

Ueda et al., U.S. Pat. No. 7,396,665.

Umehara, K. et al. "Studies of new antiplatelet agents WS-30581 A and B." J. Antibiot. 37: 1153-1160. 1984.

Vandamme et al. Polyphasic taxonomic study of the emended genus *Arcobacter* with *Arcobacter butzleri* comb. nov. and *Arcobacter skirrowii* sp. nov., an aerotolerant bacterium isolated from veterinary specimens." Int. J. Syst. Bacteriol. 42: 344-356. 1992.

Vanderwall et al., "A model of the structure of HOO—Co.b-leomycin bound to d(CCAGTACTGG): recognition at the d(GpT) site and implications for double-stranded DNA cleavage, Chem. Biol. 4: 373-387. 1997.

Vermis K., et al. "Evaluation of species-specific recA-based PCR tests for genomovar level identification within the *Burkholderia cepacia* complex." J. Med. Microbiol. 51: 937-940. 2002.

Watanabe, H. et al. "A new antibiotic SF2583A, 4-chloro-5-(3'indoly)oxazole, produced by *Streptomyces*." Meiji Seika Kenkyu Nenpo 27: 55-62. 1988.

Wayne et al., "Report of the Ad Hoc committee on reconciliation of approaches to bacterial systematics." Int. J. Syst. Evol. Microbiol. 37: 463-464. 1987.

Werner et al., "Uptake of indolmycin in gram-positive bacteria." Antimicrob Agents Chemotherapy 18: 858-862. 1980.

Wilson et al. "Toxicity of rhizonin A, isolated from *Rhizopus microsporus*, in laboratory animals." Food Chem. Toxicol. 22: 275-281. 1984.

Zeck W. M. "Ein Bonitierungsschema zur Feldauswertung von Wurzelgallenbefall. Pflanzenschutznachrichten." Bayer 24, 1: 144-147. 1971.

Zhang et al., U.S. Pat. No. 7,141,407.

Zhou et al., "Antimicrobial susceptibility and synergy studies of *Burkholderia cepacia* complex isolated from patients with cystic fibrosis." Antimicrobial Agents and Chemotherapy 51: 1085-1088. 2007.

What is claimed is:

1. A method for reducing emergence and/or growth of a monocotyledonous, sedge, or dicotyledonous weed comprising applying to said weed or soil a composition comprising an isolated *Burkholderia* strain A396 (NRRL Accession No. B-50319) in an amount effective to reduce said emergence and/or growth of the monocotyledonous, sedge, or dicotyledonous weed, wherein the composition is applied prior to emergence of said weed.

2. The method according to claim 1, wherein said weed is selected from a grass weed, broadleaf weed, and sedge weed.

3. The method according to claim 2, wherein said grass weed is selected from *Digitaria sanguinalis, Echinochloa crus-galli*, and *Lolium perenne*.

4. The method according to claim 2, wherein said broadleaf weed is selected from *Brassica kaber, Trifolium repens, Conyza canadensis, Amaranthus palmeri*, and *Convolvulus arvensis*.

5. The method according to claim 2, wherein said sedge is *Cyperus difformis*.

6. The method according to claim 1, wherein the composition is a whole cell broth comprising the isolated *Burkholderia* strain A396.

7. The method of claim 6, wherein the composition further comprises at least one of a carrier, diluent, surfactant, or adjuvant.

8. The method according to claim 1, wherein the composition is a cell fraction, filtrate, supernatant, or extract of a whole cell broth comprising the isolated *Burkholderia* strain A396.

9. The method of claim 1, wherein the emergence of the weed is prevented.

10. A method of reducing growth of a monocotyledonous, sedge, or dicotyledonous weed comprising applying to said weed or soil a composition comprising an isolated *Burkholderia* strain A396 (NRRL Accession No. B-50319) in an amount effective to reduce said growth of the monocotyledonous, sedge, or dicotyledonous weed, wherein the composition is applied after emergence of said weed.

11. The method according to claim 10, wherein said weed is selected from a grass weed, broadleaf weed, and sedge weed.

12. The method according to claim 11, wherein said grass weed is selected from *Digitaria sanguinalis* and *Echinochloa crus-galli*.

13. The method according to claim 11, wherein said broadleaf weed is selected from *Brassica kaber, Trifolium repens, Conyza canadensis, Amaranthus retroflexus, Ambrosia artemisifolia, Solanum nigrum, Medicago polymorpha, Taraxacum oficinale, Convolvulus arvensis, Chenopodium album, Rumex crispus, Malva* spp., *California burclover, Geranium dissectum*, and *Capsella bursapastora*.

14. The method according to claim 11, wherein said sedge is *Cyperus difformis*.

15. The method according to claim 10, wherein the composition is a whole cell broth comprising the isolated *Burkholderia* strain A396.

16. The method of claim 15, wherein the composition further comprises at least one of a carrier, diluent, surfactant, or adjuvant.

17. The method according to claim 10, wherein the composition is a cell fraction, filtrate, supernatant, or extract of a whole cell broth comprising the isolated *Burkholderia* strain A396.

18. The method of claim 10, wherein the weed is killed.

* * * * *

```
                          SEQUENCE LISTING

<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: 27F FORWARD PRIMER - Artificial synthesized in
      laboratory

<400> SEQUENCE: 1
agagtttgat cctggctcag                                                 20

<210> SEQ ID NO 2
<211> LENGTH: 20
<212> TYPE: DNA
<213> ORGANISM: Artificial Sequence
<220> FEATURE:
<223> OTHER INFORMATION: 907R Reverse Primer - Artificial synthesized in
      laboratory

<400> SEQUENCE: 2
ccgtcaattc ctttgagttt                                                 20

<210> SEQ ID NO 3
<211> LENGTH: 16
<212> TYPE: DNA
<213> ORGANISM: Artificial Sequence
<220> FEATURE:
<223> OTHER INFORMATION: 530F Forward Primer - Artificial synthesized in
      laboratory

<400> SEQUENCE: 3
gtgccagccg ccgcgg                                                     16

<210> SEQ ID NO 4
<211> LENGTH: 16
<212> TYPE: DNA
<213> ORGANISM: Artificial Sequence
<220> FEATURE:
<223> OTHER INFORMATION: 1114F Forward Primer - Artificial synthesized
      in laboratory

<400> SEQUENCE: 4
gcaacgagcg caaccc                                                     16

<210> SEQ ID NO 5
<211> LENGTH: 17
<212> TYPE: DNA
<213> ORGANISM: Artificial Sequence
<220> FEATURE:
<223> OTHER INFORMATION: 1525R Reverse Primer - Artificial synthesized
      in laboratory

<400> SEQUENCE: 5
aaggaggtgw tccarcc                                                    17

<210> SEQ ID NO 6
<211> LENGTH: 15
<212> TYPE: DNA
<213> ORGANISM: Artificial Sequence
<220> FEATURE:
```

<223> OTHER INFORMATION: 1100R Reverse Primer - Artificial synthesized
       in laboratory

<400> SEQUENCE: 6
gggttgcgct cgttg                                                          15

<210> SEQ ID NO 7
<211> LENGTH: 18
<212> TYPE: DNA
<213> ORGANISM: Artificial Sequence
<220> FEATURE:
<223> OTHER INFORMATION: 519R Reverse Primer - Artificial synthesized in
       laboratory

<400> SEQUENCE: 7
gwattaccgc ggckgctg                                                       18

<210> SEQ ID NO 8
<211> LENGTH: 871
<212> TYPE: DNA
<213> ORGANISM: Burkholderia A396

<400> SEQUENCE: 8
tgcagtcgaa cggcagcacg ggtgcttgca cctggtggcg agtggcgaac gggtgagtaa         60
tacatcggaa catgtcctgt agtgggggat agcccggcga agccggatt aataccgcat         120 acgatctacg gatgaaagcg gggatcttc ggacctcgcg ctatagggtt ggccgatggc         180
tgattagcta gttggtgggg taaaggccta ccaaggcgac gatcagtagc tggtctgaga         240
ggacgatcag ccacactggg actgagacac ggcccagact cctacgggag gcagcagtgg         300
ggaattttgg acaatggggg aaaccctgat ccagcaatgc cgcgtgtgtg aagaaggcct         360
tcgggttgta aagcactttt gtccggaaag aaatcctttg gctaatacc ccgggggat          420 gacggtaccg gaagaataag caccggctaa ctacgtgcca gcagccgcgg taatacgtag         480
ggtgcgagcg ttaatcggaa ttactgggcg taaagcgtgc gcaggcggtt tgttaagaca         540
gatgtgaaat ccccgggctt aacctgggaa ctgcatttgt gactggcaag ctagagtatg         600
gcagaggggg gtagaattcc acgtgtagca gtgaaatgcg tagagatgtg gaggaatacc         660
gatggcgaag gcagccccct gggccaatac tgacgctcat gcacgaaagc gtggggagca         720
aacaggatta gataccctgg tagtccacgc cctaaacgat gtcaactagt tgttggggat         780
tcatttcctt agtaacgtag ctacgcgtga agttgaccgc ctggggagta cggtcgcaag         840
attaaatmga gggtkgkktg kkggggggaa a                                        871

<210> SEQ ID NO 9
<211> LENGTH: 1453
<212> TYPE: DNA
<213> ORGANISM: Burkholderia A396

<400> SEQUENCE: 9
gtcatgaatc ctaccgtggt gaccgtcctc cttgcggtta gactagccac ttctggtaaa         60
acccactccc atggtgtgac gggcggtgtg tacaagaccc gggaacgtat tcaccgcggc         120
atgctgatcc gcgattacta gcgattccag cttcatgcac tcgagttgca gagtgcaatc         180
cggactacga tcggttttct gggattagct ccccctcgcg ggttggcaac cctctgttcc         240
gaccattgta tgacgtgtga agccctaccc ataagggcca tgaggacttg acgtcatccc         300
caccttcctc cggtttgtca ccggcagtct ccttagagtg ctcttgcgta gcaactaagg         360
acaagggttg cgctcgttgc gggacttaac ccaacatctc acgacacgag ctgacgacag         420

```
ccatgcagca cctgtgtatc ggttctcttt cgagcactcc cgaatctctt caggattccg    480
accatgtcaa gggtaggtaa ggttttttcgc gttgcatcga attaatccac atcatccacc   540
gcttgtgcgg gtccccgtca attcctttga gttttaatct tgcgaccgta ctccccaggc    600
ggtcaacttc acgcgttagc tacgttacta aggaaatgaa tccccaacaa ctagttgaca    660
tcgtttaggg cgtggactac cagggtatct aatcctgttt gctccccacg ctttcgtgca    720
tgagcgtcag tattggccca gggggctgcc ttcgccatcg gtattcctcc acatctctac    780
gcatttcact gctacacgtg gaattctacc cccctctgcc atactctagc ttgccagtca    840
caaatgcagt tcccaggtta agcccgggga tttcacatct gtcttaacaa accgcctgcg    900
cacgctttac gcccagtaat tccgattaac gctcgcaccc tacgtattac gcggctgct     960 ggcacgtagt tagccggtgc ttattcttcc ggtaccgtca tccccccggg gtattagccc   1020
aaaggatttc tttccggaca aaagtgcttt acaacccgaa ggccttcttc acacacgcgg   1080
cattgctgga tcagggtttc ccccattgtc caaaattccc cactgctgcc tcccgtagga   1140
gtctgggccg tgtctcagtc ccagtgtggc tgatcgtcct ctcagaccag ctactgatcg   1200
tcgccttggt aggcctttac cccaccaact agctaatcag ccatcggcca acctatagc    1260 gcgaggtccg aagatccccc gctttcatcc gtagatcgta tgcggtatta atccggcttt   1320
cgccgggcta tccccccacta caggacatgt tccgatgtat tactcacccg ttcgccactc   1380
gccaccaggt gcaagcaccc gtgctgccgt tcgacttgca tgtgtaaggc atgccgccag   1440
cgttcaatct gag                                                     1453

<210> SEQ ID NO 10
<211> LENGTH: 860
<212> TYPE: DNA
<213> ORGANISM: Burkholderia A396

<400> SEQUENCE: 10
ccaggcggtc acttcacgcg ttagctacgt tactaaggaa atgaatcccc aacaactagt     60
tgacatcgtt tagggcgtgg actaccaggg tatctaatcc tgtttgctcc ccacgctttc    120
gtgcatgagc gtcagtattg gcccaggggg ctgccttcgc catcggtatt cctccacatc    180
tctacgcatt tcactgctac acgtggaatt ctaccccct ctgccatact ctagcttgcc    240
agtcacaaat gcagttccca ggttaagccc ggggatttca catctgtctt aacaaaccgc    300
ctgcgcacgc tttacgccca gtaattccga ttaacgctcg caccctacgt attaccgcgg    360
ctgctggcac gtagttagcc ggtgcttatt cttccggtac cgtcatcccc cggggtatt    420 agcccaaagg atttctttcc ggacaaaagt gctttacaac ccgaaggcct tcttcacaca    480
cgcggcattg ctggatcagg gtttccccca ttgtccaaaa ttccccactg ctgcctcccg    540
taggagtctg gccgtgtct cagtcccagt gtggctgatc gtcctctcag accagctact    600
gatcgtcgcc ttggtaggcc tttacccac caactagcta atcagccatc ggccaaccct    660
atagcgcgag gtccgaagat ccccgctt catccgtaga tcgtatgcgg tattaatccg     720
gctttcgccg gctatcccc cactacagga catgttccga tgtattactc acccgttcgc    780
cactcgccac caggtgcaag cacccgtgct gccgttcgac ttgcatgtgt aaggcatgcc    840
gccagcgttc aatctgagtg                                               860

<210> SEQ ID NO 11
<211> LENGTH: 1152
<212> TYPE: DNA
```

<213> ORGANISM: Burkholderia A396

<400> SEQUENCE: 11

```
tcggattact gggcgtaagc gtgcgcaggc ggtttgttaa gacagatgtg aaatccccgg     60
gcttaacctg ggaactgcat ttgtgactgg caagctagag tatggcagag gggggtagaa    120
ttccacgtgt agcagtgaaa tgcgtagaga tgtggaggaa taccgatggc gaagggagcc    180
ccctgggcct atactgaccc tcatgctcga aagcgtgagg acccaaccgg attagatgcc    240
ctgataggcc atgccccaca ccatgccatg tgttaggggc ccatttcctt agggaggcag    300
ctatggggaa ttttggacaa tgtgggaaac cctgatccaa caatgccgcg tgtgtgaata    360
aggccttcgg gttgtaaagc acttttatcc ggatagattc cttttgggct aaacctccgt    420
aggggatgac ggtaccggaa gaataaccac cgggtaacta cgtgccagca gccgcggtaa    480
tacgtagggt gcgagcgtta atcggaatta ctgggcgtaa agcgtgcgca ggcggtttgt    540
taagacagat gtgaaatccc cgggcttaac ctgggaactg catttgtgac tggcaagcta    600
gagtatggca gacgggggta gaattccacg tgtagcagtg aaatgcgtag agatgtggag    660
gaataccgat gggcgaagca gctcctgggg caatactgac gctcatgcac aagatcgtgc    720
gaaacaaaca ggataaaacc cctgtattcc acgcccaaaa cgatgtccac caagttgttg    780
gcgatccttt ccttcgtatc gtagctacgc gggaatttga ccccctgggg actaggccgc    840
atataaaact caagggaatt ccggggaccc ccagagctgt gtatgatgtg attattccga    900
tgcgcggaaa accttcctta tctttgaatg gcggtactcc tgaaaattgc ggagtgctcg    960
aaaacaccga acccgggtct ttctgcgtgt cctccctcgt gtgggatatg ctggatatcc   1020
cgcagacgca tctttgactt agtgctccca aaactgagag ctgggaggac tcgagagggg   1080
atccctgcct ccccggcttg ggtgctcccc ttatggggga aacaggtaca cggggggatc   1140
atcccatacc ta                                                       1152
```

<210> SEQ ID NO 12
<211> LENGTH: 1067
<212> TYPE: DNA
<213> ORGANISM: Burkholderia A396

<400> SEQUENCE: 12

```
tctaaggaga ctgccggtga caaaccggag gaaggtgggg atgacgtcaa gtcctcatgg     60
cccttatggg tagggcttca cacgtcatac aatggtcgga acagagggtt gccaacccgc    120
gagggggagc taatcccaga aaaccgatcg tagtccggat tgcactctgc aactcgagtg    180
catgaagctg gaatcgctag taatcgcgga tcagcatgcc gcggtgaata cgttcccggg    240
tcttgtacac accgcccgtc acaccatggg agtgggtttt accagaagtg gctagtctaa    300
ccgcaaggag gacggtcacc acggtaggat tcatgactgg ggtgaagtcg taacaaggta    360
gccgtatcgg aaggtgcggc tggatcacct ccttaaaccc tttggcctaa taaccccggg    420
ggaataagta ccgaaaaaaa aaaaaactgg ataacttccg tgccacaacc cgcggaaaaa    480
tctagggggg gggagcttaa atggaaattt acggggccgt aaagcgtgcg caggcggttt    540
gtaaacacag atgtgaaatc cccgggctta acctgggaac tgcatttgtg actggcaagc    600
tagagtatgg cacagggggg tagaattcca cgtgtagcat tgaatgcata gagatgagag    660
gataccgatg gagaagggcg cccccgggga caatatgacg cctatgccac aaagctgtgg    720
cacaataggt taaatacctg tgttgtcccc gcctaaacag attacacttg ttgtgggtat    780
tttctcataa aatactacac acgggagaat acactggggg gcttcgtcaa ttatcacaac    840
```

```
aatgattgcg ggcacccacg ggggtagatg ggtaataaat cgacggcaac tatctactta    900
cttggatgat cgcacagatt gggcgggaga aagagaaca gcgtgtgtgt gctcctccgc     960
gagtgatagg taatcggaca atactttgac aggacttaac tgggtagcgg atcgagtgg   1020 attcccgtcg gatggcctcc gcaggtacgg cagctgggga ttacatc                1067
```

<210> SEQ ID NO 13
<211> LENGTH: 1223
<212> TYPE: DNA
<213> ORGANISM: Burkholderia A396

<400> SEQUENCE: 13

```
ttgcttacga cttcacccca gtcatgaatc ctaccgtggt gaccgtcctc cttgcggtta    60
gactagccac ttctggtaaa acccactccc atggtgtgac gggcggtgtg tacaagaccc   120
gggaacgtat tcaccgcggc atgctgatcc gcgattacta gcgattccag cttcatgcac   180
tcgagttgca gagtgcaatc cggactacga tcggttttct gggattagct ccccctcgcg   240
ggttggcaac cctctgttcc gaccattgta tgacgtgtga agccctaccc ataagggcca   300
tgaggacttg acgtcatccc caccttcctc cggtttgtca ccggcagtct ccttagagtg   360
ctcttgcgta gcaactaagg acaagggttg cgctcgttgc gggacttaac ccaacatctc   420
acgacacgag ctgacgacag ccatgcagca cctgtgtatc ggttctcttt cgagcactcc   480
cgaatctctt caggattccg accatgtcaa gggtaggtaa ggttttttcgc gttgcatcga   540 attaatccac atcatccacc gcttgtgcgg gtccccgtca attcctttga gttttaatct   600
tgcgaccgta ctccccaggc ggtcaacttc acgcgttagc tacgttacta aggaaatgaa   660
tccccaacaa ctagttgaca tcgtttaggg cgtggactac cagggtatct aatcctgttt   720
gctccccacg ctttcgtgca tgagcgtcag tattggccca ggggctgcc ttcgccatcg    780 gtattcctcc acatctctac gcatttcact gctacgtg gaattctacc ccctctgcc     840 atactctagc ttgccagtca caaatgcagt tcccaggtta agcccgggga tttcacatct   900
gtcttaacaa accgcctgcg cacgctttac gcccagtaat ccgattaac gctcgcaccc    960 tacgtattac cgcggctgct ggcacgtagt tagccggtgc ttattctgcg gtaccgtcat  1020
cccccgggta tagcccaaag gattctttcg acaaagtgct ttacacccga tgtctctcac  1080
acacgcgcat gctgatcagg tttccccatg tcaaagtcca ctgctgctcg taggtctgga  1140
cgggttcagt tcaatgtgac tgatcgtctt tcgacaacta ctgaacgtcc ctgtagctta  1200
cccaccaact agctatagca tgc                                          1223
```

<210> SEQ ID NO 14
<211> LENGTH: 1216
<212> TYPE: DNA
<213> ORGANISM: Burkholderia A396

<400> SEQUENCE: 14

```
ccgagctgac gacagccatg cagcacctgt gtatcggttc tctttcgagc actcccgaat    60
ctcttcagga ttccgaccat gtcaagggta ggtaaggttt ttcgcgttgc atcgaattaa   120
tccacatcat ccaccgcttg tgcgggtccc cgtcaattcc tttgagtttt aatcttgcga   180
ccgtactccc caggcggtca acttcacgcg ttagctacgt tactaaggaa atgaatcccc   240
aacaactagt tgacatcgtt tagggcgtgg actaccaggg tatctaatcc tgtttgctcc   300
ccacgctttc gtgcatgagc gtcagtattg gcccaggggg ctgccttcgc catcggtatt   360
```

```
cctccacatc tctacgcatt tcactgctac acgtggaatt ctaccccct ctgccatact    420 ctagcttgcc agtcacaaat gcagttccca ggttaagccc ggggatttca catctgtctt    480
aacaaaccgc ctgcgcacgc tttacgccca gtaattccga ttaacgctcg caccctacgt    540
attaccgcgg ctgctggcac gtagttagcc ggtgcttatt cttccggtac cgtcatcccc    600
ccggggtatt agcccaaagg atttctttcc ggacaaaagt gctttacaac ccgaaggcct    660
tcttcacaca cgcggcattg ctggatcagg gtttccccca ttgtccaaaa ttccccactg    720
ctgcctcccg taggagtctg ggccgtgtct cagtcccagt gtggctgatc gtcctctcag    780
accagctact gatcgtcgcc ttggtaggcc tttaccccac caactagcta atcagccatc    840
ggccaaccct atagcgcgag gtccgaagat cccccgcttt catccgtaga tcgtatgcgg    900
tattaatccg gctttcgccg ggctatcccc cactacagga catgttccga tgtattactc    960
acccgttcgc cactcgcccc aggtgcaagc accgtgctg ccgttcgact tgcatgtgta   1020
gcatgcgcag cgtcatctac taaataaaca actctaagaa ttttgcccg agggcctcta   1080 aacactcggg gcgtcgagag agactacgga tgaggagcat ccctctgtct ctaggtatgt   1140
gttgtcgcct ctctcacaga ggaggggacg cacgacggag ccatcgggga cgacaacatg   1200
tacgatatac tatcta                                                   1216

<210> SEQ ID NO 15
<211> LENGTH: 1194
<212> TYPE: DNA
<213> ORGANISM: Burkholderia A396

<400> SEQUENCE: 15
ttcttcggta ccgtcatccc ccgggggtat agcccaaag gatttctttc cggacaaaag     60
tgctttacaa cccgaaggcc ttcttcacac acgcggcatt gctggatcag gtttccccc    120 attgtccaaa attccccact gctgcctccc gtaggagtct gggccgtgtc tcagtcccag   180
tgtggctgat cgtcctctca gaccagctac tgatcgtcgc cttggtaggc ctttacccca   240
ccaactagct aatcagccat cggccaaccc tatagcgcga ggtccgaaga tccccgctt   300 tcatccgtag atcgtatgcg gtattaatcc ggctttcgcc gggctatccc ccactacagg   360
acatgttccg atgtattact cacccgttcg ccactcgcca ccaggtgcaa gcacccgtgc   420
tgccgttcga cttgcatgtg taaggcatgc cgccagcgtt caatctgagc catgatcaaa   480
ctctgagggg gggggccttc aacggaacga ctgggcaaaa agcgtgccca ggcgttttgt   540
taagacagat gtgaaacccc ggggcttaac ctggaaactg catttgtgac tggaaagcta   600
gagtatggca gaggggggta gaattccacg tgtagcattg aaatgcgtag aaatggagag   660
gaataccgat gggagagggc agcccccgtg gcaaatact ggcgcttatg aacaaagttg   720
gggcgcgccg ccgggatatg ttcccctggg atatcccccc cctaaactgc ttacaaatat   780
tgtgtgggaa acttttctc taaaaaatag aacacaacgg gagatatcac ccccgggggg   840
ccaccgccag attaaacccc caaaaagtat ttggcgggca ccccccgggg gggtgagatg   900
gggtaaaata aatccgtgcg acgagcaaac cctccccaca cctgggatgg tcgcgaccac   960
agatgagatg cgggcggaga gaacgatacc caagcgtggt tgtttgcctg catcccctcc   1020
gtcgggagtg gatatagtag agtaattacg gcacgactgc atttttttt cttcagtaca   1080 ccttatcaca ctgttggatg caccgcgaga aatccggagg tgtgagtact cccccctct   1140 cctcgggatg tgtcggcgct cccttctccc gttcagggt gggtaagcac cgcg          1194
```